US009011859B2

(12) United States Patent
Burkly et al.

(10) Patent No.: US 9,011,859 B2
(45) Date of Patent: *Apr. 21, 2015

(54) METHODS FOR TREATING TWEAK-RELATED CONDITIONS

(71) Applicant: Biogen Idec MA Inc., Cambridge, MA (US)

(72) Inventors: Linda C. Burkly, West Newton, MA (US); Aniela Jakubowski, Arlington, MA (US); Timothy Zheng, Boston, MA (US); Kyungmin Hahm, Auburndale, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/860,983

(22) Filed: Apr. 11, 2013

(65) Prior Publication Data

US 2013/0216496 A1   Aug. 22, 2013

Related U.S. Application Data

(63) Continuation of application No. 13/179,096, filed on Jul. 8, 2011, now abandoned, which is a continuation of application No. 12/417,755, filed on Apr. 3, 2009, now Pat. No. 8,506,958, which is a continuation of application No. 10/510,804, filed as application No. PCT/US03/11350 on Apr. 9, 2003, now abandoned.

(60) Provisional application No. 60/371,611, filed on Apr. 9, 2002.

(51) Int. Cl.
| A61K 39/395 | (2006.01) |
| C07K 16/28 | (2006.01) |
| C07K 14/705 | (2006.01) |
| C07K 14/435 | (2006.01) |
| C07K 16/24 | (2006.01) |
| C07K 14/525 | (2006.01) |
| C07K 16/22 | (2006.01) |
| A61K 38/00 | (2006.01) |
| A61K 39/00 | (2006.01) |

(52) U.S. Cl.
CPC ........... *C07K 16/241* (2013.01); *A01K 2217/05* (2013.01); *A61K 38/00* (2013.01); *A61K 2039/505* (2013.01); *C07K 14/70575* (2013.01); *C07K 16/2875* (2013.01); *C07K 2319/00* (2013.01); *C07K 2319/30* (2013.01); *C07K 14/525* (2013.01); *C07K 16/22* (2013.01)

(58) Field of Classification Search
None
See application file for complete search history.

(56) References Cited

U.S. PATENT DOCUMENTS

| 4,921,698 | A | 5/1990 | Shirai et al. |
| 5,073,492 | A | 12/1991 | Chen et al. |
| 5,200,313 | A | 4/1993 | Carrico |
| 5,223,409 | A | 6/1993 | Ladner et al. |
| 5,225,539 | A | 7/1993 | Winter |
| 5,624,821 | A | 4/1997 | Winter et al. |
| 5,648,260 | A | 7/1997 | Winter et al. |
| 5,693,762 | A | 12/1997 | Queen et al. |
| 5,858,991 | A | 1/1999 | Hellerqvist et al. |
| 5,859,205 | A | 1/1999 | Adair et al. |
| 5,885,793 | A | 3/1999 | Griffiths et al. |
| 6,046,381 | A | 4/2000 | Mucke et al. |
| 6,207,642 | B1 | 3/2001 | Wiley |
| 6,300,064 | B1 | 10/2001 | Knappik et al. |
| 6,407,213 | B1 | 6/2002 | Carter et al. |
| 6,448,042 | B1 | 9/2002 | Greene et al. |
| 6,544,761 | B2 | 4/2003 | Greene et al. |
| 6,727,225 | B2 | 4/2004 | Wiley |
| 6,824,773 | B2 | 11/2004 | Wiley |
| 6,943,146 | B2 | 9/2005 | Jakubowski et al. |
| 7,067,475 | B2 | 6/2006 | Cerretti et al. |
| 7,074,408 | B2 | 7/2006 | Fanslow, III et al. |
| 7,087,225 | B2 | 8/2006 | Yu et al. |
| 7,087,725 | B2 | 8/2006 | Browning et al. |
| 7,109,298 | B2 | 9/2006 | Browning et al. |
| 7,129,061 | B1 | 10/2006 | Browning et al. |

(Continued)

FOREIGN PATENT DOCUMENTS

| CA | 2064710 A1 | 11/1991 |
| EP | 1354950 A1 | 10/2003 |

(Continued)

OTHER PUBLICATIONS

Bateller et al., J Clinical Investigation 115(2): 209-218, Feb. 2005.*
Boor et al., Nephrol Dial Transplant 22: 3391-3407, 2009.*
Hill et al, Kidney International 61: 2176-2186, 2002.*
[No Authors Listed], "Abetimus: Abetimus sodium, LJP 394" *BioDrugs* 17(3):212-215 (2003) (Abstract only).
Abbas, A.K. et al. (eds.), "General Properties of Immune Responses", in *Introduction to Immunology, Cellular and Molecular Immunology*. Philadelphia: WB Saunders Co., 1991; Chapter One, pp. 4-12.
Abbas, A.K. et al. (eds.), "Immunity to Microbes", in *Introduction to Immunology. Cellular and Molecular Immunology*. Philadelphia: WB Saunders Co., 1991; Chapter Fifteen, pp. 302-314.
Abreu-Martin et al., "Divergent Induction of Apoptosis and IL-8 Secretion in HT-29 Cells in Response to TNF-α and Ligation of Fas Antigen", *J. Immunol.* 155:4147-4154 (1995).

(Continued)

*Primary Examiner* — Phuong Huynh
(74) *Attorney, Agent, or Firm* — Fish & Richardson P.C.

(57) ABSTRACT

The present invention provides methods and agents for the treatment of TWEAK-related conditions, including cardiac, liver, kidney, lung, adipose, skeletal, muscle, neuronal, bone and cartilage conditions. The invention also provides methods for identifying TWEAK agonists or antagonists for the treatment of TWEAK-related conditions. Additionally, the invention provides transgenic animals that express an exogenous DNA encoding a TWEAK polypeptide, or fragments, analogs, or muteins thereof, and methods for using such animals to identify TWEAK agonists or antagonists. The invention further provides methods for diagnosing a disease based on TWEAK expression. The invention also provides methods for affecting cellular differentiation of progenitor cells using TWEAK polypeptides, agonists, or antagonists.

22 Claims, 25 Drawing Sheets

(56) References Cited

U.S. PATENT DOCUMENTS

| | | |
|---|---|---|
| 7,169,387 B2 | 1/2007 | Rennert |
| 7,208,151 B2 | 4/2007 | Browning et al. |
| 7,482,430 B2 | 1/2009 | Wiley |
| 7,495,086 B2 | 2/2009 | Kim et al. |
| 7,498,304 B2 | 3/2009 | Kotkow et al. |
| 7,507,807 B2 | 3/2009 | Wiley |
| 7,517,962 B2 | 4/2009 | Wiley |
| 7,566,769 B2 | 7/2009 | Browning et al. |
| 7,579,001 B2 * | 8/2009 | Rennert ............ 424/145.1 |
| 7,695,934 B2 | 4/2010 | Browning et al. |
| 7,731,963 B2 | 6/2010 | Browning et al. |
| 7,732,588 B2 | 6/2010 | Wiley |
| 7,829,675 B2 | 11/2010 | Kim et al. |
| 8,048,422 B2 | 11/2011 | Burkly et al. |
| 8,048,635 B2 | 11/2011 | Burkly et al. |
| 8,440,189 B2 * | 5/2013 | Rennert ............ 424/130.1 |
| 8,506,958 B2 * | 8/2013 | Burkly et al. ...... 424/130.1 |
| 2002/0004041 A1 | 1/2002 | Albert et al. |
| 2002/0015703 A1 * | 2/2002 | Rennert ............ 424/143.1 |
| 2002/0042368 A1 | 4/2002 | Fanslow, III et al. |
| 2002/0110853 A1 | 8/2002 | Wiley |
| 2003/0100074 A1 | 5/2003 | Yu et al. |
| 2003/0148314 A1 | 8/2003 | Berger et al. |
| 2003/0162712 A1 | 8/2003 | Cerretti et al. |
| 2003/0170228 A1 | 9/2003 | Ashkenazi et al. |
| 2003/0198640 A1 | 10/2003 | Yu et al. |
| 2003/0211096 A1 | 11/2003 | Ashkenazi et al. |
| 2003/0211993 A1 | 11/2003 | Jakubowski et al. |
| 2003/0216546 A1 | 11/2003 | Tykocinski et al. |
| 2004/0014176 A1 | 1/2004 | Ashkenzai et al. |
| 2004/0018170 A1 | 1/2004 | Shirwan |
| 2004/0033225 A1 | 2/2004 | Browning et al. |
| 2004/0033495 A1 | 2/2004 | Murray et al. |
| 2004/0038349 A1 | 2/2004 | Hilbert et al. |
| 2004/0047854 A1 | 3/2004 | Black et al. |
| 2004/0076955 A1 | 4/2004 | Mack et al. |
| 2004/0091473 A1 | 5/2004 | DuBose et al. |
| 2004/0175744 A1 | 9/2004 | Hu et al. |
| 2004/0176296 A1 | 9/2004 | Holtzman et al. |
| 2004/0203083 A1 | 10/2004 | Buechler et al. |
| 2005/0008625 A1 | 1/2005 | Balint et al. |
| 2005/0008636 A1 | 1/2005 | Rennert |
| 2005/0054568 A1 | 3/2005 | Ling et al. |
| 2005/0079574 A1 | 4/2005 | Bond |
| 2005/0112666 A1 | 5/2005 | Browning et al. |
| 2005/0118629 A1 | 6/2005 | Browning et al. |
| 2005/0181375 A1 | 8/2005 | Aziz et al. |
| 2005/0208500 A1 | 9/2005 | Erlander et al. |
| 2006/0003932 A1 | 1/2006 | Jakubowski et al. |
| 2006/0240004 A1 | 10/2006 | Burkly et al. |
| 2007/0280940 A1 | 12/2007 | Winkles et al. |
| 2008/0187544 A1 | 8/2008 | Burkly et al. |
| 2008/0241163 A1 | 10/2008 | Burkly et al. |
| 2008/0279853 A1 | 11/2008 | Burkly et al. |
| 2008/0286271 A1 | 11/2008 | Ashkenazi et al. |
| 2008/0292622 A1 | 11/2008 | Burkly et al. |
| 2009/0068102 A1 | 3/2009 | Burkly et al. |
| 2009/0124993 A1 | 5/2009 | Burkly et al. |
| 2009/0311313 A1 | 12/2009 | Burkly et al. |
| 2009/0324602 A1 | 12/2009 | Garber et al. |
| 2010/0061985 A1 | 3/2010 | Rennert |
| 2010/0183548 A1 | 7/2010 | Wiley |
| 2010/0260761 A1 | 10/2010 | Browning et al. |
| 2010/0272721 A1 | 10/2010 | Burkly et al. |
| 2010/0284933 A1 | 11/2010 | Burkly |
| 2011/0002924 A1 | 1/2011 | Browning et al. |
| 2012/0009178 A1 | 1/2012 | Burkly et al. |
| 2012/0014953 A1 | 1/2012 | Burkly et al. |
| 2012/0015024 A1 | 1/2012 | Burkly et al. |
| 2012/0020913 A1 | 1/2012 | Burkly |
| 2012/0020970 A1 | 1/2012 | Burkly et al. |
| 2012/0121583 A1 | 5/2012 | Baehner et al. |
| 2012/0183542 A1 | 7/2012 | Burkly et al. |

FOREIGN PATENT DOCUMENTS

| | | |
|---|---|---|
| EP | 1566636 A1 | 8/2005 |
| JP | 5-501062 A | 3/1993 |
| JP | 2002-527096 | 8/2002 |
| WO | WO 95/14772 A1 | 6/1995 |
| WO | WO 96/18725 A1 | 6/1996 |
| WO | WO 98/05783 A1 | 2/1998 |
| WO | WO 98/35061 A2 | 8/1998 |
| WO | WO 98/52976 A1 | 11/1998 |
| WO | WO 98/55508 A2 | 12/1998 |
| WO | WO 99/11791 A2 | 3/1999 |
| WO | WO 99/19490 A1 | 4/1999 |
| WO | WO 99/59614 A1 | 11/1999 |
| WO | WO 99/61471 A2 | 12/1999 |
| WO | WO 00/23459 A1 | 4/2000 |
| WO | WO 00/34317 A2 | 6/2000 |
| WO | WO 00/37638 A2 | 6/2000 |
| WO | WO 00/42073 A1 | 7/2000 |
| WO | WO 01/45730 A2 | 6/2001 |
| WO | WO 01/53486 A1 | 7/2001 |
| WO | WO 01/85193 A2 | 11/2001 |
| WO | WO 02/22166 A2 | 3/2002 |
| WO | WO 02/102994 A2 | 12/2002 |
| WO | WO 03/040307 A2 | 5/2003 |
| WO | WO 03/086311 A2 | 10/2003 |
| WO | WO 2005/010045 A1 | 2/2005 |
| WO | WO 2005/080972 A1 | 9/2005 |
| WO | WO 2006/047172 A1 | 5/2006 |
| WO | WO 2006/052926 A2 | 5/2006 |
| WO | WO 2006/088890 A2 | 8/2006 |
| WO | WO 2006/089095 A2 | 8/2006 |
| WO | WO 2006/096487 A2 | 9/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/138219 A2 | 12/2006 |
| WO | WO 2008/048924 A2 | 4/2008 |
| WO | WO 2009/140177 A2 | 11/2009 |
| WO | WO 2010/085648 A2 | 7/2010 |
| WO | WO 2010/088534 A1 | 8/2010 |

OTHER PUBLICATIONS

Agrawal, "Antisense Oligonucleotides: Towards Clinical Trials", *TIBTECH* 14:376-387 (1996).

Akahori et al., "Immunoglobulin kappa light chain VLJ region [*Homo sapiens*]", NCBI database accession No. GI:21669075, GenBank Accession No. BAC01562 (Jun. 25, 2001).

Alarcón-Segovia et al., "LJP 394 for the Prevention of Renal Flare in Patients With Systemic Lupus Erythematosus" *Arthritis & Rheumatism* 48(2):442-454 (2003).

Amakawa et al., "Impaired Negative Selection of T Cells in Hodgkin's Disease Antigen CD30-Deficient Mice", *Cell* 84:551-562 (1996).

Anderson, "Human Gene Therapy", *Nature* 392:25-30 (1998).

Andrews et al., "Spontaneous Murine Lupus-like Syndromes", *J. Exp. Med.* 148:1198-1215 (1978).

Angal et al., "A single amino acid substitution abolishes the heterogeneity of chimeric mouse/human (IgG4) antibody", *Mol. Immunol.* 30:105-108 (1993).

Ashkenazi et al., "Death Receptors: Signaling and Modulation", *Science, New Series* 281(5381):1305-1308 (1998).

Bach-Elias et al., "Presence of autoantibodies against small nuclear ribonucleoprotein epitopes in Chagas' patients' sera", *Parasitol. Res.* 84:796-799 (1998).

Badley et al., "Upregulation of Fas Ligand Expression by Human Immunodeficiency Virus in Human Macrophages Mediates Apoptosis of Uninfected T Lymphocytes", *J. Virology* 70:199-206 (1996).

Barrios et al., "Length of the antibody heavy chain complementarity determining region 3 as a specificity-determining factor", *J. Mol. Recog.* 17:332-338 (2004).

Bateller et al., "Liver fibrosis", *J. Clin. Invest.*, 115(2):209-218 (2005).

Bendele et al., "Combination Benefit of Treatment with the Cytokine Inhibitors Interleukin-1 Receptor Antagonist and PEGylated Soluble

(56) References Cited

OTHER PUBLICATIONS

Tumor Necrosis Factor Receptor Type 1 in Animal Models of Rheumatoid Arthritis", *Arthritis Rheum.* 43(12):2648-2659 (2000).
Bodmer et al., "TRAMP, a Novel Apoptosis-Mediating Receptor with Sequence Homology to Tumor Necrosis Factor Receptor 1 and Fas(Apo-1/CD95)", *Immunity* 6:79-88 (1997).
Boor et al., "Treatment targets in renal fibrosis", *Nephrol. Dial. Transplant.* 22:3391-3407 (2007).
Bose et al., "Problems in using statistical analysis of replacement and silent mutations in antibody genes for determining antigen-driven affinity selection", *Immunology* 116:172-183 (2005).
Boucraut et al., "Anti-TWEAK Monoclonal Antibodies Reduce CNS Immune Cell Infiltration and Severity of Experimental Autoimmune Encephalomyelitis" *Aegean Conference Series*, vol. 12: *Autoimmunity: Mechanisms and Novel Treatments.* Myconos, Greece, Oct. 8-13, 2003; Abstract No. 64, p. 89.
Bowie et al., "Deciphering the Message in Protein Sequences: Tolerance to Amino Acid Substitutions", *Science* 247:1306-1310 (1990).
Branch, "A good antisense molecule is hard to find", *TIBS* 23:45-50 (1998).
Brojatsch et al., "CAR1, a TNFR-Related Protein, Is a Cellular Receptor for Cytopathic Avian Leukosis-Sarcoma Viruses and Mediates Apoptosis", *Cell* 87:845-855 (1996).
Browning et al., "Characterization of Surface Lymphotoxin Forms", *J. Immunol.* 154:33-46 (1995).
Browning et al., "Preparation and Characterization of Soluble Recombinant Heterotrimeric Complexes of Human Lymphotoxins Alpha and Beta", *J. Biol. Chem.* 271:8618-8626 (1996).
Browning et al., "Signaling through the Lymphotoxin Beta Receptor Induces the Death of Some Adenocarcinoma Tumor Lines", *J. Exp. Med.* 183:867-878 (1996).
Browning et al., "Studies on the Differing Effects of Tumor Necrosis Factor and Lymphotoxin on the Growth of Several Human Tumor Lines", *J. Immunol.* 143:1859-1867 (1989).
Browning, J., Second Declaration under 37 CFR 1.132 of Jeffrey Browning, Ph.D. from U.S. Appl. No. 09/245,198, Declaration filed on Jun. 27, 2005.
Bucher et al., "A Generalized Profile Syntax for Biomolecular Sequence Motifs and Its Function in Automatic Sequence Interpretation", Proc. Second International Conference on Intelligent Systems for Molecular Biology. Altman, Brutlag, Karp, Lathrop, Searls (Eds.), pp. 53-61 (1994).
Campbell et al., "Proinflammatory Effects of TWEAK/Fn14 Interactions in Glomerular Mesangial Cells", *J. Immunol.* 176:1889-1898 (2006).
Campbell et al., "The Role of TWEAK/Fn14 in the Pathogenesis of Inflammation and Systemic Autoimmunity", *Frontiers Biosci.* 9:2273-2284 (2004).
Campbell, "The Role of TWEAK/Fn14 Interactions in Antibody Induced Glomerulonephritis", Dissertation, Albert Einstein College of Medicine, Yeshiva University, Nov. 2007. ProQuest, LLC, Ann Arbor, MI, 2009; UMI Microform No. 3340631.
Cardiel et al., "Abetimus Sodium for Renal Flare in Systemic Lupus Erythematosus" *Arthritis & Rheumatism* 58(8):2470-2480 (2008).
Cassiano et al., "Molecular cloning of a novel receptor for TWEAK", *Scand. J. Immunol.* 51 (Suppl. 1):I-III (Abstract 2.2) (2000).
Castro et al., "Fas Modulation of Apoptosis during Negative Selection of Thymocytes" *Immunity* 6:617-627 (1996).
Chaplin et al., "Cytokine regulation of secondary lymphoid organ development", *Curr. Opin. Immunol.* 10:289-297 (1998).
Chicheportiche et al., "Down-Regulated Expression of TWEAK mRNA in Acute and Chronic Inflammatory Pathologies", *Biochem. Biophys. Res. Commun.* 279(1):162-165 (2000).
Chicheportiche et al., "Proinflammatory Activity of TWEAK on Human Dermal Fibroblasts and Synoviocytes: Blocking and Enhancing Effects of Anti-TWEAK Monoclonal Antibodies", *Arthritis Res.* 4(2):126-133 (2002). Epub Nov. 9, 2001.
Chicheportiche et al., "TWEAK, a new secreted ligand in the tumor necrosis factor family that weakly induces apoptosis", *J. Biol. Chem.* 272(51):32401-32410 (Dec. 19, 1997).
Chothia et al., "Structural repertoire of the human $V_H$ segments", *J. Mol. Biol.* 227:799-817 (1992).
Clackson et al., "Making antibody fragments using phage display libraries" *Nature* 352:624-628 (1991).
Clark et al., "Trends in antibody sequence changes during the somatic hypermutation process", *J. Immunol.* 177:333-340 (2006).
Courtenay et al., "Immunisation against heterologous type II collagen induces arthritis in mice", *Nature* 283:666-668 (1980).
Cwirla et al., "Peptides on Phage: A Vast Library of Peptides for Identifying Ligands", *Proc. Natl. Acad. Sci. USA* 87:6378-6382 (1990).
Dallman, "Cytokines and transplantation: Th1/Th2 regulation of the immune response to solid organ transplants in the adult", *Curr. Opin. Immunol.* 7:632-638 (1995).
Darnay et al. ,"Signal Transduction by Tumor Necrosis Factor and Tumor Necrosis Related Ligands and Their Receptors", *Ann. Rheum. Dis.* 58(Suppl. 1):I2-I13 (1999).
David et al., "A study of the structural correlates of affinity maturation: Antibody affinity as a funcetion of chemical interactions, structural plasticity and stability", *Molecular Immunology* 44:1342-1351 (2007).
Davies et al., "Single antibody domains as small recognition units: design and in vitro antigen selection of camelized, human VH domains with improved protein stability", *Protein Eng.* 9(6):531-537 (1996).
De Benedette et al., "Role of 4-1BB Ligand in Costimulation of T Lymphocyte Growth and its Upregulation on M12 B Lymphomas by cAMP", *J. Exp. Med.* 181:985-992 (1995).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody" *J. Immunol.* 169:3076-3084 (2002).
De Wit et al., "Preferential Activation of Th2 Cells in Chronic Graft-versus-Host Reaction", *J. Immunol.* 150(2):361-366 (1993).
Degli-Esposti, "To die or not to die—the quest of the TRAIL receptors", *J. Leukocyte Biol.* 65:535-542 (1999).
Dermer, "Another Anniversary for the War on Cancer", *BioTechnology* 12:320 (1994).
Desplat-Jego et al., "Anti-TWEAK monoclonal antibodies reduce immune cell infiltration in the central nervous system and severity of experimental autoimmune encephalomyelitis", *Clin. Immunol.* 117(1):15-23 (2005).
Desplat-Jégo et al., "TWEAK Is Expressed by Glial Cells, Induces Astrocyte Proliferation and Increases EAE Severity", *J. Neuroimmunol.* 133:116-123 (2002).
Dias et al., "The Role of CXC Chemokines in the Regulation of Tumor Angiogenesis", *Cancer Invest.* 19:732-738 (2001).
Donahue et al., "TWEAK Is an Endothelial Cell Growth and Chemotactic Factor That Also Potentiates FGF-2 and VEGF-A Mitogenic Activity", *Arterioscler. Thromb. Vasc. Biol.* 23:594-600 (2003).
Droz, D., "Clinico-anatomical forms of primary glomerulonephritis", *Rev. Med. Interne* 15(6):390-398 (1994) (Abstract only; article in French).
Durie et al., "Antibody to the Ligand of CD40, gp39, Blocks the Occurrence of the Acute and Chronic Forms of Graft-vs-Host Disease", *J. Clin. Invest.* 94:1333-1338 (1994).
Eck et al., "The Structure of Human Lymphotoxin (Tumor Necrosis Factor-Beta) at 1.9-Å Resolution", *J. Biol. Chem.* 267:2119-2122 (1992).
European Patent Application No. 03721647: Supplementary Partial Search Report, dated Aug. 9, 2005.
European Patent Application No. 06760258: Extended Search Report, including Search Opinion and Supplementary Search Report, dated Jun. 19, 2009.
European Patent Application No. 08104327: Extended Search Report, including Search Opinion, dated Feb. 6, 2009.
European Patent Application No. 10181803: Extended Search Report, including Search Opinion, dated Jul. 6, 2012.

(56) References Cited

OTHER PUBLICATIONS

European Patent Application No. 10181810: Extended Search Report, including Search Opinion, dated Jul. 6, 2012.

Falk et al., "Expression of the APO-1 Antigen in Burkitt Lymphoma Cell Lines Correlates with a Shift Towards a Lymphoblastoid Phenotype", *Blood* 79:3300-3306 (1992).

Feng et al., "The Fn14 Immediate-Early Response Gene Is Induced During Liver Regeneration and Highly Expressed in Both Human and Murine Hepatocellular Carcinomas", *Am. J. Pathol.* 156(4):1253-1261 (2000).

Flynn et al., "CD4 T Cell Cytokine Differentiation: The B Cell Activation Molecule, OX40 Ligand, Instructs CD4 T Cells to Express Interleukin 4 and Upregulates Expression of the Chemokine Receptor, Blr-1", *J. Exp. Med.* 188:297-304 (1998).

Fox, D., "Biological Therapies: A Novel Approach to the Treatment of Autoimmune Disease", *Am. J. Med.* 99:82-88 (1995).

Fujimoto et al., "Interleukin-6 Blockade Suppresses Autoimmune Arthritis in Mice by the Inhibition of Inflammatory Th17 Responses", *Arthritis & Rheumatism* 58:3710-3719 (2008).

Funakoshi et al., "Inhibition of Human B-Cell Lymphoma Growth by CD40 Stimulation", *Blood* 83:2787-2794 (1994).

Galle et al., "Involvement of the CD95 (APO-1/Fas) Receptor and Ligand in Liver Damage", *J. Exp. Med.* 182:1223-1230 (1995).

Gauchat et al., "Human CD40-Ligand: Molecular Cloning, Cellular Distribution and Regulation of Expression by Factors Controlling IgE Production", *FEBS Lett.* 315:259-266 (1993).

GenBank Acc. No. AAB49141, "Anti-DNA immunoglobulin heavy chain IgG [*Mus musculus*]" (1996).

Genentech, Inc., Full Prescribing Information for Actrema (Jan. 2010) (24 pages).

Gleichmann et al., "A systemic lupus erythematosus (SLE)-like disease in mice induced by abnormal T-B cell cooperation. Preferential formation of autoantibodies characteristic of SLE", *Eur. J. Immunol.* 12:152-159 (1982).

Grewal et al., "The CD40 Ligand. At the Center of the Immune Universe?", *Immunol. Res.* 16:59-70 (1997).

Grewal et al., "The Role of CD40 Ligand in Costimulation and T-Cell Activation", *Immunol. Rev.* 153:85-106 (1996).

Gruss et al., "Pleiotrophic Effects of the CD30 Ligand on CD30-Expressing Cells and Lymphoma Cell Lines", *Blood* 83:2045-2056 (1994).

Gruss et al., "Tumor Necrosis Factor Ligand Superfamily: Involvement in the Pathology of Malignant Lymphomas" *Blood* 85:3378-3404 (1995).

Hahm et al., "TWEAK overexpression induces hyperplasia in liver and kidney", *FASEB J.* 17(4-5):Abstract No. 471.5 (2003).

Han et al., "Identification of Differentially Expressed Genes in Pancreatic Cancer Cells Using cDNA Microarray", *Cancer Research* 62:2890-2896 (May 15, 2002).

Han et al., "Overexpression of FN14/TEAK receptor in pancreatic cancer", *Proc. Am. Assoc. Cancer Res. Annual Meeting* 46(Suppl. S):Abstract No. 2363 (Apr. 18, 2005).

*Harrison's Principles of Internal Medicine*, 2005; pp. 1960-1963.

Hess et al., "A Novel Function of CD40: Induction of Cell Death in Transformed Cells", *J. Exp. Med.* 183:159-167 (1996).

Hillier, L. et al., "The Wash U-Merck EST project yy19a08.s1 *Homo sapiens* cDNA clone 2716703", EMBL Database Entry HS070272, Accesion No. N35070 (Jan. 19, 1996).

Hillier, L. et al., "The WashU-Merck EST project yy19a08.s1 *Homo sapiens* cDNA clone 1547425", EMBL Database Entry HS379117, Accession No. R55379 (May 28, 1995).

Ho et al., "Soluble Tumor Necrosis Factor-Like Weak Inducer of Apoptosis Overexpression in HEK293 Cells Promotes Tumor Growth and Angiogenesis in Athymic Nude Mice", *Cancer Research* 64:8968-8972 (Dec. 15, 2004).

Ike et al., "Solid Phase Synthesis of Polynucleotides. VIII. Synthesis of Mixed Oligodeoxyribonucleotides by the Phosphotriester Solid Phase Method", *Nucl. Acids Res.* 11:477-488 (1983).

International Search Report issued in International Patent Application No. PCT/US00/01044; Date of Mailing: Jun. 6, 2000.

International Preliminary Examination Report issued in International Patent Application No. PCT/US03/11350; Date of Mailing: Nov. 23, 2004.

International Search Report issued in International Patent Application No. PCT/US03/11350; Date of Mailing: Mar. 10, 2004.

International Search Report and Written Opinion issued in International Patent Application No. PCT/US06/022830; Date of Mailing: Jan. 26, 2007.

International Search Report and Written Opinion issued in International Patent Application No. PCT/US06/19706; Date of Mailing: Oct. 9, 2007.

Jain et al., "A Novel Role for Tumor Necrosis Factor Like Weak Inducer of Apoptosis (TWEAK) in the Development of Cardiac Dysfunction and Failure", *Circulation* 119:2058-2068, with supplemental material (2009).

Jakubowski et al., "Dual role for TWEAK in angiogenic regulation", *J. Cell Sci.* 115(Pt. 2):267-274 (Jan. 15, 2002).

Jakubowski et al., "TWEAK induces liver progenitor cell proliferation", *J. Clin. Invest.* 115(9):2330-2340 (Sep. 2005).

Jakubowski, A. et al., "TWEAK Synergizes with Basis Fibroblast Growth Factor to Induce Endothelial Cell Proliferation, Migration and Lumen Morphogenesis", *Scand. J. Immunol.* 51(Suppl. 1):62, Abstract 1.30 (2000).

Jones et al., "Immunospecific reduction of antioligonucleotide antibody-forming cells with a tetrakis-oligonucleotide conjugate (LJP 394), a therapeutic candidate for the treatment of lupus nephritis" *J. Med. Chem.* 38(12):2138-2144 (1995) (Abstract only).

Juengst, "What next for human gene therapy", *BMJ* 326:1410-1411 (2003).

Kaduka et al., "TWEAK Mediates Anti-Tumor Effect of Tumor-Infiltrating Macrophage", *Biochem. Biophys. Res. Commun.* 331:384-390 (2005).

Kalled et al., "Anti-CD40 Ligand Antibody Treatment of $SNF_1$ Mice with Established Nephritis: Preservation of Kidney Function", *J. Immunol.* 160:2158-2165 (1998).

Kamata et al., "Involvement of TNF-Like Weak Inducer of Apoptosis in the Pathogenesis of Collagaen-Induced Arthritis" *J. Immunol.* 177:6433-6439 (2006).

Kaplan et al., "Th2 Lymphocytes Kill Antigen Presenting Macrophages Through a TWEAK Dependant Pathway", *J. Invest. Med.* 46(7):287A (1998).

Kaplan et al., "The Apoptotic Ligands TRAIL, TWEAK, and Fas Ligand Mediate Monocyte Death Induced by Autologous Lupus T Cells", *J. Immunol.* 169:6020-6029 (2002).

Kaplan et al., "TRAIL (Apo2 Ligand) and TWEAK (Apo3 Ligand) Mediate $CD4^+0$ T Cell Killing of Antigen-Presenting Macrophages", *J. Immunol.* 164:2897-2904 (2000).

Katsikis et al., "Fas Antigen Stimulation Induces Marked Apoptosis of T Lymphocytes in Human Immunodeficiency Virus-infected Individuals", *J. Exp. Med.* 181:2029-2036 (1995).

Kawakita et al., "Functional expression of TWEAK in human hepatocellular carcinoma: possible implication in cell proliferation and tumor angiogenesis", *Biochem. Biophys. Res. Commun.* 318:726-733 (2004).

Kirk et al., "CTLA4-Ig and anti-CD40 ligand prevent renal allograft rejection in primates", *Proc. Natl. Acad. Sci. USA* 94:8789-8794 (1997).

Kobrin et al., "A V region mutation in a phosphocholine-binding monoclonal antibody results in loss of antigen binding", *J. Immunol.* 146:2017-2020 (1991).

Kornek et al., "Multiple Sclerosis and Chronic Autoimmune Encephalomyelitis. A Comparative Quantitative Study of Axonal Injury in Active, Inactive, and Remyelinated Lesions", *Am. J. Pathol.* 157(1):267-276 (2000).

Krenger et al., "Graft-versus-Host Disease and the Th1/Th2 Paradigm", *Immunol. Res.* 15:50-73 (1996).

Lee et al., "T Cell Receptor-dependent Cell Death of T Cell Hybridomas Mediated by the CD30 Cytoplasmic Domain in Association with Tumor Necrosis Factor Receptor-Associated Factors", *J. Exp. Med.* 183:669-674 (1996).

Lennon et al., "The I.M.A.G.E. Consortium: An Integrated Molecular Analysis of Genomes and Their Expression", *Genomics* 33:151-152 (Apr. 1996) with Medline Abstract page.

(56) References Cited

OTHER PUBLICATIONS

Lenschow et al., "Differential Effects of Anti-B7-1 and Anti-B7-2 Monoclonal Antibody Treatment on the Development of Diabetes in the Nonobese Diabetic Mouse", *J. Exp. Med.* 181:1145-1155 (1995).
Lin et al., "Very late antigen 4 (VLA4) antagonists as anti-inflammatory agents", *Curr. Opin. Chem. Biol.* 2:453-457 (1998).
Lund et al., "Human FcγRI and FcγRII interact with distinct but overlapping sites on human IgG", *J. Immunol.* 147:2657-2662 (1991).
Lynch et al., "TWEAK Induces Angiogenesis and Proliferation of Endothelial Cells", *J. Biol. Chem.* 274(13):8455-8459 (1999).
Lynch et al., "TWEAK Induces Proliferation in Endothelial Cells and Substitutes for EGF and Hydrocortisone in Culture", *J. Interferon Cytokine Res.* 18:A-46, Abstract 2.16 (1998).
Mackay et al., "Turning off follicular dendritic cells", *Nature* 395:26-27 (1998).
Markan et al., "Up regulation of the GRP-78 and GADD-153 and down regulation of Bcl-2 proteins in primary glomerular diseases: a possible involvement of the ER stress pathway in glomerulonephritis", *Mol. Cell Biochem.* 324:131-138 (2009).
Marra et al., "The WashU-HHMI Mouse EST project. my18d09.r1 Barstead mouse heart MPLRB3 Mus musculus cDNA clone 696209 5'" GenBank Database Accession No. AA221610 (Feb. 15, 1997).
Marsters et al., "Identification of a ligand for the death-domain-containing receptor Apo3", *Current Biology* 8:525-528 (1998).
Martin-Villalba et al., "Therapeutic Neutralization of CD-95-Ligand and TNF Attenuates Brain Damage in Stroke", *Cell Death Diff.* 8:679-686 (2001).
Meighan-Mantha et al., "The Mitogen-inducible *Fn14* Gene Encodes a Type I Transmembrane Protein that Modulates Fibroblast Adhesion and Migration", *J. Biol. Chem.* 274(46):33166-33176 (Nov. 12, 1999).
Michaelson et al., "Tweak induces mammary epithelial branching morphogenesis", *Oncogene* 24:2613-2624 (2005).
Miller et al., "Genetic Studies of the *lac* Repressor. IX. Generation of Altered Proteins by the Suppression of Nonsense Mutations", *J. Mol. Biol.* 131:191-222 (1979).
Mohan et al., "Interaction Between CD40 and Its Ligand gp39 in the Development of Murine Lupus Nephritis", *J. Immunol.* 154:1470-1480 (1995).
Montgomery et al., "Herpes Simplex Virus-1 Entry into Cells Mediated by a Novel Member of the TNF/NGF Receptor Family", *Cell* 87:427-436 (1996).
Morgan et al., "The N-terminal end of the $C_H2$ domain of chimeric human IgG1 anti-HLA-DR is necessary for C1q, FcγRI and FcγRIII binding", *Immunology* 86:319-324 (1995).
Morris et al., "Experimental Induction of Systemic Lupus Erythematosus by Recognition of Foreign Ia", *Clin. Immunol. Immunopathol.* 57:263-273 (1990).
Mueller, A.M. et al., "Targeting fibroblast growth-factor-inducible-14 signaling protects from chronic relapsing experimental autoimmune encephalomyelitis", *J. Neuroimmunol.* 159(1-2):55-65 (2005).
Murphy, "Revisiting graft-versus-host disease models of autoimmunity: new insights in immune regulatory processes", *J. Clin. Invest.* 106(6):745-747 (2000).
Nagata, S., "Apoptosis by Death Factor" *Cell* 88:355-365 (1997).
Nakaya et al., "Regulation of Asialoglycoprotein Receptor Synthesis by Inflammation-Related Cytokines in HepG2 Cells", *J. Gastroenterol.* 29:24-30 (1994).
Nakayama et al., "Characterization of murine TWEAK and its receptor (Fn14) by monoclonal antibodies", *Biochem. Biophys. Res. Commun.* 306(4):819-825 (2003).
Nakayama et al., "Fibroblast Growth Factor-Inducible 14 Mediates Multiple Pathways of TWEAK-Induced Cell Death", *J. Immunol.* 170:341-348 (2003).
Nakayama et al., "Involvement of TWEAK in Interferon γ-stimulated Monocyte Cytotoxicicity", *J. Exp. Med.* 192(9):1373-1379 (2000).
Neutra et al., "Intestinal Epithelium: A Model System for Study of Cell Differentiation and Polarized Cell Functions", in *Functional Epithelia Cells in Culture.* Liss (ed.), 1989; pp. 363-398.
Ngo et al., in *The Protein Folding Problem and Tertiary Structure Prediction.* K. Merz Jr. and S. Legrand (Eds.) Birkhauser, Boston, 1994; pp. 433 and 492-495.
Orkin et al., Report and Recommendations of the Panel to Assess the NIH Investment in Research on Gene Therapy (Dec. 7, 1995).
Paul, "Fv Structure and Diversity in Three Dimensions", in *Fundamental Immunology*, 3rd. edition. New York: Raven Press, 1993; pp. 292-295.
Pepper et al., "Biphasic effect of transforming growth factor-$\beta_1$ on in vitro angiogenesis", *Exp. Cell Res.* 204(2):356-363 (Feb. 1993).
Perper et al., "TWEAK is a novel arthritogenic mediator", *J. Immunol.* 177(4):2610-2620 (Aug. 15, 2006).
Pitti et al., "Induction of Apoptosis by Apo-2 Ligand, a New Member of the Tumor Necrosis Factor Cytokine Family", *J. Biol. Chem.* 271:12687-12690 (1996).
Plowman et al., "Human Tumor Xenograft Models in NCI Drug Development", in *Anticancer Drug Development Guide: Preclinical Screening, Clinical Trials and Approval.* B. Teicher (ed.), Humana Press Inc., Totown, 1997; pp. 101-125.
Portanova et al., "Lupus-like autoimmunity in murine graft-versus-host disease", *Concepts Immunopathol.* 6:119-140 (1988).
Portolano et al., "Lack of promiscuity in autoantigen-specific H and L chain combinations as revealed by human H and L chain 'Roulette'" *J. Immunol.* 150(3):880-887 (1993).
Potrovita et al., "Tumor Necrosis Factor-Like Weak Inducer of Apoptosis-Induced Neurodegeneration", *J. Neurosci.* 24(38):8237-8244 (Sep. 22, 2004).
Potrovita et al., "TWEAK—A Regulator of Neuronal Cell Death", *Naunyn-Schmiedeberg's Archives of Pharmacology* 369(Suppl. 1):R12, Abstr. 48 (Mar. 9, 2004).
Putterman et al., "Tweak Blockade Improves Kidney Disease in Lupus-Prone Mice: A Novel Approach to the Treatment of Lupus Nephritis?", Annual Meeting of Professional Research Scientists, Washington, D.C., Apr. 17-21, 2004. *FASEB J.*, 18(5), Experimental Biology 2004, Abstracts Part II:A839, Abstract No. 562.27 (2004).
Roberts et al., "Directed Evolution of a Protein: Selection of a Potent Neutrophil Elastase Inhibitors Displayed on M13 Fusion Phage", *Proc. Natl. Acad. Sci. USA* 89:2429-2433 (1992).
Romano et al., "Latest developments in gene transfer technology: achievements, perspectives, and controversies over therapeutic applications", *Stem Cells* 18:19-39 (2000).
Rosenberg et al., "Gene therapist, heal thyself", *Science* 287:1751 (2000).
Rovin et al., "Urine chemokines as biomarkers of human systemic lupus erythematosus activity", *J. Am. Soc. Nephrol.* 16:467-473 (2005).
Rudikoff et al., "Single amino acid substitution altering antigen-binding specificity", *Proc. Natl. Acad. Sci. USA*, 79(6):1979-1983 (1982).
Rudinger, "Characteristics of the amino acids as components of a peptide hormone sequence", in *Peptide Hormones.* J.A. Parsons (Ed.), University Park Press, Baltimore, MD, 1976; pp. 1 and 6 (1976).
Rus et al., "Kinetics of Th1 and Th2 Cytokine Production During the Early Course of Acute and Chronic Murine Graft-Versus-Host Disease", *J. Immunol.* 155:2396-2406 (1995).
Ruuls et al., "The Length of Treatment Determines Whether IFN-Beta Prevents or Aggravates Experimental Autoimmune Encephalomyelitis in Lewis Rats", *J. Immunol.* 157:5721-5731 (1996).
Saas et al., "TWEAK Stimulation of Astrocytes and the Proinflammatory Consequences", *GLIA* 32(1):102-107 (2000).
Saemann et al., "Urinary tract infection in renal transplant recipients" *Eur. J. Clin. Invest.* 38(Suppl. 2):58-65 (2008).
Scamurra et al., "Ig heavy chain variable region VH3 family [*Homo sapiens*]", NCBI database Accession No. GI:33318898, GenBank Accession No. AAQ05352 (2002).
Schneider et al., "TWEAK Can Induce Cell Death via Endogenous TNF and TNF Receptor 1", *Eur. J. Immunol.* 29(6):1785-1792 (1999).
Semov et al., "Alterations in TNF- and IL-related Gene Expression in Space-flown WI38 Human Fibroblasts", *FASEB J.* 16(8):899-901 (2002).

(56) References Cited

OTHER PUBLICATIONS

Shepard et al., "Monoclonal Antibody Therapy of Human Cancer: Taking the HER2 Protooncogene to the Clinic", *J. Clin. Immunol.* 11:117-127 (1991).
Smith et al., "CD30 Antigen, a Marker for Hodgkin's Lymphoma, Is a Receptor Whose Ligand Defines an Emerging Family of Cytokines with Homology to TNF", *Cell* 73:1349-1360 (1993).
Somia et al., "Gene therapy: trials and tribulations", *Nature Reviews Genetics* 1:91-99 (2000).
Song et al., "A single amino acid change (Asp 53 →4 Ala53) converts Survivin from anti-apoptotic to pro-apoptotic", *Mol. Biol. Cell* 15:1287-1296 (Mar. 2004).
Steinman et al., "Virtues and Pitfalls of EAE for the Development of Therapies for Multiple Sclerosis", *Trends Immunol.* 26(11):565-571 (2005).
Steinman, L., "Optic Neuritis, a New Variant of Experimental Encephalomyelitis, a Durable Model for All Seasons, Now in Its Seventieth Year", *J. Exp. Med.* 197(9):1065-1071 (2003).
Stryer et al., in *Biochemistry*, 3rd Ed., W.H. Freeman and Co.: New York, 1988; pp. 31-33.
Stuber et al., "The T Cell-B Cell Interaction via OX40-OX40L Is Necessary for the T Cell-dependent Humoral Immune Response", *J. Exp. Med.* 183:979-989 (1996).
Sytwu et al., "The Roles of Fas/APO-1 (CD95) and TNF in Antigen-Induced Programmed Cell Death in T Cell Receptor Transgenic Mice", *Immunity* 5:17-30 (1996).
Takagi et al, "Blockage of Interleukin-6 Receptor Ameliorates Joint Disease in Murine Collagen-Induced Arthritis", *Arthritis & Rheumatism* 41:2117-2121 (1998).
Tannenbaum et al., "The CXC Chemokines IP-10 and Mig are Necessary for IL-12-Mediated Regression of the Mouse RENCA Tumor", *J. Immunol.* 161:927-932 (1998).
Tartaglia et al., "The Two Different Receptors for Tumor Necrosis Factor Mediate Distinct Cellular Responses", *Proc. Natl. Acad. Sci. USA* 88:9292-9296 (1991).
Techman, A., "Biogen Idec and University of Adelaide Find TWEAK Is a Novel Arthritogenic Mediator; Potential New Pathway in Rheumatoid Arthritis and Osteoarthritis Disease Process" *Musckuloskeletal Report*, Aug. 16, 2006, pp. 1-2 [online]. Retrieved from the Internet, www.mskreport.com, Aug. 2, 2010.
Theien et al., "Discordant effects of anti-VLA-4 treatment before and after onset of relapsing experimental autoimmune encephalomyelitis", *J. Clin. Invest.* 107:995-1006 (2001).
Tibbetts et al., "Cardiac Antigen-Specific Autoantibody Production Is Associated with Cardiomyopathy in *Trypanosome cruzi*-Infected Mice", *J. Immunol.* 152:1493-1499 (1994).
Tomlinson et al., "The repertoire of human germline $V_H$ sequences reveals about fifty groups of $V_H$ segments with different hypervariable loops", *J. Mol. Biol.* 227:776-798 (1992).
Tomlinson et al., "The structural repertoire of the human Vκ domain" *EMBO J.* 14:4628-4638 (1995).
Toogood et al., "The Immune Response Following Small Bowel Transplantation", *Transplantation* 62(6):851-855 (1996).
Tran et al., "The Human Fn14 Receptor Gene Is Up-Regulated in Migrating Glioma Cells in Vitro and Overexpressed in Advanced Glial Tumors", *Am. J. Pathol.* 162(4):1313-1321 (Apr. 2003).
Tran et al., "The Tumor Necrosis Factor-like Weak Inducer of Apoptosis (TWEAK)-Fibroblast Growth Factor-inducible 14 (Fn14) Signaling System Regulates Glioma Cell Survival via NFκB Pathway Activation and $BCL-X_L$/BCL-W Expression", *J. Biol. Chem.* 280(5):3483-3492 (Feb. 4, 2005).
Trauth et al., "Monoclonal Anitbody-Mediated Tumor Regression by Induction of Apoptosis", *Science* 245:301-305 (1989).
Trentham et al., "Autoimmunity to Type II Collagen: An Experimental Model of Arthritis", *J. Exp. Med.* 146:857-868 (1977).
Tschetter et al., "Progression from Acute to Chronic Disease in a Murine Parent-into-$F_1$ Model of Graft-Versus-Host Disease" *J. Immunol.* 165:5987-5994 (2000).
U.S. Appl. No. 09/169,104 by Ashkenazi et al., filed Oct. 9, 1998.
U.S. Patent Interference No. 105,513 entered on Nov. 15, 2006.
U.S. Patent Interference No. 105,513, Paper 106, Memorandum Opinion and Order, Decision on Motions.
U.S. Patent Interference No. 105,513, Paper 107, Decision—Bd. R. 125, Decision on Browning Misc. Motion 4 for Sanctions.
U.S. Patent Interference No. 105,513, Paper 108, Judgment, Preliminary Motions—Bd. R. 127.
Uchiyama et al., "Tocilizumab, a Humanized Anti-interleukin-6 Receptor Antibody, Ameliorates Joint Swelling in Established Monkey Collagen-Induced Arthritis", *Biol. Pharm. Bull.* 31(6):1159-1163 (2008).
Verma et al., "Gene therapy—promises, problems and prospect", *Nature* 18:239-242 (1997).
Via "Advances in lupus stemming from the parent-into-F1 model", *Trends Immunol.* 31:236-245 (2010).
Via et al., "Role of cytotoxic T lymphocytes in the prevention of lupus-like disease occurring in a murine model of graft-vs-host disease", *J. Immunol.* 139:1840-1849 (1987).
Wada et al., "Detection of urinary interleukin-8 in glomerular diseases" *Kidney International* 46:455-460 (1994).
Ward et al., "Blocking of adhesion molecules in vivo as anti-inflammatory therapy", *Ther. Immunol.* 1(3):165-171 (1994).
*Webster's II New Riverside University Dictionary*, "Preventing", Boston, Mass.: Houghton Mifflin Co., 1994; p. 933.
Weisman et al., "Reduction in circulating dsDNA antibody titer after administration of LJP 394" *J. Rheumatol.* 24(2):314-318 (1997) (Abstract only).
Wiley et al., "A Novel TNF Receptor Family Member Binds TWEAK and Is Implicated in Angiogenesis", *Immunity* 15:837-846 (2001).
Wiley et al., "Identification and Characterization of a New Member of the TNF Family that Induces Apoptosis", *Immunity* 3:673-682 (1995).
Wiley et al., "TWEAK, a member of the TNF superfamily, is a multifunctional cytokine that binds the TweakR/Fn14 receptor", *Cytokine & Growth Factor Reviews* 14:241-249 (2003).
Williamson et al., "IL-12 Is a Central Mediator of Acute Graft-Versus-Host Disease in Mice", *J. Immunol.* 157(2):689-699 (1996).
Winkles et al., "Role of TWEAK and Fn14 in tumor biology", *Frontiers in Bioscience* 12:2761-2771 (Jan. 1, 2007).
Winkles et al., "TWEAK and Fn14: New molecular targets for cancer therapy?", *Cancer Letters* 235:11-17 (2006).
Written Opinion issued in International Patent Application No. PCT/US00/01044; Date of Mailing: Oct. 30, 2000.
Wuthrich et al., "Autoimmune tubulointerstitial nephritis: insight from experimental models", *Exp. Nephrol.* 6(4):288-293 (1998).
Yonehara et al., "A Cell-Killing Monoclonal Antibody (ANTI-Fas) to a Cell Surface Antigen Co-Downregulated with the Receptor of Tumor Necrosis Factor", *J. Exp. Med.* 169:1747-1756 (1989).
Zhao et al., "Different Gene Expression Patterns in Invasive Lobular and Ductal Carcinomas of the Breast", *Mol. Biol. Cell* 15:2523-2536 (Jun. 2004).
Zhao et al., "TWEAK/Fn14 Interactions Are Instrumental in the Pathogenesis of Nephritis in the Chronic Graft-versus-Host Model of Systemic Lupus Erythematosis", *J. Immunol.* 179:7949-7958 (2007).
Zhu et al., "Inhibition of tumor growth and metastasis by targeting tumor-associated angiogenesis with antagonists to the receptors of vascular endothelial growth factor", *Investigational New Drugs* 17:195-212 (1999).

\* cited by examiner

A. Right atrial and ventricular thrombosis and dilation FL-Tweak Transgenic
B Normal heart. H&E.

Biliary Duct and Oval Cell Hyperplasia in Liver of TWEAK Tg Mice

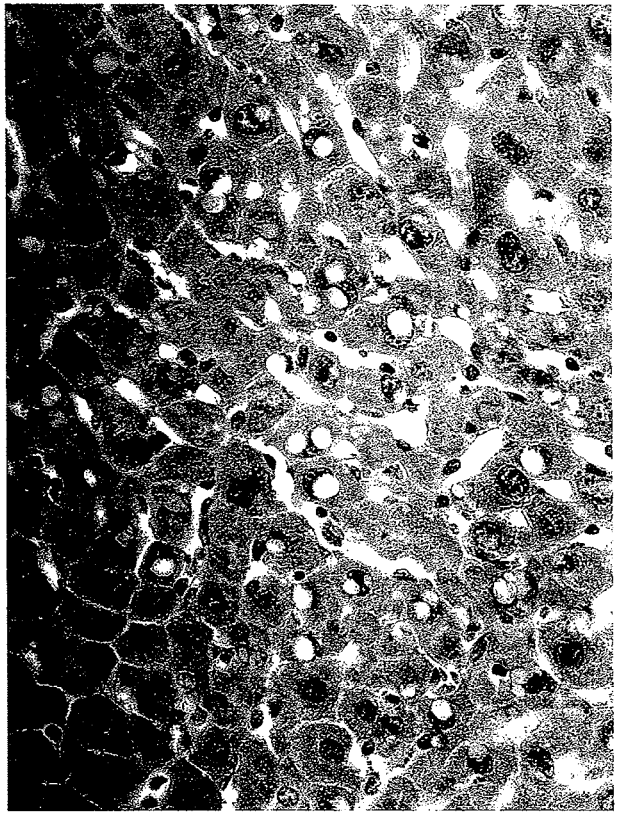
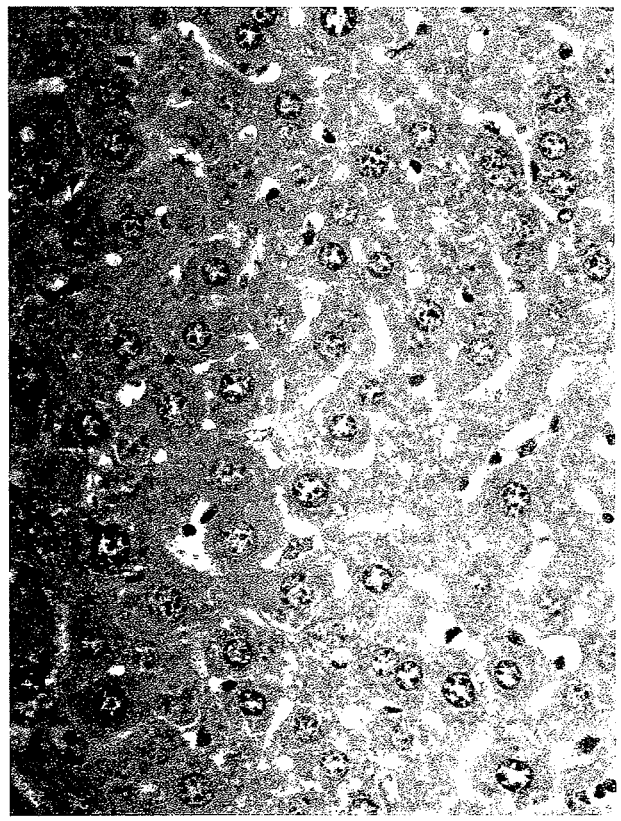
FIG. 6

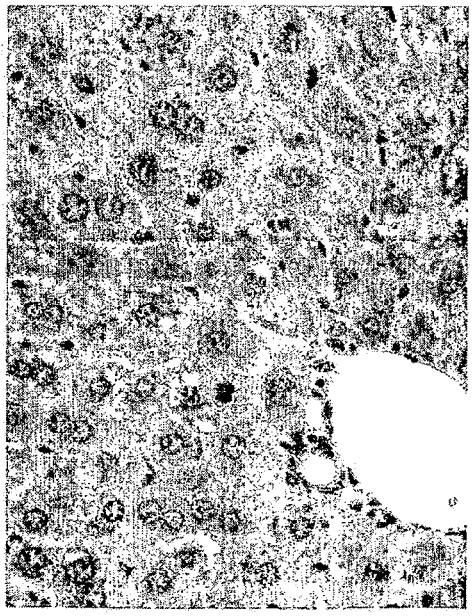
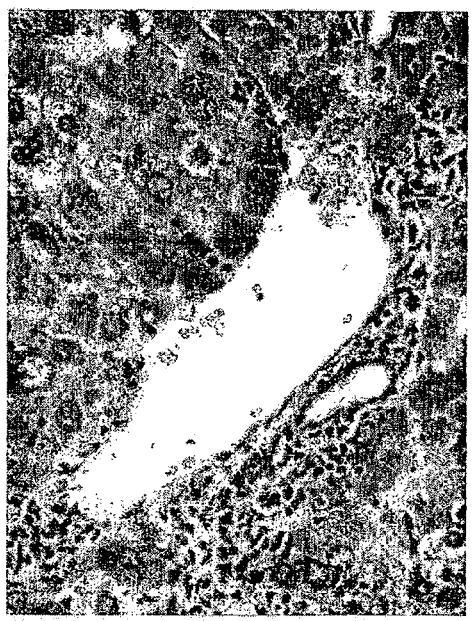
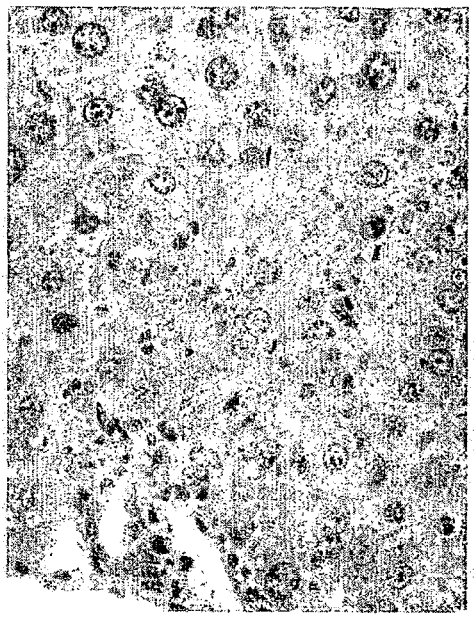
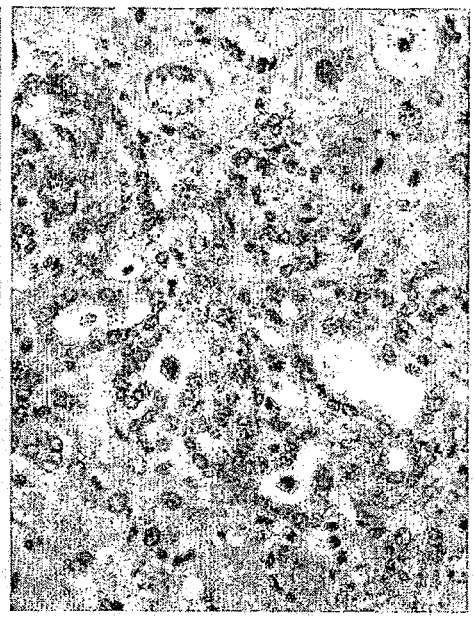
FIG. 8
TWEAK Induces Hepatocyte Death and Ductal Hyperplasia in Adult Mice A. H&E staining of liver section
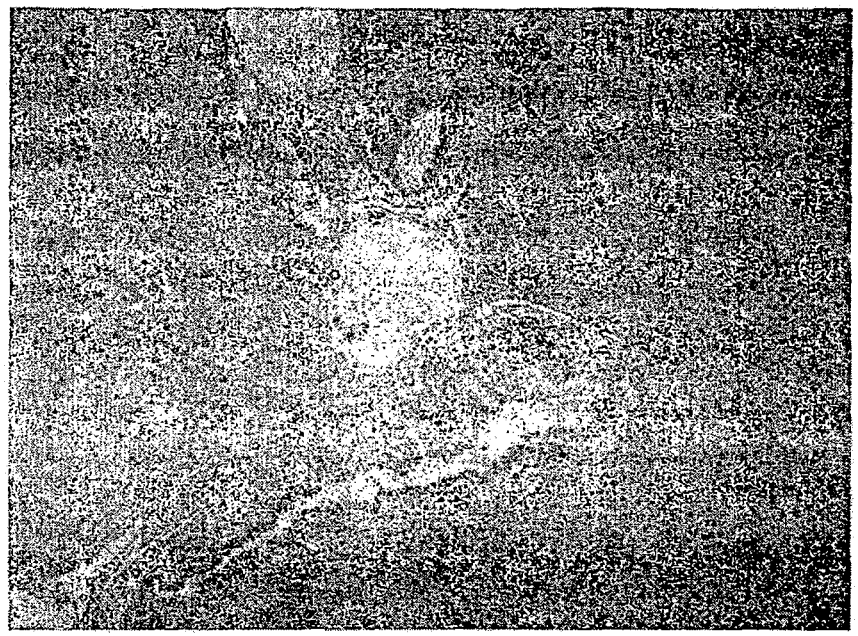
B. FN14 anti-sense mRNA in situ hybridization
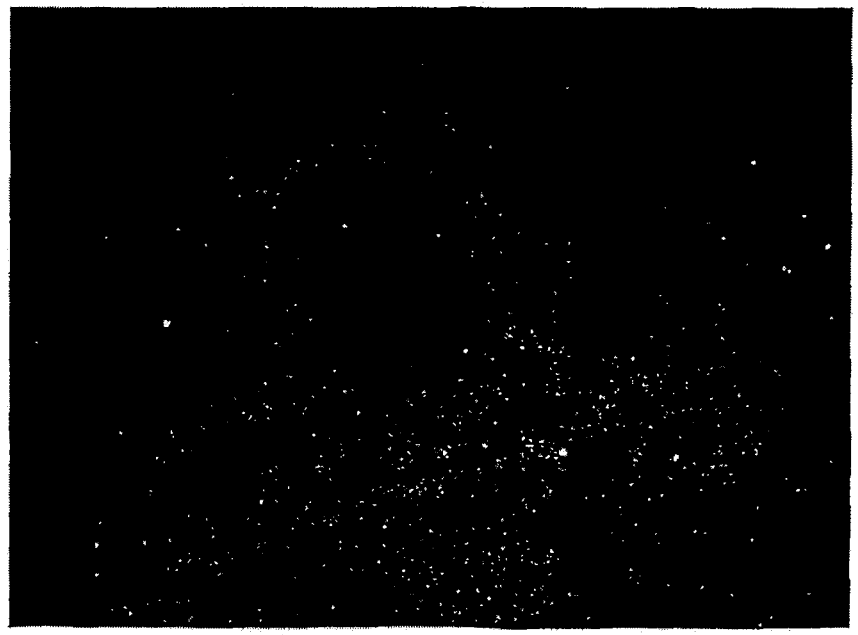
FIG. 10

A. Glomerular nephropathy with basophilia of adjacent proximal tubular epithelium.
B. Segmental mesangial hypercellularity, hypertrophy of capsular epithelia and mild capsular thickening. H&E.

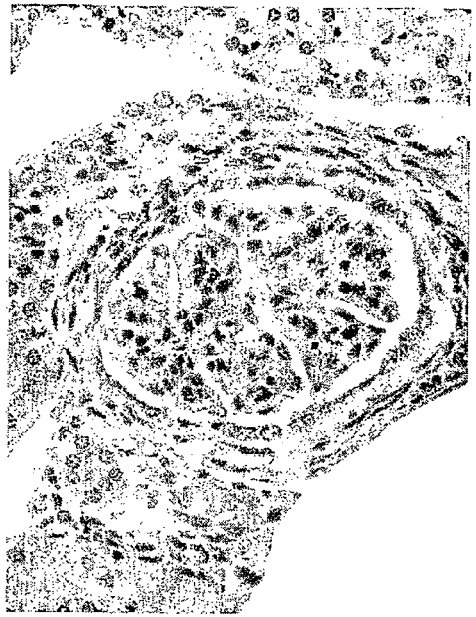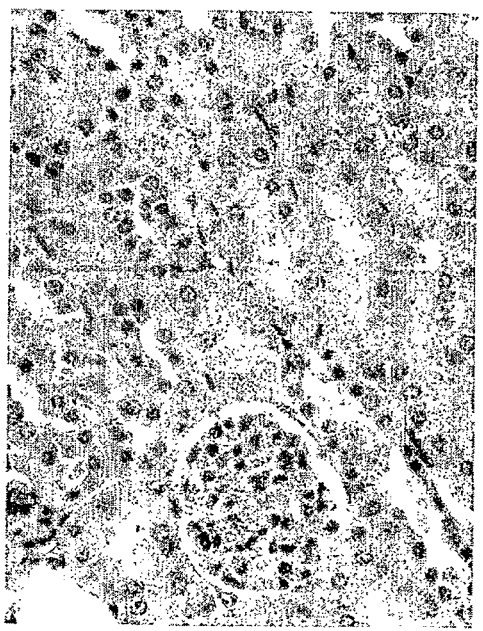
FIG. 15

Role of TWEAK in Lung: Inflammation in TWEAK Tg Mice

Granulomatous/lymphohistiocytic inflammation. A. FL-TWEAK Tg mouse backcrossed 4x to B6, B. s TWEAK Tg mouse H&E.

No treatment 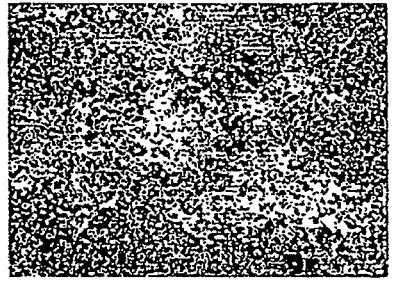
hcD40L-Flag(100ng/ml) 
hTweak-Flag (100ng/ml) 
Recombinant hTweak (100ng/ml) 
Fc-hTweak (100 ng/ml) 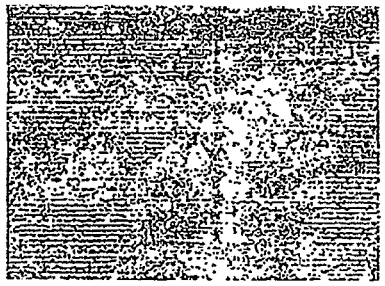
Fc-hTweak + AB.G11 (10 µg/ml) 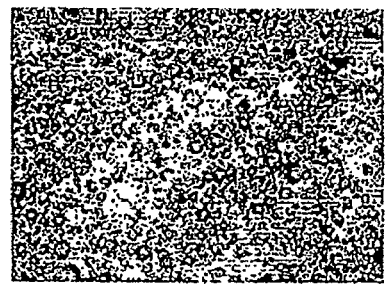
Fig. 23

US 9,011,859 B2

METHODS FOR TREATING TWEAK-RELATED CONDITIONS

CROSS-REFERENCE TO RELATED APPLICATIONS

This application is a continuation of U.S. patent application Ser. No. 13/179,096, filed Jul. 8, 2011, now abandoned, which is a continuation of U.S. patent application Ser. No. 12/417,755, filed Apr. 3, 2009, now U.S. Pat. No. 8,506,958, which is a continuation of U.S. patent application Ser. No. 10/510,804, filed Sep. 13, 2005, now abandoned, which is a national stage entry of International Application No. PCT/US03/11350, filed Apr. 9, 2003, now published as WO 03/086311 on Oct. 23, 2003, and claims the benefit of U.S. Provisional Application No. 60/371,611, filed Apr. 9, 2002, all of which are incorporated herein by reference in their entirety.

TECHNICAL FIELD OF THE INVENTION

The present invention relates to methods and agents for the treatment of TWEAK-related conditions, including cardiac, liver, kidney, lung, adipose, skeletal muscle, neural, bone, cartilage, skin, gastrointestinal, pancreatic, reproductive organ and connective tissue diseases. The invention also relates to methods for identifying TWEAK agonists or antagonists for the treatment of TWEAK-related conditions. Additionally, the invention relates to transgenic animals that express an exogenous DNA encoding a TWEAK polypeptide, or fragments, analogs, or muteins thereof and methods for using such animals to identify TWEAK agonists or antagonists. The invention further relates to methods for diagnosing a disease based on TWEAK expression. The invention also relates to methods for affecting cellular proliferation or differentiation of progenitor cells using TWEAK polypeptides, agonists or antagonists.

BACKGROUND OF THE INVENTION

Members of the Tumor Necrosis Factor (TNF) family of ligands, so named for their structural similarity to TNF-α, are key components in diverse processes, such as inflammatory responses, cellular immunity and apoptosis. TNF ligands may act locally as type II membrane-bound proteins through direct cell-to-cell contact or as secreted proteins having autocrine, paracrine or endocrine functions. TNF family members bind TNF receptor (TNF-R) family members via their C-terminal extracellular domain. Various TNF family members include TNF, lymphotoxins (LT), Fas, CD27, CD30, CD40, 4-1BB, OX-40, TRAMP, CAR-1, TRAIL, GITR, HVEM, osteoprotegrin, NGF, TRAIN, Kay (BAFF), APRIL and TWEAK (TNF relatedness and weak ability to induce cell death).

A defining feature of this family of cytokine receptors is found in the cysteine rich extracellular domain, initially revealed by the molecular cloning of two distinct TNF receptors. This family of genes encodes glycoproteins characteristic of Type I transmembrane proteins having an extracellular ligand binding domain, a single membrane spanning region and a cytoplasmic region involved in activating cellular functions. The cysteine-rich ligand binding region exhibits a tightly knit disulfide linked core domain, which, depending upon the particular family member, is repeated multiple times. Most receptors have four domains, although there may be as few as one, or as many as six.

TNF family members play a role in the regulation of the immune system, controlling cell survival and differentiation, as well as acute host defense systems, such as inflammation. Continued efforts in the art to manipulate members of the TNF family for therapeutic benefit may provide unique means to control disease. For instance, some of the ligands of this family can directly induce the apoptotic death of many transformed cells, e.g., LT, TNF, Fas ligand and TRAIL. Fas and possibly TNF and CD30 receptor activation can induce cell death in nontransformed lymphocytes which may display an immunoregulatory function.

The ability to induce programmed cell death is an important and well-studied feature of several members of the TNF family. Fas mediated apoptosis appears to play a role in the regulation of autoreactive lymphocytes in the periphery and possibly the thymus. Also, the TNF and CD30 systems have been implicated in the survival of T cells and large cell anaplastic lymphoma lines. Death in this cell line in response to TNF, Fas or LT-β receptor signaling has features of apoptosis.

The TNF family of ligands may be categorized into three groups based on their ability to induce cell death. First, TNF, Fas ligand and TRAIL can efficiently induce cell death in many lines and their receptors most likely have good canonical death domains. Presumably the ligand to DR-3 (TRAMP/WSL-1) would also fall into this category. Next there are those ligands, such as TWEAK, CD30 ligand, and LTalb2, which trigger a weaker death signal limited to a few cells. Studies in these systems have suggested that a separate weaker death signaling mechanism exists. Lastly, there those members that cannot efficiently deliver a death signal. Probably all groups may exert antiproliferative effects on some cell types consequent to inducing cell differentiation, e.g., CD40.

In general, death is triggered following the aggregation of death domains which reside on the cytoplasmic side of the TNF receptors. The death domain orchestrates the assembly of various signal transduction components which lead to activation of the caspase cascade. Some receptors lack canonical death domains, e.g. LTb receptor and CD30, yet can induce cell death, albeit more weakly. Conversely, signaling through other pathways such as CD40 is required to maintain cell survival. There remains a need to further identify and characterize the functions of the TNF family members, thereby facilitating the development of new therapies for TNF family-related diseases.

TWEAK was isolated in a screen for RNA that hybridized to an erythropoietin probe. Chicheportiche et al., *J. Biol. Chem.* 272:32401-32410 (1997). The mouse and human peptides have an unusually high degree of conservation, including 93% amino acid identity in the receptor binding domain. TWEAK, shown to be efficiently secreted from cells, is abundantly expressed in many tissues, including heart, brain, placenta, lung, liver, skeletal muscle, kidney, pancreas, spleen, lymph nodes, thymus, appendix, and peripheral blood lymphocytes.

One known TWEAK receptor is Fn14, a growth factor-regulated immediate-early response gene that decreases cellular adhesion to the extracellular matrix and reduces serum-stimulated growth and migration (Meighan-Mantha et al., *J. Biol. Chem.* 274:33166-33176 (1999)). Fn14 has been shown to be induced by FGF, calf serum and phorbol ester treatment and is expressed at relatively high levels in heart, kidney, lung, skin, skeletal muscle, ovary and pancreas tissues, as well as in hepatocellular carcinoma modules and other cancer cell lines, and at lower levels in normal liver tissues.

TWEAK has been implicated in many biological processes. For instance, HT29 cells treated with IFN-γ and TWEAK were shown to undergo apoptosis; although TWEAK's ability to induce apoptosis is weak and only a small number of cell types are susceptible. Chicheportiche et al., *J. Biol. Chem.* 272:32401-32410 (1997). In contrast, TWEAK has also been shown to induce angiogenesis and proliferation of endothelial cells in a VEGF-independent pathway. Lynch et al., *J. Biol. Chem.* 274:8455-8459 (1999). Astrocytes are specifically bound and stimulated by TWEAK. TWEAK can infiltrate an inflamed brain to influence astrocyte behavior. Astrocytes exposed to TWEAK secrete high levels of IL-6 and IL-8, as well as upregulate ICAM-1 expression. Saas et al., *GLIA* 32:102-107 (2000).

TWEAK has also been implicated in immune system regulation. Upon stimulation with IFN-γ, monocytes rapidly express TWEAK, and anti-TWEAK antibodies partially inhibited their cytotoxic activity against human squamous carcinoma cells. A combination of anti-TWEAK and anti-TRAIL antibodies almost completely inhibited cytotoxicity. Nakayama et al., *J. Exp. Med.* 192:1373-1379 (2000). In contrast, TWEAK mRNA rapidly disappeared in mice treated with lipopolysaccharide (LPS), an inducer of the immunoinflammatory responses. Furthermore, TWEAK mRNA was also reduced in autoimmune hemolytic anemia and systemic lupus erythematosus in mouse models. These data suggest that the down-regulation of TWEAK expression is an important event in acute and chronic inflammation. Chicheportiche et al., *Biochem. Biophys. Res. Comm.* 279:162-165 (2000).

Currently, the art lacks a complete understanding of what conditions or diseases are related to TWEAK expression and function, including the role of TWEAK in both inflammatory and non-inflammatory conditions.

SUMMARY OF THE INVENTION

The present invention relates to the role of TWEAK in contributing to the severity and progression of various pathological conditions, including diseases of multiple tissues and organ systems. Such pathological conditions include acute cardiac injury, chronic heart failure, non-inflammatory dilated cardiomyopathy, congestive heart failure, liver epithelial cell hyperplasia, hepatocyte death, liver fibrosis, hepatocyte vacuolation, other liver injuries, bile duct conditions, including bile duct hyperplasia, inflammatory kidney conditions, such as multifocal inflammation, non-inflammatory kidney conditions such as tubular nephropathy, tubular hyperplasia, glomerular cysts, glomerular nephropathy, Alport Syndrome, kidney tubular vacuolation, kidney hyaline casts, kidney fibrosis and inflammatory lung disease. The present invention establishes a causal link between the TWEAK molecule and certain diseases of the heart, liver, kidney and lungs. The invention disclosed herein also establishes a link between TWEAK and the behavior of progenitor cells for liver tissue, kidney tubules, skin cells, adipocytes, skeletal muscle, cartilage and bone, as well as connective tissue cell types, such as stromal cells in the bone marrow and fibroblasts.

In one embodiment, the invention relates to methods for treating TWEAK-related conditions, i.e. diseases, settings of injury or other pathological conditions of tissues wherein a receptor for TWEAK, e.g. FN14, is expressed. Those conditions include fibrosis, cardiomyopathies, and diseases of the kidney, lung, liver, skin, skeletal muscle, lipid metabolism (e.g. obesity), gastrointestinal tract, pancreas, reproductive organs, neural tissue (including neurodegeneration), cartilage, bone and connective tissue. In a preferred embodiment, the TWEAK-related conditions are non-inflammatory in nature. In another preferred embodiment, the invention relates to methods for treating TWEAK-related conditions by interfering with the interaction of the TWEAK polypeptide with its cellular receptor.

In other embodiments, the invention relates to TWEAK agonists or antagonists and pharmaceutical compositions comprising them for use in treating TWEAK-related conditions. Such TWEAK agonists or antagonists (i.e. inhibitors) may be anti-TWEAK antibodies, or derivatives thereof; anti-TWEAK receptor antibodies, or derivatives thereof; TWEAK polypeptide fragments; TWEAK polypeptide analogs; TWEAK muteins; TWEAK mimetics; TWEAK fusion proteins; TWEAK receptor polypeptide fragments; TWEAK receptor polypeptide analogs; TWEAK receptor muteins; TWEAK receptor mimetics; TWEAK receptor fusion proteins; organic compounds; and inorganic compounds.

In other embodiments, the invention relates to TWEAK agonists or antagonists and pharmaceutical compositions useful in treating hosts in need of tissue regeneration or replacement. It also relates to use of TWEAK agonists or antagonists for modulating the behavior of populations of progenitor cells in vivo or in vitro. The progenitor cells may be the precursors of liver cell types, kidney tubules, cardiomyocytes, lung cell types, skin cell types, skeletal muscle cell types, adipocytes, gastrointestinal cell types, pancreatic cell types, neural tissue cell types, cartilage and bone cell types, connective tissue cell types, including stromal cells in the bone marrow and fibroblasts. TWEAK agonists or antagonists and pharmaceutical compositions comprising them may be administered in vivo to promote tissue regeneration and replacement in settings of disease or tissue injury, including but not limited to, toxin, viral, chemotherapy or radiation-induced damage, and genetic or degenerative disorders. In another embodiment, TWEAK agonists or antagonists and pharmaceutical compositions thereof could be used in combination with cellular therapy with stem cells or progenitor cells to regenerate tissue and organ systems. In yet another embodiment, stem cells or progenitor cell populations may be expanded in vitro by TWEAK agonists or antagonists and pharmaceutical compositions thereof. Progenitor cell populations expanded through the use of TWEAK agonists or antagonists may be used for transplantation into hosts in need of tissue regeneration or replacement.

In other embodiments, the invention relates to methods for identifying TWEAK agonists or antagonists useful as therapeutic agents for the treatment of TWEAK-related conditions. In another embodiment, the invention relates to transgenic animals expressing exogenous DNAs encoding TWEAK polypeptides. A further embodiment of this invention includes the use of TWEAK as a molecular marker for disease.

BRIEF DESCRIPTION OF THE DRAWINGS

FIG. 6: TWEAK causes hepatocellular vacuolization in FL-TWEAK transgenic (Tg) mice as compared to non-transgenic (NTg) littermates.

FIG. 8: TWEAK overexpression in the liver induces hepatocyte death and ductal hyperplasia. Cross sections of the liver are viewed at 20× magnification with hematoxylin/eosin staining on days 3 and 11 following infection of adult C57BL/6 mice with an adenoviral vector comprising murine sTWEAK DNA compared with an adenovirus-GFP control construct.

FIG. 10: Fn14 expression is upregulated in biliary epithelial cells in a murine model of bile duct ligation, as revealed by increased staining with the anti-sense mRNA probe directed against Fn14 using in situ hybridization. Hemotoxylin and eosin (H&E) stained section shows the corresponding section in bright field microscopy.

FIG. 15: TWEAK overexpression in the kidney induces tubular hyperplasia and glomerulopathy. A cross section of the kidney is viewed at 20× and 40× magnification with hematoxylin/eosin staining on day 11 following infection of adult C57BL/6 mice with an adenoviral vector comprising murine sTWEAK DNA compared with an adenovirus-GFP control construct.

FIG. 23: Inhibitory effect of TWEAK on 3T3-L1 cell adipocyte differentiation in vitro. 3T3-L1 cells were induced to undergo differentiation using a standard protocol. Cells were untreated, treated with a control agent (recombinant soluble human CD40L-FLAG 100 ng/ml) or various versions of TWEAK at 100 ng/ml recombinant soluble human TWEAK-FLAG, recombinant soluble human TWEAK, Fc-human TWEAK) on day 0, together with dexamethasone and insulin, and were replenished daily. In one experimental group, the blocking anti-TWEAK mAb AB.G11 was also added at the same time as Fc-hTWEAK. The cells were stained with Oil-red O on day 7.

DETAILED DESCRIPTION OF THE INVENTION

Figure 1:
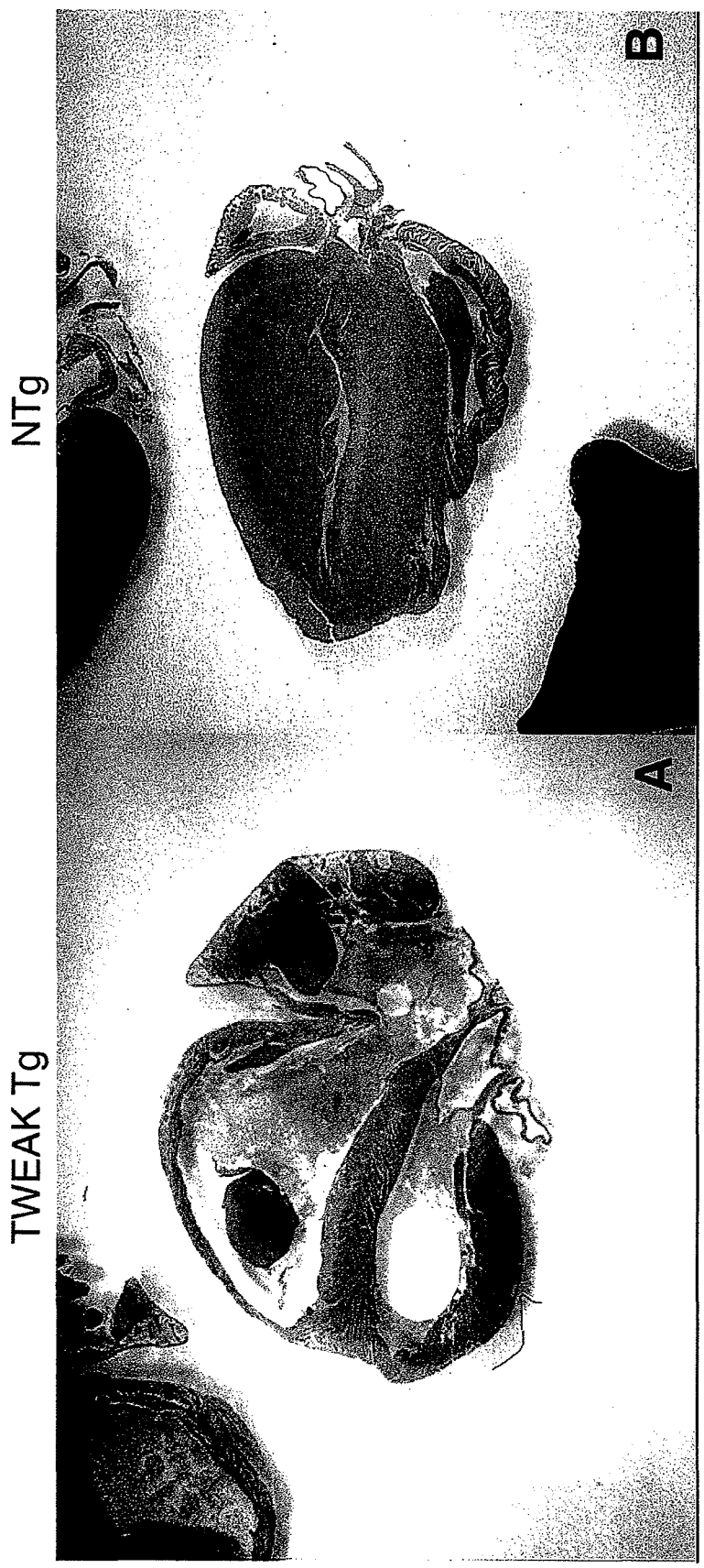
FIG. 1: The role of TWEAK in dilated cardiomyopathy is shown. A. A FL-TWEAK transgenic (Tg) mouse shows thrombosis of the right atrium and ventricle, as well as severe dilation. B. Normal heart is shown for comparison.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics, virology and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In order that the invention herein described may be more fully understood, the following detailed description is set forth. In the description, the following terms are employed:

"Antibody" refers to an intact immunoglobulin, or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH1 domains; a F(ab')2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544-546, 1989) consists of a VH domain. A single-chain antibody (scFv) is an antibody in which a VL and VH regions are paired to form a monovalent molecules via a synthetic linker that enables them to be made, as a single protein chain (Bird et al., Science 242:423-426 (1988) and Huston et al., Proc. Natl. Acad. Sci. USA 85:5879-5883, (1988)). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., Proc. Natl. Acad. Sci. USA 90:6444-6448 (1993), and Poljak et al., Structure 2:1121-1123 (1994)). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

"Antibody repertoire" refers to the sum of every different antibody species in an animal or human. Diversity in antibody repertoires results from, inter alia, immunoglobulin gene recombination, immunoglobulin gene junctional diversity, terminal deoxytransferase activity, and somatic hypermutation.

"Chimeric antibodies" are antibodies that have been altered from their original form to comprise amino acid sequences from another protein. Chimeric antibodies retain at least a portion of the original antibody amino acid sequence, typically the portion comprising the antigen binding region (Fab). Examples of chimeric antibodies include, but are not limited to, bispecific antibodies and fusions with other non-immunoglobulin protein sequences.

"cis regulatory elements" generally refer to sequences that regulate the inducible or constitutive expression of gene sequences under specific conditions or in specific cells. Examples of cellular processes that expression control sequences regulate include, but are not limited to, gene transcription, protein translation, messenger RNA splicing, immunoglobulin isotype switching, protein glycosylation, protein cleavage, protein secretion, intracellular protein localization and extracellular protein homing.

"Cytokines" refer generally to signaling molecules of the immune system. Cytokines include, but are not limited to, Interleukins (IL), transforming growth factors (TGF), tumor necrosis factors (TNF), lymphotoxins (LT), interferons, granulocyte-macrophage colony stimulating factors (GM-CSF), macrophage CSF, Granulocyte CSF, and migration inhibition factors.

"Embryonic stem (ES) cells" refer to pluripotent or multipotent cells that can, when injected into a blastocyst, contribute to many or all tissues of a prenatal, postnatal or adult animal. Animals that result from blastocyst injections are often referred to as "chimeric" animals since their somatic and/or germ cells are often derived from both the blastocyst donors and the injected ES cells. One important property of ES cells is their ability to contribute to the germ line of the animals, resulting in any desired heritable characteristics to be passed to the chimeric animal's progeny. Immortalized ES cells are a powerful tool for generating animals with targeted disruptions of endogenous gene sequences or for generating animals with foreign genes (transgenes).

"Expression control sequences" refer to sequences that allow for the constitutive or inducible expression of gene sequences under specific conditions or in specific cells. Examples of cellular processes that expression control sequences regulate include, but are not limited to, gene transcription, protein translation, messenger RNA splicing, immunoglobulin isotype switching, protein glycosylation, protein cleavage, protein secretion, intracellular protein localization and extracellular protein homing.

"Fusion Proteins" refer to chimeric proteins comprising amino acid sequences of two or more different proteins. Typically, fusion proteins result from in vitro recombinatory techniques well known in the art. However, fusion proteins may result from in vivo crossover or other recombinatory events.

"Human immunoglobulin molecules" refer to immunoglobulin proteins that are encoded by human immunoglobulin gene sequences. The immunoglobulin gene sequences may be expressed in any cell or animal, human or non-human.

"Humanized antibodies" are antibodies that are derived from a non-human species, in which certain amino acids in the framework and constant domains of the heavy and light chains have been mutated so as to avoid or abrogate an immune response in humans. Alternatively, humanized antibodies may be produced by fusing the constant domains from a human antibody to the variable domains of a non-human species. Examples of how to make humanized antibodies may be found in U.S. Pat. Nos. 6,054,297, 5,886,152 and 5,877,293.

"Inflammation" or "inflammatory disease" refers to the fundamental pathologic process consisting of cytologic and histologic reactions that occur in blood vessels and adjacent tissues in response to injury, abnormal stimulation or biological agents. Likewise, "non-inflammatory conditions" or "non-inflammatory diseases" refer to any condition or disease that is not inflammatory in nature, as disclosed herein.

"Isolated protein" or "isolated polypeptide" refers generally to a protein or polypeptide that by virtue of its origin or source of derivation: (1) is not associated with naturally associated components that accompany it in its native state, (2) is free of other proteins from the same species, (3) is expressed by a cell from a different species, or (4) does not occur in nature. Thus, a polypeptide that is chemically synthesized, synthesized in a cell-free biological system (e.g., a rabbit reticulocyte lysate), or synthesized in a cellular system different from the cell from which it naturally originates will be "isolated" from its naturally associated components. A protein may also be rendered substantially free of naturally associated components by isolation, using protein purification techniques well known in the art.

"Mimetics" or "peptide mimetics" are non-peptide analogs that are commonly used in the pharmaceutical industry as drugs with properties analogous to those of the template peptide. Fauchere, *J. Adv. Drug Res.* 15:29 (1986); Veber and Freidinger, *TINS* p. 392 (1985); and Evans et al., *J. Med. Chem.* 30:1229 (1987), incorporated herein by reference. Mimetics are often developed with the aid of computerized molecular modeling. Peptide mimetics that are structurally similar to therapeutically useful peptides may be used to produce an equivalent therapeutic or prophylactic effect. Generally, mimetics are structurally similar to a paradigm polypeptide (i.e., a polypeptide that has a desired biochemical property or pharmacological activity), such as TWEAK, but have one or more peptide linkages optionally replaced by a linkage selected from the group consisting of: —CH2NH—, —CH2S—, —CH2-CH2-, —CH=CH— (cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference); for example, by adding internal cysteine residues capable of forming intramolecular disulfide bridges which cyclize the peptide.

"Polypeptide analogs" refer to polypeptides that are derived from wild-type polypeptides but differ therefrom in their amino acid sequences. Polypeptides with changes in their amino acid sequences may be muteins, fusion proteins, or mimetics. Polypeptide analogs also refer to polypeptides that have non-amino acid sequence differences as compared with the wild-type polypeptides. These differences may be chemical or biochemical, and include, but are not limited to, the types of modifications specifically disclosed herein.

"Polypeptide fragments" refer to polypeptides that have an amino-terminal and/or carboxy-terminal deletion, but where the remaining amino acid sequence is identical to the corresponding positions in the naturally-occurring sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

"Progenitor cells" refer to cells that can give rise to one or more cell lineages. Included are stem cells, totipotent cells, pluripotent cells, multipotent cells, bipotent cells, embryonic cells or adult cells. Also included are tissue-specific cells, including, but not limited to, cells committed to a particular lineage capable of undergoing terminal differentiation, cells that derive from tissue resident cells, and circulating cells that have homed to specific tissues.

"Subjects" are humans and non-human subjects. An example of a subject is a patient.

"TWEAK-related conditions" refer to any conditions that result from aberrant TWEAK function or regulation. The term may also refer to any condition that does not directly result from aberrant TWEAK function or regulation, but rather arises out of some other mechanism wherein disrupting, increasing or otherwise altering TWEAK activity will have a detectable outcome on the condition. TWEAK-related conditions can be either inflammatory or non-inflammatory in nature, and include, but are not limited to, the conditions and diseases specifically disclosed herein.

"Vectors" refer to DNA molecules that allow DNA sequences of interest to be cloned, propagated, recombined, mutated, or expressed outside of their native cells. Often vectors have expression control sequences that allow for the inducible or constitutive expression of gene sequences under specific conditions or in specific cells. Examples of vectors include, but are not limited to, plasmids, yeast artificial chromosomes (YACs), viruses, Epstein Bar Virus (EBV)-derived episomes, bacteriophages, cosmids and phagemids.

"Xenogeneic animals" refer to animals bearing substantial portions of human immunoglobulin loci. Often, xenogeneic animals bear homologously targeted endogenous immunoglobulin loci, rendering them incapable of expressing their endogenous immunoglobulin genes. Examples include the mice of the XenoMouse™ line (Abgenix, Inc., Fremont, Calif.), which are capable of somatic rearrangement of transgenic human immunoglobulin genes, hypermutation of the human variable genes, immunoglobulin gene expression, and immunoglobulin isotype switching. Xenogeneic animals are capable of mounting effective humoral responses to antigenic challenge utilizing the human immunoglobulin gene sequences. Antibodies produced in xenogeneic animals are fully human and can be isolated from the animals themselves or progeny thereof, from cultured cells extracted from the animals or progeny thereof, and from hybridomas created from xenogeneic B lymphocytic lines or progeny thereof. Moreover, the rearranged human gene sequences encoding immunoglobulins raised against specific antigenic challenges can be isolated by conventional recombinant techniques.

"Xenogeneic antibodies" refer to antibodies that are encoded by foreign immunoglobulin loci. For example, in mice of the XenoMouse™ line, the human antibody loci encode xenogeneic antibodies.

"Xenogeneic monoclonal antibodies" refer to homogenous populations of antibodies that are produced in cloned, immortalized cells, e.g. hybridomas, derived from xenogeneic animals. For example, hybridomas made from mice of the XenoMouse™ line produce xenogeneic antibodies.

The understanding and treatment of diseases fundamentally advances upon determination of the molecular mechanisms or biochemical pathways underlying them. Physicians and researchers are thereby enabled to tailor therapeutic agents and formulate pharmaceutical compositions that specifically target those molecular mechanisms or biochemical pathways.

Some of the most complex and debilitating diseases afflicting humans include those of the heart, liver, kidney, lung, skin, skeletal muscle, lipid metabolism, gastrointestinal tract, nervous system, pancreas, reproductive organs, cartilage, bone, connective tissue system, and progenitor or stem cells. The present invention advantageously provides important advances in the understanding of these diseases. More particularly, the invention provides transgenic animals which express exogenous TWEAK proteins and demonstrate for the first time a correlation between expression of TWEAK protein and certain pathological conditions of the heart, liver, kidney and lung. The invention also provides methods for treating or preventing such pathological conditions, as well as methods for identifying TWEAK agonists or antagonists for use in those methods. Pathological conditions that may be treated according to the methods of this invention include acute cardiac injury, chronic heart failure, non-inflammatory dilated cardiomyopathy, congestive heart failure, liver epithelial cell hyperplasia, hepatocyte death, liver fibrosis, hepatocyte vacuolation, liver injury, bile duct conditions, including bile duct hyperplasia, inflammatory kidney conditions, such as renal multifocal inflammation, non-inflammatory kidney conditions, such as tubular nephropathy, tubular hyperplasia, glomerular cysts, renal hyperplasia, renal capsular thickening, glomerular nephropathy, Alport Syndrome, kidney tubular vacuolation, kidney hyaline casts, kidney fibrosis and inflammatory lung conditions. The invention further provides methods for detecting TWEAK structures or functions as molecular markers of disease, including TWEAK proteins or their functions, TWEAK antibodies and TWEAK nucleic acids.

The TWEAK-related conditions described herein are treated using TWEAK agonists or antagonists that are capable of altering TWEAK activity or disrupting the interaction between a membrane-bound or full-length form of TWEAK polypeptides with its cellular receptors. Alternatively, the therapeutic agents and treatment methods disrupt the interaction between a membrane-bound or full-length form of TWEAK polypeptides with another TWEAK polypeptide. Such interference may occur on the surface of a cell, intra-cellularly, extra-cellularly, or in vitro bound to a solid phase or in solution. In another alternative, the therapeutic agents and treatment methods disrupt the interaction between membrane-bound or full-length forms of TWEAK polypeptides and TWEAK interacting partners. Such interacting partners may be proteins, nucleic acids, saccharides, lipids, fatty acids, and steroids.

In a preferred embodiment of this invention, the TWEAK-related condition is non-inflammatory in nature.

In another preferred embodiment, the TWEAK-related condition is fibrosis, cardiomyopathy, kidney disease, lung disease or liver disease.

In another preferred embodiment, the TWEAK-related condition is skeletal muscle disease, adipose tissue disease, gastrointestinal tract disease, pancreatic disease, a reproductive organ disease, a neural tissue disease, cellular death, skin disease, cartilage disease, bone disease, or connective tissue disease.

In another embodiment, TWEAK agonists or antagonists may be used to treat subjects suffering from a condition, disease or injury that requires tissue replacement or regeneration (e.g. burn victims or radiation patients) by affecting progenitor cells in vivo. The TWEAK agonists or antagonists may also be used to treat subjects in vivo in combination with progenitor cell or tissue transplantation therapy. The TWEAK agonists or antagonists may also be used to expand cell populations in vivo or progenitor cell populations in vitro for subsequent transplantation into subjects with or without additional treatment. Progenitor cell populations used for in vivo cell therapy or in vitro expansion followed by transplantation may be embryonic or adult in origin. Adult-derived progenitors may be multipotent or tissue-restricted (Lagasse et al., *Immunity* 14:425-436 (2001); Jackson et al. *J. Clin. Invest.* 107:1355-402 (2001); Anversa and Nadal-Ginard, *Nature* 415:240-243 (2002); Gussoni et al., *Nature* 401:390-394 (1999); Brazelton et al., *Science* 290:1672-1674 (2000); Peterson et al., *Science* 284:1168-1170 (1999); Lagasse et al., *Nature Medicine* 6:1229-1234 (2000)).

Heart disease is the predominant cause of disability and death in industrialized nations. In the United States, heart disease causes about 40% of all mortalities, accounting for approximately 750,000 deaths annually. Most basic to the function of the heart is the myocardium, composed primarily of branching and anastomosing striated muscle cells (cardiac myocytes). Cardiac myocytes are much larger than the intervening interstitial cells, accounting for more than 90% of the volume of the myocardium. Inflammatory cells are rare and collagen is sparse in a normal myocardium.

Myocardial disease is common but occurs secondarily in a number of different heart conditions. Examples of myocardial disease include inflammatory disorders (e.g., myocarditis), and non-inflammatory heart conditions such as dilated cardiomyopathy, systemic metabolic disorders, muscular dystrophies, and genetic abnormalities in cardiac muscle cells.

The major types of cardiomyopathy include dilated, hypertrophic and restrictive cardiomyopathies. It is an object of the invention to provide methods for the treatment of dilated cardiomyopathy, which is typically non-inflammatory in nature. In the case of non-inflammatory dilated cardiomyopathy, which accounts for approximately 90% of the clinical cases of myocardial disease, the heart is characterized by progressive cardiac hypertrophy, dilation, and contractile (systolic) dysfunction. Dilated cardiomyopathy may occur at any age, but is most common in persons ranging in age from 20 to 60 years old. Diagnosis is often made through noninvasive cardiac imaging, particularly through two-dimensional echocardiography. The histopathology of dilated cardiomyopathy is characterized by degenerating myocytes with mild to moderate hypertrophy, an absence of inflammatory cells, and interstitial fibrosis.

Clinically, dilated cardiomyopathy presents with slowly progressive congestive heart failure, but patients may slip precipitously from a compensated to a decompensated functional state. Cardiac transplantation is frequently required. Fifty percent of patients die within two years, and seventy five percent within five years. The cause of death is typically progressive cardiac failure or arrhythmia, however, embolism caused by dislodgment of an intracardiac thrombus may occur.

Hearts characterized by dilated cardiomyopathy are enlarged, flabby, and weigh two to three times as much as normal hearts. All chambers are dilated, with wall thinning, fibrosis, and typically mural thrombi. In a minority of dilated cardiomyopathies, mitral or tricuspid regurgitation results from left ventricular chamber dilation. Cardiac muscle cells are hypertrophied with enlarged nuclei. Some of the causes of dilated cardiomyopathy include myocarditis, alcohol or other toxin abuse, pregnancy (peripartum cardiomyopathy), ischemia, coronary artery disease, hypertension, and genetic influences.

Idiopathic Dilated Cardiomyopathy (IDC), a disease of unknown etiology, is characterized by dilation of one or both ventricles, systolic dysfunction, and often progression to congestive heart failure. It is noted that the term "IDC" is used by some persons of skill in the art interchangeably with the term "dilated cardiomyopathy", suggesting that IDC is in fact a broad category of dilated cardiomyopathies that are not the result of alcohol abuse, toxic insult or myocarditis.

Microscopically, IDC is characterized by myocardiocyte hypertrophy, karymegaly and interstitial and perivascular fibrosis. In contrast to myocarditis, necrosis and cellular infiltration are not typically prominent in IDC patients, an indication of its non-inflammatory etiology. Consistent with that etiology is the fact that anti-inflammatory drugs, such as prednisone, are largely ineffective in treating IDC.

It is an object of this invention to provide methods of treating or preventing dilated cardiomyopathy associated with TWEAK activity. Because the cause of dilated cardiomyopathy (e.g., IDC) is largely unknown, specific therapies have not been developed. Patients are typically treated for heart failure using physical, dietary, and pharmacological interventions (e.g., beta-adrenoceptor antagonists, calcium antagonists, and anticoagulants) to control the symptoms. Also, cardiac transplantation is used when available.

Those of skill in the art have been unable to identify any immunological, histochemical, morphological, ultrastructural or microbiological marker that might be used to diagnose IDC. However, epidemiological evidence suggests that predisposition to IDC may be genetically-based. In 20 percent of IDC patients, a first-degree relative also shows evidence of IDC, suggesting frequent familial transmission. Those of skill in the art have recognized the need to determine molecular genetic markers for IDC in subclinical and clinical heart disease patients.

To date, the list of genes associated with dilated cardiomyopathy includes cardiac troponin T, d-sarcoglycan, cardiac b myosin heavy chain, cardiac actin, a-tropomyosin, Lamin A/C, Desmin, cardiac ryanodine receptor, desmoplakin, plakoglobin, dystrophin, and tafazzin. The need still exists to find additional genetic factors that contribute to dilated cardiomyopathy and to design therapeutics that target them. The present invention has, for the first time, demonstrated a causal link between TWEAK and dilated cardiomyopathy. It is therefore an object of the invention to provide a method for identifying dilated cardiomyopathy in a patient by detecting changes in TWEAK protein expression, TWEAK protein function, TWEAK mRNA expression, or a chromosomal alteration. Methods and reagents for detecting such molecular markers of disease are well known in the art, and involve immunological or immunohistochemical analyses, enzyme or other protein-function assays, and standard hybridization-based assays such as northern blots, Southern blots, single nucleotide polymorphism (SNP) analysis, and fluorescence in situ hybridization (FISH) analysis.

It should be noted that non-inflammatory dilated cardiomyopathy is characterized by progressive cardiac hypertrophy, dilation, and contractile dysfunction. In contrast, Chagas' disease is a rare form of myocarditis, which is an inflammatory heart disease that develops in humans and experimental animals following chronic *Trypanosoma cruzi* infection. Studies of Chagas' disease, which is prevalent in Central and South America, have identified anti-self antibodies in the sera of Chagas' disease patients. Joshua Wynne and Eugene Braunwald, *Heart Disease, A Textbook of Cardiovascular Medicine*, Volume 2, Ch. 41, pp. 1442-1444 (5th ed. 1997). The methods disclosed herein are directed to the treatment of the more common, non-inflammatory-type dilated cardiomyopathy associated with TWEAK activity.

An adult human kidney processes more than 1,700 liters of blood per day, resulting in approximately 1 liter of urine. The kidney functions in waste excrement, metabolism, water, salt and pH homeostasis, as well as contributing to the endocrine system. Renal diseases are more likely to cause morbidity than mortality, with approximately 35,000 deaths annually in the United States. In contrast, millions of persons are afflicted annually by non-fatal kidney diseases such as infections, kidney stones, and urinary obstruction.

Typically, glomerular diseases are caused by immunological disorders, whereas tubular and interstitial disorders are usually caused by toxins or infectious agents. A partial list of kidney diseases includes acute nephritic syndrome, asymptomatic hematuria or proteinuria, acute renal failure, chronic renal failure, renal tubular defects, urinary tract infection, nephrolithiasis, urinary tract obstruction and kidney fibrosis.

Kidney injuries that involve the tubules typically involve the interstitium as well. Diseases of the tubules can be inflammatory or non-inflammatory in nature and include ischemic or toxic tubular injury. A partial list of tubule diseases includes acute tubular necrosis and acute renal failure; inflammatory reactions of the tubules and interstitium (tubulointerstitial nephritis); tubular hyperplasia; tubulointerstitial fibrosis (a scarring disease initiated by tubular epithelial cells with interstitial fibroblast, mononuclear cell, glomerular ultrafiltrate, cytokine and chemokine components); and autosomal dominant polycystic kidney disease (ADPKD) (an inherited disorder characterized by large, fluid-filled cysts from the tubules and Collecting ducts and caused by a mutation in either the PKD1 or PKD2 genes).

Glomerular diseases represent the most daunting of the kidney diseases. For instance, chronic glomerulonephritis is the most common cause of chronic renal failure in humans. In the so-called secondary glomerular diseases, glomeruli may be injured by immunologic disorders such as systemic lupus erythematosus (SLE), as well as vascular disorders, e.g., hypertension and polyarteritis nodosa. Also, metabolic diseases, such as diabetes mellitus (i.e. diabetic nephropathy)

and hereditary conditions, such as Fabry disease, affect the glomeruli. The primary glomerular diseases include primary glomerulonephritis and glomerulopathy.

The group of diseases under the umbrella of hereditary nepthritis includes familial renal diseases associated primarily with glomerular injury. Alports syndrome is a form of nephritis that is accompanied by nerve deafness and various eye disorders, including lens dislocation, posterior cataracts, and corneal dystrophy. The disease is more prevalent in males because of its dominant X-linked genotype. However, some females are afflicted due to one of either an autosomal dominant and recessive genotype. The glomeruli of Alport kidneys show segmental proliferation or sclerosis. Sometimes the epithelial cells acquire a foamy appearance, due to neutral fat and mucopolysaccharide accumulation. The glomular and tubular basement membranes show irregular foci of thickening or attenuation, with splitting and lamination of the lamina densa.

Because kidney diseases are of significant clinical importance, those of skill in the art have recognized the need to understand their physiological and genetic causes. Skilled artisans further recognize the need to develop new therapeutic agents for treatment of chronic and acute kidney diseases. The invention demonstrates for the first time a causal link between TWEAK and kidney disease.

Therefore, in one embodiment, the invention provides methods for the treatment of kidney diseases. In a more preferred embodiment, the kidney disease may be Alport syndrome. In other more preferred embodiments of the invention, the target kidney diseases may be characterized by multifocal inflammation, tubular nephropathy, tubular hyperplasia, cysts, glomerular nephropathy, tubular vacuolation, fibrosis or hyaline casts.

Lung disease has been, and remains, a prevalent affliction. Primary respiratory infections, such as bronchitis, bronchopneumonia and other types of pneumonia, must commonly be treated by clinicians. Lung diseases may be exacerbated by environmental factors such as cigarette smoke, air pollution and other inhalants. Chronic bronchitis, emphysema, pulmonary fibrosis and malignancy are also quite common. The lungs are also secondarily involved in many terminal diseases, with pulmonary edema, atelectasis, or bronchopneumonia found in most critically-ill patients.

Asthma is a chronic relapsing inflammatory disorder characterized by hyper-reactive airways. The symptoms are typically characterized by an episodic, reversible bronchoconstriction. Asthma is caused by an increased responsiveness of the tracheobronchial tree to various stimuli and is often associated with an IgE response to external allergens.

There are two major types of asthma. The first type is extrinsic asthma, which is initiated by a type hypersensitivity reaction induced by exposure to an extrinsic antigen. The list of extrinsic asthma conditions includes atopic (allergic) asthma, occupational asthma, and allergic bronchopulmonary aspergillosis. The second type is intrinsic asthma, which results from nonimmune mechanisms, and is triggered by factors, such as aspirin ingestion, pulmonary infections, stress, cold, inhaled irritants, and exercise.

Those of skill in the art have recognized the need for a better understanding of lung disease, including both non-inflammatory and inflammation-based diseases, such as asthma. An increased understanding will facilitate the development of improved pharmaceutical agents for treating lung diseases. The present invention demonstrates for the first time a causal link between TWEAK and lung disease, and methods of treatment thereof. In more preferred embodiments of this invention, the lung disease is characterized by inflammation, including granulomatous and/or lymphohistiocytic inflammation.

The liver is the primary regulator of digestion and metabolic homeostasis, including the processing of dietary amino acids, carbohydrates, lipids, and vitamins, as well as the synthesis of serum proteins, detoxification, and excretion into the bile of endogenous waste products and pollutant xenobiotics. Thus, hepatic disease is typically very serious, sometimes life-threatening.

The liver is vulnerable to many types of diseases, including metabolic, toxic, microbial, circulatory, and neoplastic insults. Toxins or immunological disorders may cause hepatocytes to swell, and become edematous in appearance, with irregularly clumped cytoplasm and large clear spaces. Also, retained biliary material may cause the hepatocytes to become foamy and swollen. Accumulation of substances such as iron, copper and fat droplets (steatosis) can accumulate in hepatocytes. In cases of alcoholic liver disease and acute fatty liver of pregnancy, tiny droplets that do not displace the nucleus appear (known as microvesicular steatosis).

Hepatocyte necrosis, which results from significant liver injury, can be characterized by, inter alia, ischemic coagulative necrosis. Often, cell death from toxic or immunologically related conditions is characterized by rounded up hepatocytes and shrunken, pyknotic, intensely eosinophilic "Councilman bodies" containing fragmented nuclei (resulting from apoptosis). Alternatively, hepatocytes may become osmotically swollen and rupture (lytic necrosis).

Hepatitis results from some injury to the liver associated with an influx of acute or chronic inflammatory cells. Hepatocyte necrosis may precede the onset of inflammation, or vice versa. Fibrosis, an irreversible consequence of hepatic damage, usually results from inflammation or non-inflammatory mechanisms, such as a direct toxic insult. The characteristic deposition of collagen affects blood flow and perfusion of hepatocytes. With continuing fibrosis, the liver subdivides into nodules of regenerating hepatocytes with surrounding scar tissue (cirrhosis).

Oval cells are so named because of their morphological appearance as small, proliferating epithelial cells with an ovoid nucleus and scant basophilic cytoplasm. Oval cells normally reside in the terminal bile ductules that connect the intrahepatic ducts which are located in the portal triad with the hepatocyte cords. These cells may be derived from resident liver progenitor cells, or from bone marrow progenitor cells that have circulated and homed to the liver. These ductular progenitor cells have the potential to differentiate into both bile duct epithelial cells and hepatocytes. The present invention demonstrates that expression of a TWEAK transgene in mice has the capacity to expand the population of ductular progenitor cells.

Because of the high levels of morbidity and mortality caused by liver disease, the art has recognized that the molecular and genetic underpinnings of that disease must be elucidated. Identification of causative factors facilitates the discovery of therapeutic agents for treatment of chronic and acute liver diseases. The present invention demonstrates a causal link between TWEAK and liver disease, and advantageously provides methods for the treatment thereof. In a more preferred embodiment, the liver disease is epithelial hyperplasia, hepatocyte vacuolation, bile duct injury resulting in fibrosis, hepatocyte death or liver injury.

The skeletomuscular system is critical for posture and locomotion. Skeletal muscle can atrophy in response to disuse, which may be secondary to conditions of nerve or blood supply deprivation and drug exposure such as glucocorticoids. Skeletal muscle can also atrophy in conditions of genetic or degenerative disorders. These conditions or diseases can be inflammatory or noninflammatory in nature. Muscular dystrophy constitutes a large group of hereditary myopathies characterized by atrophy and loss of muscle fibers in the absence of nerve disease; one common form that is included in this group is Duchenne's muscular dystrophy. Congenital muscle disease may also occur in the context of glycogen storage diseases, such as acid maltase deficiency, which results in babies with weak muscles, poor athletes, enlarged hearts, and often early death from cardiac failure. Congenital disorders leading to muscle atrophy also include, but are not limited to, mitochondrial myopathies, lipid myopathies, central tubular myopathies, and rhabdomyolysis. Myopathic conditions also may develop in adults, one of the most commonly observed being alcoholic myopathy. Skeletal muscle wasting also may occur as a component of neuronal disease, including but not limited to, amyotrophic lateral sclerosis (ALS). In addition, skeletal muscle wasting, also known as cachexia, is an important pathological condition seen in most terminally ill cancer patients and often is directly responsible for patients' death. Diseases of skeletal muscle that occur in the context of inflammation or autoimmunity include polymyositis, inflammatory myopathies, and glucocorticoid induced atrophy. The present invention establishes a link between TWEAK and the ability of myoblasts to differentiate into myotubes. It is therefore an object of the invention to provide methods of treatment of skeletal muscle disorders by promoting skeletal muscle regeneration using in vivo or in vitro approaches.

Accumulation of fat cells occurs in conditions of obesity, including obesity associated with metabolic disorders such as Type II diabetes. Ingrowth into organs of fat cells, so-called fatty infiltration, occurs in a variety of settings, and is a pathological component of muscular dystrophies. The present invention has demonstrated a link between TWEAK and the ability of preadipocytes to differentiate into adipocytes. It is therefore an object of the invention to provide methods of treatment of disorders associated with an accumulation or paucity of adipocytes by modulating adipocyte differentiation with TWEAK agonists or antagonists or pharmaceutical compositions thereof.

The methods of treating a TWEAK-related condition according to the present invention utilize TWEAK agonists or antagonists or compositions comprising them. TWEAK agonists or antagonists useful in treating TWEAK-related conditions according to this invention are described herein and are known in the art. Such agents include those disclosed in, e.g., PCT International Publication Nos. WO 98/05783, WO 98/35061, WO 99/19490, WO 00/42073, and WO 01/45730, all of which are incorporated herein by reference. TWEAK antagonists useful in the methods of the invention include anti-TWEAK antibodies, such as antibodies that are human, non-human, humanized or xenogeneic, as described herein, and are polyclonal, monoclonal, or synthetic. Furthermore, the antibodies may be full-length, fragments thereof, or fusion proteins that include antigen recognition sequences.

TWEAK antagonists useful in the methods of the invention also include anti-TWEAK receptor antibodies. Here, the TWEAK receptor may be FN14 or other members of the TNF-R family that are bound by TWEAK. The antibodies to the TWEAK receptor may be human, non-human, humanized or xenogeneic, as described herein, and are polyclonal, monoclonal, or synthetic. Furthermore, the antibodies may be full-length, fragments thereof, or fusion proteins that include antigen recognition sequences.

Immunization of animals with TWEAK or TWEAK receptor antigens may be carried out by any method known in the art. See, e.g., Harlow and Lane, Antibodies: A Laboratory Manual, New York: Cold Spring Harbor Press, 1990. Methods for immunizing non-human animals, such as mice, rats, sheep, goats, pigs, cattle, horses and the like are well known in the art. See, e.g., Harlow and Lane and U.S. Pat. No. 5,994,619. In a preferred embodiment, the antigen is administered with or without an adjuvant to stimulate the immune response. Such adjuvants include, inter alia, complete or incomplete Freund's adjuvant, RIBI (muramyl dipeptides) or ISCOM (immunostimulating complexes).

The antigen chosen for immunization can be any one of the following: a TWEAK polypeptide; a TWEAK polypeptide fragment; a TWEAK mutein; a TWEAK mimetic; a TWEAK fusion protein; a TWEAK receptor polypeptide; a TWEAK receptor fragment; a TWEAK receptor mutein; a TWEAK receptor mimetic; a TWEAK receptor fusion protein; a cell expressing a TWEAK polypeptide, fragment, mutein, or fusion protein thereof; or a cell expressing a TWEAK receptor polypeptide, fragment, mutein, or fusion protein thereof. The immunoglobulins raised in the animals by immunization may be recovered from various tissues or fluids of the animals, including serum, milk, ascites, spleen, thymus, peripheral blood cells, fetal liver, bone marrow, peritoneum, and any other tissues or fluids having significant immunoglobulin concentrations. Also, hybridomas can be made and isolated that produce monoclonal antibodies secreted into the medium.

In preferred embodiments of this invention, the antibodies are polyclonal antibodies, monoclonal antibodies, or humanized antibodies. In a more preferred embodiment, the humanized antibodies comprise human antibody constant and/or framework regions. In another preferred embodiment, the antibodies are xenogeneic antibodies. In more preferred embodiments, the xenogeneic antibodies are polyclonal antibodies or monoclonal antibodies.

Xenogeneic antibodies are complete antibodies of one species that are expressed in an entirely different species. For instance, if a mouse expresses the DNA required to produce complete human antibodies, the resulting antibodies are xenogeneic (i.e. human antibodies produced in a mouse). Targeted inactivation (knockout) technology provides the opportunity to disrupt an animal's normal expression of endogenous immunoglobulin genes. Transgenic animal technology provides the opportunity to produce non-human animals that produce xenogeneic immunoglobulin proteins. Such xenogeneic animals can be mated to the immunoglobulin knockout animals described above, resulting in animals that produce only the xenogeneic immunoglobulins and not endogenous immunoglobulins.

Expression of xenogeneic immunoglobulin genes allows the production of a highly diverse repertoire of human antibodies, including monoclonal antibodies. This is because (1) the exogenous immunoglobulin genes retain their cis regulatory elements and are subject to the host animal's normal variable (V), diversity (D), and joining (J) recombinational events; (2) the exogenous immunoglobulin genes are expressed in a similar fashion as endogenous immunoglobulin loci; and (3) the resulting antibodies apparently support normal B lymphocytic development and humoral responses.

The exogenous immunoglobulin genes may be introduced into the animals as an entire immunoglobulin locus, a part of an immunoglobulin locus, or as a "minilocus" in which a more complete exogenous Ig locus is mimicked through the inclusion of a handful of the individual genes from that Ig locus. Furthermore, transgenic animals may be engineered to express transgenes that encode modified antibodies such as single-chain antibodies or chimeric antibodies.

TWEAK agonists or antagonists useful in the methods of the invention may also be TWEAK polypeptides, or fragments, analogs, muteins, or mimetics thereof, as described herein. Analogs can differ from the naturally occurring TWEAK amino acid sequence, or in ways that do not involve the sequence, or both. In a preferred embodiment, the TWEAK polypeptide analogs are muteins. Methods of generating muteins are well known in the art of molecular biology, and include altering DNA molecules by random mutagenesis, site directed mutagenesis, deletions and truncations. Techniques for mutagenizing DNA are well known in the art, and include polymerase chain reaction (PCR) mutagenesis, saturation (i.e. chemical or radiation) mutagenesis, chemical DNA synthesis, alanine scanning mutagenesis, oligonucleotide-mediated mutagenesis (hybridization to a DNA template in vitro followed by enzymatic elongation), cassette (recombinant) mutagenesis, and combinatorial mutagenesis (introduction of random degenerate sequences into the TWEAK DNA).

The TWEAK polypeptides bind to TWEAK receptors, to other TWEAK polypeptides, or to other TWEAK-interacting partners. The TWEAK fragments may be membrane bound, and may be delivered in pharmaceutical compositions that comprise liposomes or other cellular or pseudocellular delivery systems. The TWEAK fragments may also be soluble TWEAK polypeptides that contain either a truncation or internal deletion that removes the transmembrane domain. Furthermore, the TWEAK polypeptides useful in the methods of the invention may result in either no TWEAK response, or an altered TWEAK response. Examples of such TWEAK polypeptides are analogs of the TWEAK protein, including deletion or truncation mutants, peptides containing one or more amino acid substitutions, TWEAK mimetics, as well as non-amino acid sequence-modified TWEAK polypeptides.

TWEAK agonists or antagonists useful in the methods of the invention may also be TWEAK receptor polypeptides, or fragments, analogs, muteins, or mimetics thereof, as described herein. The TWEAK receptor polypeptides are bound by TWEAK polypeptides, to other TWEAK receptor polypeptides, or to other TWEAK receptor-interacting partners. The TWEAK receptor fragments may be membrane bound, and may be delivered in pharmaceutical compositions that comprise liposomes or other cellular or pseudocellular delivery systems. The TWEAK receptor fragments may also be soluble TWEAK receptor polypeptides that contain either a truncation or internal deletion that removes the transmembrane domain. Furthermore, the TWEAK receptor polypeptides useful in the methods of the invention may result in either no TWEAK response, or an altered TWEAK response. Examples of such TWEAK receptor polypeptides are analogs of TWEAK receptor proteins, including deletion or truncation mutants, peptides containing one or more amino acid substitutions, TWEAK receptor mimetics, as well as non-amino acid sequence-modified TWEAK receptor polypeptides.

Moreover, TWEAK agonists or antagonists useful in the methods of the invention may be organic or inorganic compounds. The organic compounds may be either small organic compounds, such as those found in chemical libraries well known in the art. Other organic compounds include, but are not limited to, nucleic acids, peptides, saccharides, lipids and fatty acids, steroids, or derivatives thereof. Inorganic compounds may be silica based or other minerals and salts. The organic or inorganic compounds may bind to TWEAK polypeptides, TWEAK receptor polypeptides, or other TWEAK interacting partners, as described herein.

Non-sequence modifications of the TWEAK or TWEAK receptor polypeptides may result from in vivo or in vitro chemical derivatization the polypeptides, and include, but are not limited to, changes in acetylation, methylation, phosphorylation, carboxylation, oxidation state, or glycosylation. In addition, chemical derivatization may involve coupling to organic polymers such as polyethylene glycol (PEG) or other polymers known in the medicinal arts. Therefore, a TWEAK polypeptide analog may result from a non-amino acid sequence modification.

The TWEAK or TWEAK polypeptides may be expressed as fusion proteins. Fusion proteins are well known in the art. A person of skill in the art may choose from a wide variety of fusion partner moieties, including those from prokaryotes and eukaryotes.

According to this invention, any individual, including humans and animals, may be treated in a pharmaceutically acceptable manner with a pharmaceutically effective amount of a TWEAK agonist or antagonist or compositions comprising such an agent, for a period of time sufficient to treat a TWEAK-related condition in the individual to whom they are administered over some period of time. Alternatively, individuals may receive a prophylactically effective amount of a TWEAK agonist or antagonist, or compositions comprising such an agent, which is effective to prevent a TWEAK-related condition in an individual to whom they are administered over some period of time. TWEAK agonists or antagonists useful in the methods of the invention may be formulated in pharmaceutical compositions by the methods disclosed herein and may be delivered by parenteral route, injection, transmucosal, oral, inhalation, ocular, rectal, long-acting implantation, topical, sustained-released or stent-coated means. TWEAK agonists or antagonists may be in a variety of conventional forms employed for administration. These include, for example, solid, semi-solid and liquid dosage forms, such as liquid solutions or suspension, slurries, gels, creams, balms, emulsions, lotions, powders, sprays, foams, pastes, ointments, salves, and drops.

In addition, TWEAK agonists or antagonists may be delivered via a gene therapy route. Briefly, nucleic acid molecules encoding proteins or expressing antisense molecules are delivered to a subject utilizing any of the vectors known in the art to be suitable for delivering the nucleic acid molecules to the target tissues or organs. Typical vectors include liposomes, plasmids, and viral vectors (e.g., retroviruses, adenoviruses and adeno-associated viruses).

The most effective mode of administration and dosage regimen of TWEAK agonists or antagonists, or compositions comprising them, will depend on the effect desired, previous therapy, if any, the individual's health status, the status of the condition itself, the response to the TWEAK agonists or antagonists and the judgment of the treating physician. TWEAK agonists or antagonists, or compositions comprising them, may be administered in any dosage form acceptable for pharmaceuticals or veterinary preparations, at one time or over a series of treatments.

The amount of TWEAK agonists or antagonists, or compositions comprising them, which provides a single dosage will vary depending upon the particular mode of administration, the specific TWEAK agonists or antagonists, or composition, dose level and dose frequency. A typical preparation will contain between about 0.01% and about 99%, preferably between about 1% and about 50%, of TWEAK agonists or antagonists or compositions thereof (w/w).

An exemplary, non-limiting range for a therapeutically or prophylactically effective amount of a TWEAK agonist or antagonist is between about 0.005-10.00 mg/kg body weight, more preferably between about 0.05-1.0 mg/kg body weight.

TWEAK agonists or antagonists, or compositions comprising them, may be administered alone, or as part of a pharmaceutical or veterinary preparation, or as part of a prophylactic preparation, with or without adjuvant. They may be administered by parenteral or oral routes. For example, they may be administered by oral, pulmonary, nasal, aural, anal, dermal, ocular, intravenous, intramuscular, intraarterial, intrapeutoneal, mucosal, sublingual, subcutaneous, transdermal, topical or intracranial routes, or into the buccal cavity. In either pharmaceutical or veterinary applications, TWEAK agonists or antagonists may be topically administered to any epithelial surface. Such surfaces include oral, ocular, aural, anal and nasal surfaces. Pharmaceutical compositions may be produced by means of conventional mixing, dissolving, granulating, dragee-making, levigating, emulsifying, encapsulating, entrapping or lyophilizing processes.

Pharmaceutical compositions for use in accordance with the present invention may be formulated in a conventional manner, using one or more physiologically acceptable carriers comprising excipients and auxiliaries which facilitate processing of the active compounds into preparations which can be used pharmaceutically. The appropriate formulation will be dependent upon the intended route of administration.

For transmucosal administration, penetrants appropriate to the barrier to be permeated are used in the formulation. Such penetrants are generally known in the art. For ocular administration, suspensions in an appropriate saline solution are used, as is known in the art.

For oral administration, the TWEAK agonists or antagonists may be formulated readily by combining the active agents with conventional pharmaceutically acceptable carriers. TWEAK agonists or antagonists may be formulated as tablets, pills, liposomes, granules, spheres, dragees, capsules, liquids, gels, syrups, slurries, suspensions and the like, for oral ingestion by a patient to be treated.

TWEAK agonists or antagonists, or compositions comprising them, may also comprise any conventional carrier or adjuvant used in pharmaceuticals or veterinary preparations. These carriers and adjuvants include, for example, Freund's adjuvant, ion exchanges, alumina, aluminum stearate, lecithin, buffer substances, such as phosphates, glycine, sorbic acid, potassium sorbate, partial glyceride mixtures of saturated vegetable fatty acids, waters, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

Pharmaceutical compositions for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All compositions for oral administration should be in dosages suitable for such administration.

For buccal administration, the compositions may take the form of tablets or lozenges formulated in conventional manner.

For administration by inhalation, TWEAK agonists or antagonists are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

TWEAK agonists or antagonists may be formulated for either parenteral administration by injection, e.g., by bolus injection, or continuous infusion. The agents may be formulated in aqueous solutions, aqueous suspensions, oily suspensions, or emulsions, and may contain formulatory agents such as suspending, stabilizing and/or dispersing agents. Formulations for injection may be presented in unit dosage form, e.g., in ampoules or in multi-dose containers, with an added preservative Typical aqueous solution formulations include physiologically compatible buffers such as Hanks solution, Ringer's solution, or physiological saline buffer. Typical oily suspensions may include lipophilic solvents or vehicles that include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspensions may also contain suitable stabilizers or agents which increase the solubility of the compounds to allow for the preparation of highly concentrated solutions. Alternatively, TWEAK agonists or antagonists may be in powder form for constitution with a suitable vehicle, such as sterile pyrogen-free water, before use.

The TWEAK agonists or antagonists may also be formulated in rectal compositions, such as suppositories or retention enemas, e.g., containing conventional suppository bases such as cocoa butter or other glycerides.

In addition to the formulations described, TWEAK agonists or antagonists may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for TWEAK agonists or antagonists which are hydrophobic is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are examples of delivery vehicles or carriers for hydrophobic drugs. Certain organic solvents, such as dimethylsulfoxide also may be employed, although they may display a greater toxicity.

Additionally, TWEAK agonists or antagonists may be delivered using a sustained-release system, such as semipermeable matrices of solid hydrophobic polymers containing the therapeutic agent. Various sustained-release materials are available and well known by those skilled in the art. Sustained-release capsules may, depending on their chemical nature, release the compounds for a few weeks up to over 100 days.

Depending on the chemical nature and the biological stability of the TWEAK agonist or antagonist, additional strategies for protein stabilization may be employed.

The pharmaceutical compositions also may comprise suitable solid or gel phase carriers or excipients. Examples of such carriers or excipients include, but are not limited to calcium carbonate, calcium phosphate, various sugars, starches, cellulose derivatives, gelatin, and polymers such as polyethylene glycols.

TWEAK agonists or antagonists may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

TWEAK agonists or antagonists may also be formulated into pharmaceutical compositions useful for coating stents, for the treatment of the TWEAK-related heart conditions.

The present invention also relates to a method for identifying a TWEAK agonist or antagonist. Such TWEAK agonists or antagonists are useful for the treating TWEAK-related conditions, i.e., diseases, settings of injury or other pathological conditions of tissues wherein a receptor for TWEAK, e.g. FN14, is expressed. Those conditions include fibrosis and diseases of the heart (e.g. cardiomyopathies), kidney, lung, liver, skin, skeletal muscle, lipid metabolism (e.g. obesity), gastrointestinal tract, pancreas, reproductive organs, neural tissue (including neurodegeneration), cartilage, bone and connective tissue. Such TWEAK agonists or antagonists are also useful for promoting tissue replacement by modulating the behavior of progenitor cells in vivo or in vitro according to the present invention.

One embodiment of the method for identifying a TWEAK antagonist comprises the steps of: 1) exposing a transgenic test animal that expresses an exogenous DNA encoding a TWEAK polypeptide, or a fragment, analog, mutein, or mimetic thereof, to a compound which is a candidate TWEAK antagonist; 2) comparing the fibrotic, cardiac, kidney, liver, lung, skin, skeletal muscle, lipid, gastrointestinal tract, pancreas, reproductive organs, neural, cartilage, bone or connective tissue from the transgenic test animal to the same organ or tissue from a reference animal that expresses the exogenous DNA but was not exposed to the compound; and 3) determining whether the compound has affected the fibrotic, cardiac, kidney, liver, lung, skin, skeletal muscle, lipid, gastrointestinal tract, pancreas, reproductive organs, neural, cartilage, bone or connective tissue. In another embodiment, the transgenic test animal is either a mammal or a non-mammal, as disclosed herein.

The transgenic animals disclosed herein express exogenous DNAs encoding TWEAK polypeptides, wherein the expression results in a TWEAK-related condition. In the examples, transgenic mice were generated that express exogenous TWEAK proteins in either a truncated, soluble form or in a full-length, membrane-bound form. The mice that express the exogenous TWEAK proteins revealed phenotypes that include non-inflammatory dilated cardiomyopathy, congestive heart failure, liver epithelial cell hyperplasia, hepatocyte vacuolation, liver injury and inflammatory kidney conditions, such as multifocal inflammation, non-inflammatory kidney conditions, such as tubular nephropathy, cysts, glomerular nephropathy, kidney tubular hyperplasia, kidney fibrosis and inflammatory lung conditions. Furthermore, wild-type mice that were infected with viral vectors that express exogenous TWEAK proteins showed ductal hyperplasia, hepatocyte death, liver fibrosis and liver injury as well.

Having these animals in hand, persons of skill in the art have a powerful method for drug discovery. Specifically, the animals that express exogenous TWEAK proteins represent a model system for practicing a method for the discovery of TWEAK agonists or antagonists useful for the prevention or treatment of the TWEAK-related conditions disclosed herein.

In preferred embodiments, the animals useful in these model systems are either mammalian or non-mammalian. In more preferred embodiments, the mammalian animals are mice, rats, hamsters, rabbits, dogs, cats, cows, pigs, goats, horses, sheep, guinea pigs and primates. In other more preferred embodiments, the non-mammalian animals are birds, fish, amphibians, insects, and invertebrates.

The exogenous DNA encoding the TWEAK polypeptide is expressed in the transgenic animals via expression control sequences that control the expression of the exogenous DNA in the animal. Expression control sequences that control transcription include, e.g., promoters, enhancers transcription termination sites, locus control regions, RNA polymerase processivity signals, and chromatin remodeling elements. Expression control sequences that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation.

Preferred expression control sequences for TWEAK expression in the transgenic animals include viral elements that direct high levels of protein expression, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. In one embodiment, the DNA encoding a TWEAK polypeptide is driven by the alpha1 anti-trypsin (AAT) promoter. For further descriptions of viral expression control elements, and sequences thereof, see, e.g., U.S. Pat. Nos. 5,168,062; 4,510,245; and 4,968,615.

The exogenous DNA may also be expressed in the transgenic animals from tissue-specific expression control elements, including promoters. Tissue-specific expression control elements are known in the art. Non-limiting examples of suitable tissue-specific promoters include the liver-specific albumin promoter (Pinkert et al., *Genes Dev.* 1:268-277 (1987)), lymphoid-specific promoters (e.g., Calame and Eaton, *Adv. Immunol.* 43:235-275 (1988); Winoto and Baltimore, *EMBO J.* 8:729-733 (1989); Banerji et al., *Cell* 33:729-740 (1983); and Queen and Baltimore, *Cell* 33:741-748 (1983)), neuron-specific promoters (e.g., Byrne and Ruddle *Proc. Natl. Acad. Sci. USA* 86:5473-5477 (1989)), pancreas-specific promoters (e.g., Edlund et al., *Science* 230:912-916 (1985)), mammary gland-specific promoters (e.g., U.S. Pat. No. 4,873,316 and European patent application 264,166), and developmentally-regulated promoters (e.g., Kessel and Gruss, *Science* 249:374-379 (1990); Campes and Tilghman, *Genes Dev.* 3:537-546 (1989)). Other non-limiting examples of tissue-specific promoters include the cardiac tissue promoter alpha myosin heavy chain promoter (α MHC), the skin tissue promoter keratin-14 (K14), the lung tissue promoter surfactant protein C (SPC), and the kidney tissue promoters Ksp-cadherin and kidney androgen-regulated protein (KAP). The exogenous DNA may also be expressed from an inducible eukaryotic promoter, such as the metallothionine (MT) promoter, or other inducible eukaryotic promoters known in the art.

In one embodiment of the present invention, the TWEAK polypeptide expressed in the transgenic animals of the invention may be a full-length TWEAK polypeptide. In another embodiment, the polypeptides expressed in the transgenic animals are fragments of the TWEAK polypeptide. In a preferred embodiment, the TWEAK polypeptide fragments are soluble TWEAK polypeptides.

In another embodiment, the invention relates to transgenic animals that express an exogenous DNA encoding a TWEAK polypeptide in a tissue selected from the group consisting of: heart; blood; vessel; lungs; liver; kidney; brain; placenta; skeletal muscle; pancreas; spleen; lymph; thymus; appendix; peripheral blood lymphocyte; gastrointestinal tract; neurons; skin; adipocyte; cartilage; bone; connective tissue. In one embodiment, the TWEAK DNA is expressed from a constitutive promoter. In another embodiment, the DNA is expressed from an inducible promoter. In another embodiment, the DNA is expressed from a tissue specific promoter.

The present invention also relates to methods of identifying TWEAK agonist compounds that may act as therapeutic agents for treatment of TWEAK-related conditions or for promoting tissue replacement by modulating the behavior of progenitor cells in vivo or in vitro according to the present invention. Agonist candidate compounds may be administered to normal animals and their effect on organ systems assessed. Fibrotic, cardiac, liver, kidney, lung, skin, skeletal muscle, lipid, gastrointestinal tract, pancreas, reproductive organs, neural, cartilage, bone or connective tissue from the treated animal is then compared to the same tissue from an untreated animal; it is thereby determined whether the compound has induced a biological effect in any of said tissues.

This invention also relates to methods of identifying TWEAK regulated genes that may act as therapeutic targets for treatment of TWEAK-related conditions. For example, RNA profiling could be carried out in TWEAK transgenic animals as compared to normal animals in various tissues and drug targets thus identified.

It is a further objective of the invention to provide methods of affecting progenitor stem cell proliferation or differentiation, including that of mesenchymal stem cell types that give rise to muscle cells, cartilage, bone or connective tissue cell types such as stromal cells, fibroblasts, adipocytes and dermal cells. It is also an objective of the invention to provide methods of affecting the proliferative or differentiative ability of oval cells, which can give rise to biliary epithelial cells or hepatocytes and kidney progenitors, which can give rise to tubular epithelium.

EXAMPLES

In order that this invention may be better understood, the following examples are set forth. These examples are for the purpose of illustration only and are not to be construed as limiting the scope of the invention in any manner.

Example 1

Generation of TWEAK Transgenic Mice

In order to identify target organ(s) for TWEAK activity and the biological consequences of TWEAK signaling in vivo, two murine TWEAK expression constructs were created and used for the overexpression of TWEAK peptides in normal (C57Bl/6×DBA/2)F1 and (C57Bl/6×SJL/J)F2 mice using standard transgenic techniques. R. S. Williams and P. D. Wagner, *J. Applied Physiology* 88:1119-1126 (2000). The TWEAK expression constructs used were as follows: (1) A TWEAK cDNA from amino acids 101-249 of SEQ ID NO:1, encoding a soluble form of murine TWEAK (designated sTWEAK) downstream of a murine IgG signal sequence was inserted into the CH269 expression vector (a derivative of vector PCDEP4 (Invitrogen) containing the SV40 poly A addition sequence) downstream of the human alpha1 anti-trypsin (AAT) promoter and a beta-globin intron and upstream of the human growth hormone (hGH) poly A sequence; and (2) A cDNA encoding the full-length, transmembrane form of the protein (designated FL-TWEAK) corresponding to amino acids 1-249 of SEQ ID NO:1 was inserted into the pBlueScript expression vector (as described in Desplat-Jego et al., *J. Neuroimmunology* 133:116-123 (2002)) containing the SV40 poly A addition site. The FL-TWEAK sequence plus the poly A addition site was then isolated and cloned into another vector; a fragment containing the ApoE enhancer-human AAT promoter regulatory region was then inserted upstream to create the expression vector CA300. The AAT promoter has been shown to direct transcription primarily in liver and at lower levels in other tissues including kidney. P. Koopman et al., *Genes Dev.* 3:16-25 (1989).

For the sTWEAK transgene construct, 23 independent transgenic founders were identified by tail DNA PCR using probes corresponding to the sequence of nucleotides 468 to 488 (5' primer) and the complementary strand sequence for nucleotides 693 to 713 (3' primer) of SEQ ID NO:2. In addition, a serum ELISA for TWEAK revealed that 10 of these 23 founder animals had detectable levels of TWEAK in their serum, ranging from 0.06-3.0 micrograms/ml. The remaining 13 founders had no detectable serum TWEAK, i.e. <10 ng/ml. Nine of the 10 PCR+, serum TWEAK+ founders began to exhibit ill health at approximately 4-5 months of age. Weight loss, hunched posture, unkempt fur and bulging eyes were noted. Five of these founders died unexpectedly and therefore the remaining four that showed signs of illness were sacrificed with signs of ill health. In contrast, only 1 of 13 PCR+ serum negative founders exhibited ill health or died. Also, 0 of 4 PCR negative littermates exhibited ill health/died.

For the FL-TWEAK transgene construct, two independent transgenic founders were identified by tail DNA PCR and Northern blot analysis for TWEAK mRNA expression in liver tissue. In addition, a serum ELISA for TWEAK revealed that neither of these two founder animals had detectable levels of TWEAK in their serum, i.e., less than 10 nanograms/ml. The FL-TWEAK Tg founder mice did not exhibit a clinically observable phenotype.

Example 2

Overexpression of TWEAK in Mice Infected with an Adenoviral Vector Delivering an Exogenous DNA Encoding sTWEAK In order to identify the biological effects of overexpression of TWEAK in vivo, 8-10 week old C57BL/6 female adult mice were infected with a replication-defective adenoviral vector with a cytomegalovirus (CMV) promoter driving the cDNA for either murine sTWEAK ("Adeno-TWEAK") or jellyfish green fluorescent protein ("GFP") using standard adenoviral techniques as described in Tao et al., *Molecular Therapy* 3:28-35 (2001). An adenoviral vector comprising GFP ("Adeno-GFP") was used as the negative control. To determine whether mice were successfully infected with the Adeno-TWEAK construct, TWEAK protein levels in the serum were determined and monitored at various time points using standard ELISA assays.

Systemic overexpression of murine sTWEAK in the adult mice induced tissue changes in at least three major organs: liver, kidney and heart. See, Table 1. The phenotypes of these adenoviral construct-expressing mice were compared with the phenotypes of TWEAK Tg mice from Example 1 in Table 1. These observations are discussed in more detail in the following examples below.

TABLE 1

TWEAK Overexpression Induces Tissue Remodeling in Adult Mice

| ORGAN | PHENOTYPE | TWEAK Tg | Adeno-TWEAK in Adult Mice | Adeno-GFP in Adult Mice |
| --- | --- | --- | --- | --- |
| Liver | Bile Duct Hyperplasia | + | + | − |
|  | Hepatocyte Death | − | + | − |
| Kidney | Tubular Hyperplasia | + | + | − |
| Heart | Dilated Cardiomyopathy | + | + | − |

Example 3 sTWEAK and FL-TWEAK Induce Dilated Cardiomyopathy

Four of the surviving PCR+ serum sTWEAK+ founders from Example 1 were sacrificed and examined for gross morphological abnormalities. See, Table 2. Macroscopic observation at the time of necropsy revealed enlarged hearts, some 2-3 fold increased in size as compared to those of normal animals. Since the enlarged heart phenotype was observed in multiple independent sTWEAK transgenic founders, it is highly unlikely to be due to independent insertional events. Furthermore, an analysis of the serum chemistry of the sTWEAK transgenic mice showed elevated cardiac specific creatine kinase.

TABLE 2 sTWEAK Transgenic Mice

| FOUNDERS | SERUM TWEAK | PHENOTYPE |
| --- | --- | --- |
| 10 PCR+ | 0.06-3.0 µg/ml | 9/10 dead at 4-5 months 4/5 submitted for histophathological examination had enlarged heart |
| 13 PCR+ | <10 ng/ml | 1/13 dead at 6 months with enlarged heart |
| 4 PCR− | — | 0/4 dead at 6 months |

The enlarged heart phenotype was also observed in individual mice from one FL-TWEAK transgenic line that was established through successive backcross onto the C57BL/6 strain. See, Table 3. The FL-TWEAK transgene negative littermates showed no heart abnormalities.

TABLE 3

FL-TWEAK Transgenic Mice

| INDIVIDUALS | SERUM TWEAK | PHENOTYPE |
| --- | --- | --- |
| 7 PCR+ | — | 7/7 showed enlarged hearts at 5 months |
| 4 PCR− | <10 ng/ml | 0/4 dead at 5 months |

Taken together, these data strongly indicate that the enlarged heart phenotype is TWEAK-dependent.

Histopathological analysis of the hearts from the sTWEAK transgenic and FL-TWEAK transgenic mice showed similar findings. Low power microscopy of a FL-TWEAK transgenic heart ("Tg") as compared to a normal heart from a transgene negative ("NTg") littermate is shown in FIG. 1. The FL-TWEAK transgenic heart shown is also representative of TWEAK transgenic hearts from sTWEAK transgenic mice (PCR+, serum TWEAK+). The transgenic hearts exhibited dilated cardiomyopathy, characterized by dilation of the ventricles and atria. Consistent with this defect, atrial and ventricular thrombosis in many of the animals was noted (FIG. 1). Analysis of lung and liver tissue revealed congestion of the blood vessels in some animals.

Higher power microscopy revealed other histopathological findings in the heart, including myocardiocyte hypertrophy and karyomegaly. Notably, the histopathological analysis of the ventricles in TWEAK transgenic mice showed no signs of inflammation. Therefore, the observed TWEAK-related cardiomyopathy is non-inflammatory in nature.

Serum chemistry analysis on terminal bleeds from sTWEAK transgenic mice (3 founders and 1 progeny mouse) showed abnormally high levels of creatine kinase (CK) specifically in the heart (i.e. the MB type of CK), confirming a significant level of cardiac stress/injury.

Figure 2:
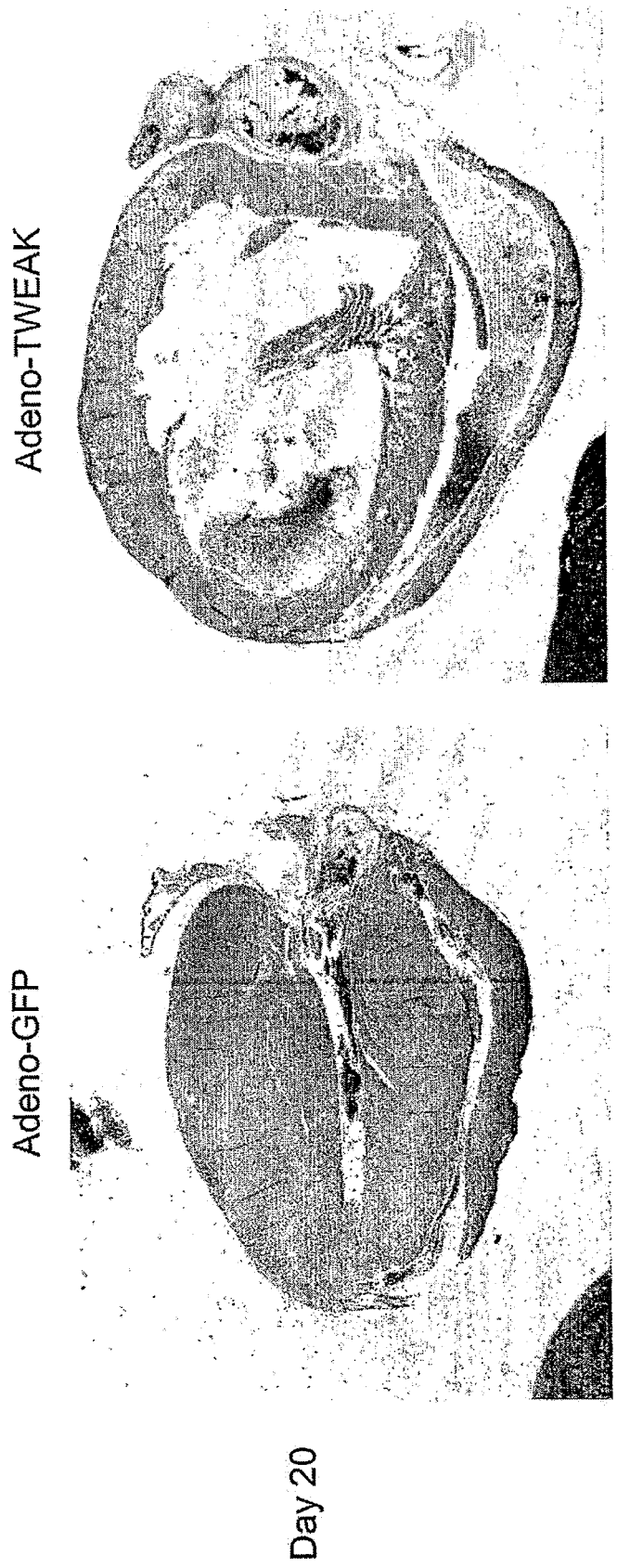
FIG. 2: TWEAK overexpression in the heart induces cardiac remodeling. A cross section of the heart is viewed at 10× magnification with hematoxylin/eosin staining on day 20 following infection of adult C57BL/6 mice with an adenoviral vector comprising murine sTWEAK DNA compared with an adenovirus-GFP control construct.

C57BL/6 female mice of 8-10 weeks of age infected with Adeno-TWEAK (see, Example 2) showed dilated cardiomyopathy which was apparent three weeks post infection as compared to mice infected with the negative control Adeno-GFP virus. In TWEAK-infected mice, the hearts were characterized by dilated chambers, as shown by histopathology (FIG. 2).

Taken together, TWEAK was shown to play a critical role in cardiomyopathies, including dilated cardiomyopathy, and congestive heart failure (CHF).

Example 4

TWEAK Causes Liver Epithelial Cell Hyperplasia, Hepatocyte Vacuolation, Hepatocellular Death, Bile Duct Hyperplasia, Liver Fibrosis and Liver Injury A role for TWEAK in liver epithelial hyperplasia and hepatocyte vacuolation was revealed in sTWEAK and FL-TWEAK transgenic mice as well as injury in wild-type mice infected with an adenovirus harboring a DNA that expresses a sTWEAK polypeptide.

Figure 3:
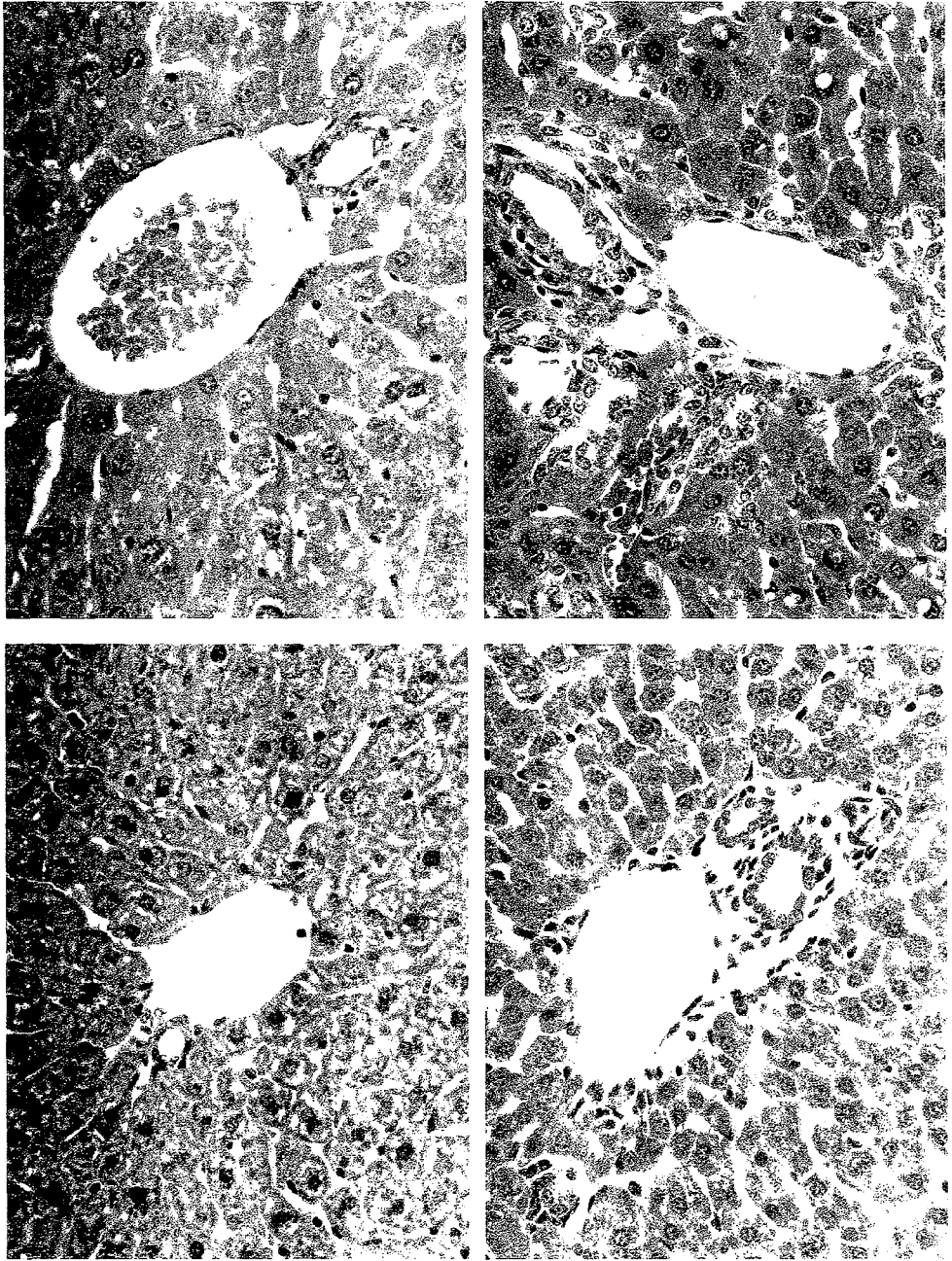
FIG. 3: TWEAK induces biliary duct and oval cell hyperplasia, as revealed in FL-TWEAK transgenic (Tg) mice as compared to non-transgenic (NTg) littermates at 2 weeks of age and 7 months of age.

The livers of TWEAK Tg mice from Example 1 showed substantial biliary duct and oval cell hyperplasia by 2 weeks of age as compared to NTg mice. See, FIG. 3. As shown in Table 4, even at serum TWEAK levels of <10 ng/ml, the livers of two FL-TWEAK transgenic mouse founders showed mild biliary duct and oval cell hyperplasia. FL-TWEAK transgenic mouse backcrosses into the C57BL/6 background revealed substantial biliary duct and oval cell hyperplasia (Table 4).

TABLE 4

FL-TWEAK Transgenic Mice

| MICE | SERUM TWEAK | PHENOTYPE |
|---|---|---|
| 2 Founders | <10 ng/ml | Mild biliary duct and oval cell hyperplasia |
| 1 Founder backcrossed into C57BL/6 | — | Prominent biliary duct and oval cell hyperplasia |

Similarly, the sTWEAK transgenic founders that have TWEAK serum levels between 0.2 and 3.0 µg/ml showed considerable biliary duct and oval cell hyperplasia (Table 5).

TABLE 5 sTWEAK Transgenic Mice

| MICE | SERUM TWEAK | PHENOTYPE |
|---|---|---|
| 9 Founders | 0.2-3.0 µg/ml | Prominent biliary duct and oval cell hyperplasia and oval cell hyperplasia |
| 1 Founder | 0.06 µg/ml | Mild biliary duct and oval cell hyperplasia |

Figure 4:
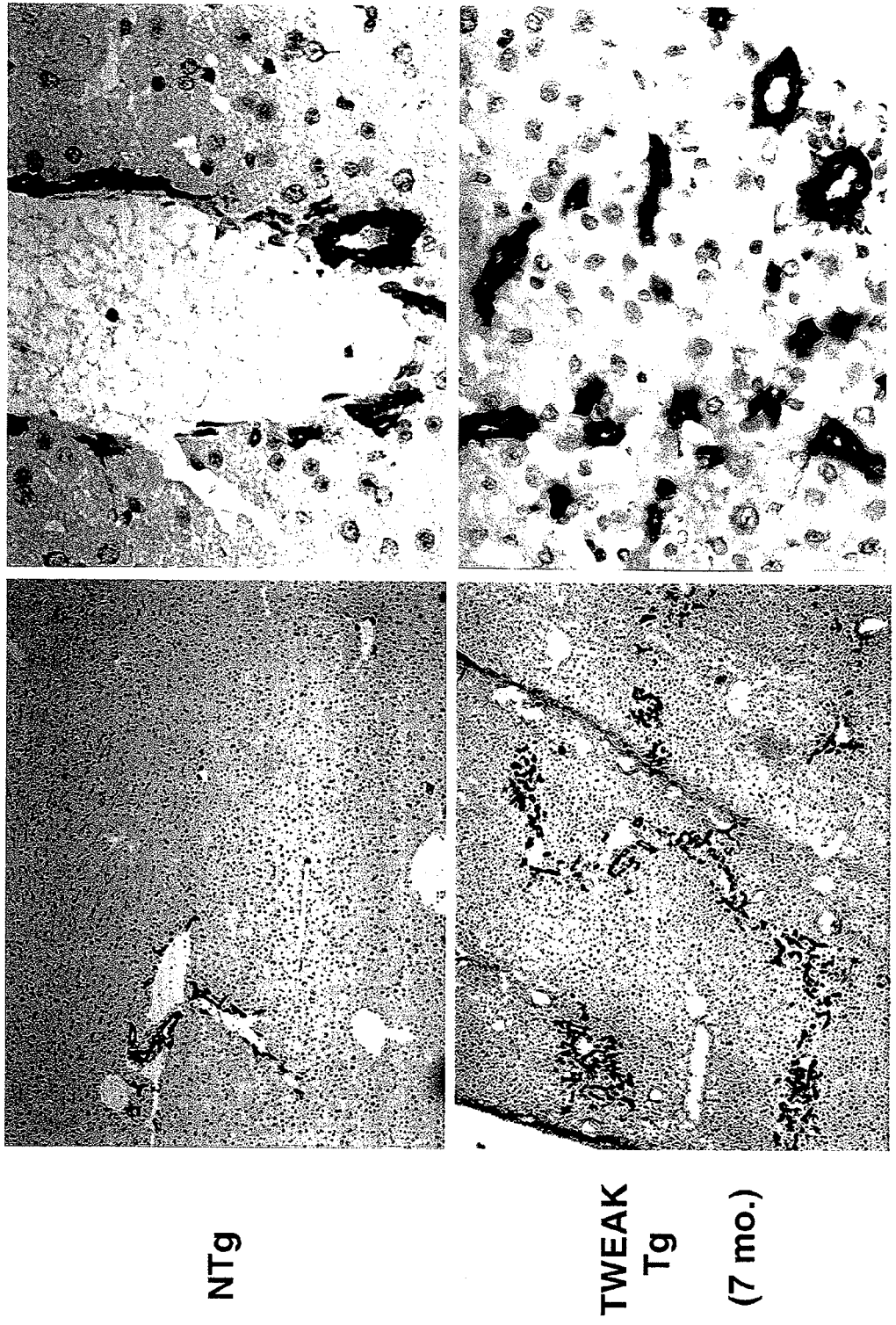
FIG. 4: TWEAK induces biliary duct and oval cell hyperplasia, as revealed by increased staining with the A6 mAb which is specific for a biliary epithelial and oval cell marker in FL-TWEAK transgenic (Tg) mice as compared to non-transgenic (NTg) littermates.
Figure 5:
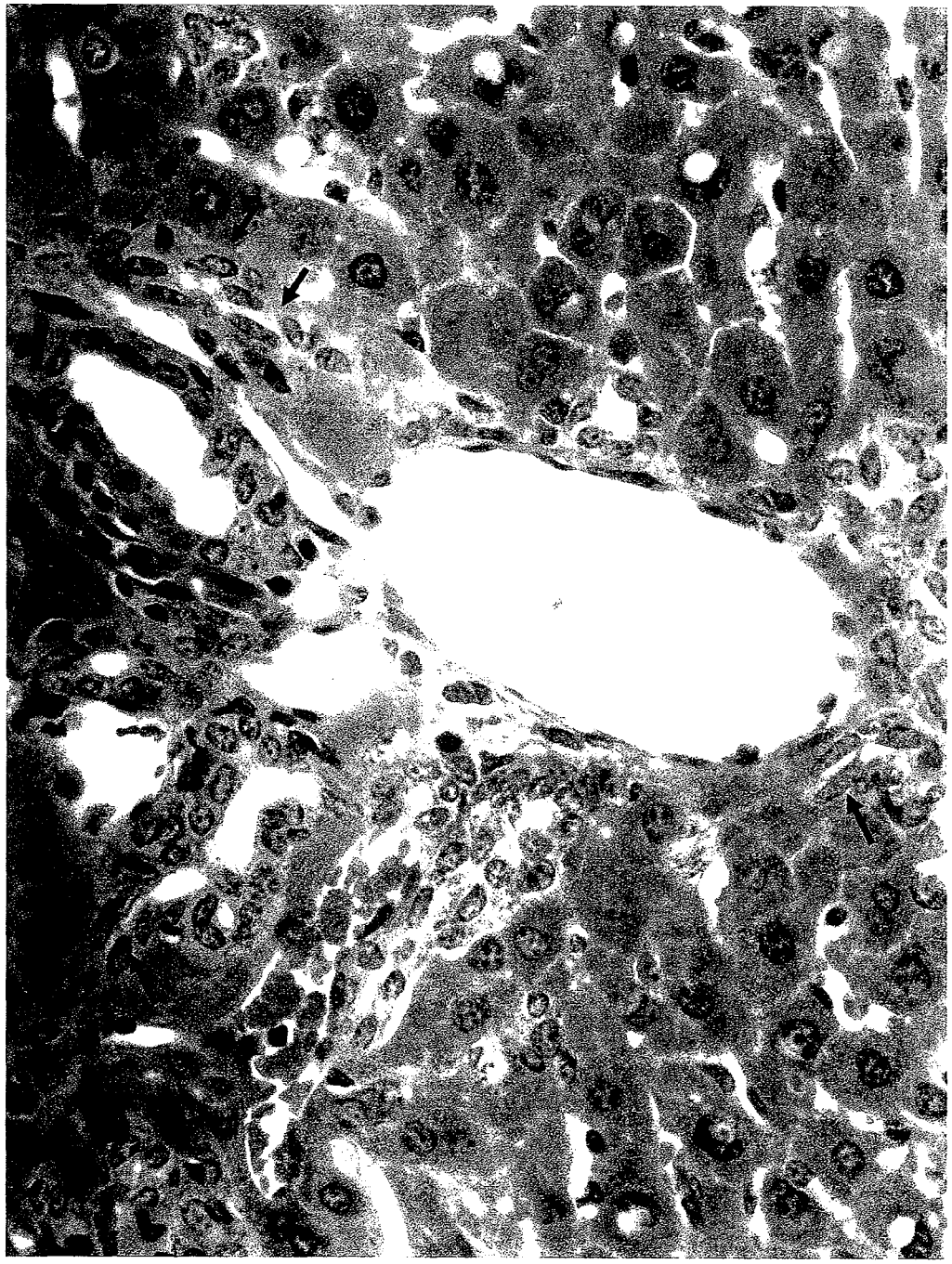
FIG. 5: TWEAK induces oval cell hyperplasia as revealed by the presence of large, oval cells in the portal region in FL-TWEAK transgenic (Tg) mice.

This biliary and oval duct hyperplasia was confirmed by immunohistochemical (IHC) staining of FL-TWEAK Tg liver sections taken from the Tg mice of Example 1 with the A6 mAb, which distinguishes biliary epithelial cells and oval cells from hepatocytes (Engelhardt et al., *Differentiation* 45:29-37 (1990)). FIG. 4 shows an increase in A6 positive cells that are associated with portal regions as well as extend out into the liver parenchyma in FL-TWEAK Tg as compared to NTg mice. Higher magnification of a hematoxylin and eosin stained section from a FL-TWEAK Tg mouse also clearly shows a marked increase in the presence of oval cells adjacent to the biliary ducts in the portal region (FIG. 5). Immunohistochemistry for the proliferating cell nuclear antigen (PCNA) confirmed an increased frequency of proliferating biliary and oval cells in, TWEAK Tg mice as compared to NTg mice as early as 2 weeks of age. At later time points, an increase in frequency of proliferating hepatocytes in TWEAK Tg mice as compared to NTg mice was observed, i.e., between 8 weeks and 7 months of age (not shown). Furthermore, both FL-TWEAK and sTWEAK induced hepatocellular vacuolization in 7 month old Tg mice from Example 1 as compared to NTg littermates (FIG. 6).

Figure 7:
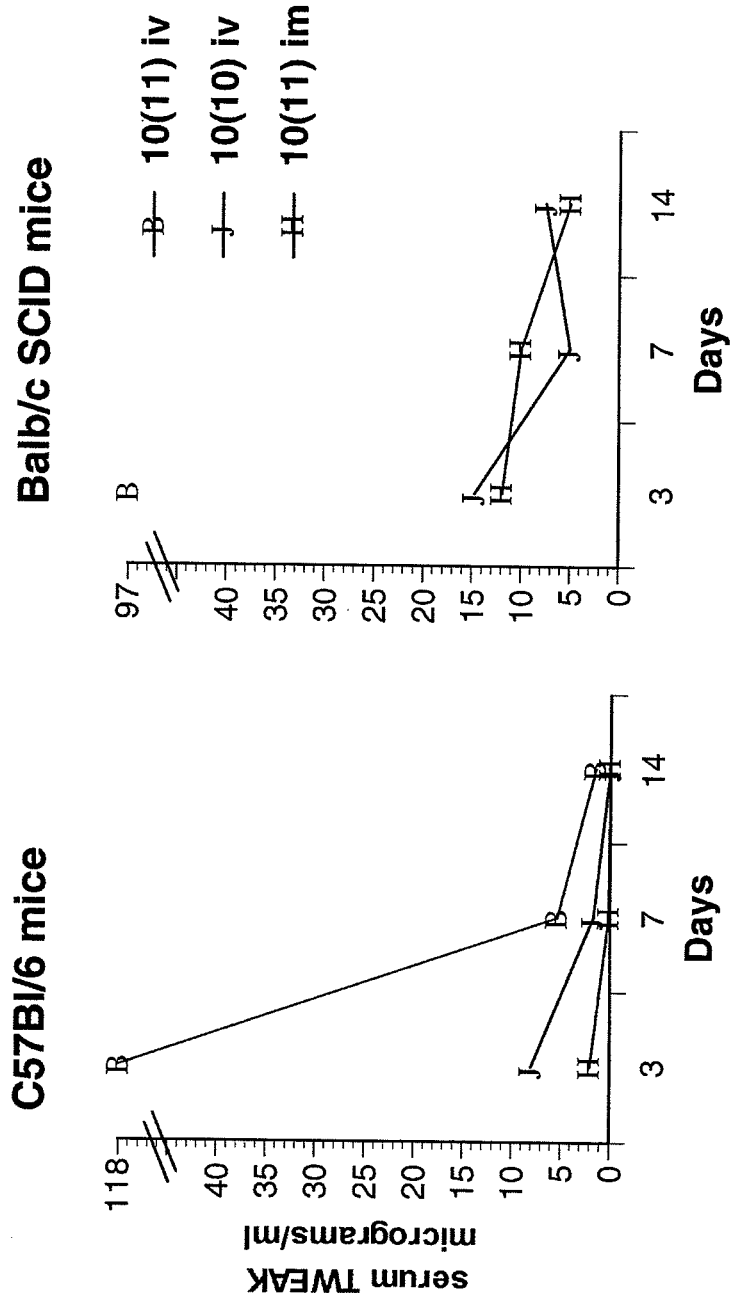
FIG. 7: Serum TWEAK levels in mice infected with an adenoviral vector comprising murine sTWEAK DNA.

C57BL/6 and BALB/c SCID mice of 8-10 weeks of age overexpressing sTWEAK using the Adeno-TWEAK virus as in Example 2 showed substantial serum TWEAK levels. See, FIG. 7, which displays the effect of delivering different doses of adenovirus on the serum TWEAK levels measured. Mice were infected with either $10^{11}$ particles of adenovirus per mouse intravenously (represented by the "B" line), $10^{10}$ particles of adenovirus per mouse intravenously (represented by the "J" line) or $10^{11}$ particles of adenovirus per mouse intramuscularly (represented by the "H" line). The Adeno-sTWEAK-infected mice showed liver injury, with serum jaundice observed on days 3 and 7 in the C57BL/6 mouse background and on days 3 and 4 of the BALB/c SCID mouse background. Some of the BALB/c SCID mice died on day 4.

Furthermore, the Adeno-sTWEAK-infected C57BL/6 mice as described in Example 2 also developed hepatocellular death which appeared as early as 2-3 days post administration, as demonstrated by the high level of the aspartate aminotransferase ("AST") and alanine aminotransferase ("ALT") liver enzyme markers in TWEAK-infected livers (Adeno-sTWEAK) compared with control GFP-infected livers (Adeno-GFP) by day 3 (see, Table 6 and FIG. 8). By day 7 post infection, both liver enzymes also rose in the Adeno-GFP treated mice, as would be expected due to the inflammation induced by the adenovirus vector alone. Hepatocyte death was also apparent in TWEAK-infected livers, as shown by the histologic morphology characterized by rounded up hepatocyes and shrunken, pyknotic, intensely eosinophilic "Councilman bodies" containing fragmented nuclei (FIG. 8). Adeno-sTWEAK treated mice further developed a strong hyperplastic ductal response, which peaked on day 7 post infection and was still readily apparent on day 11 (FIG. 8). In the TWEAK-infected livers, hyperplastic structures were observed that expressed the A6 marker specific for biliary epithelium and oval cells, as identified by bright field microscopy.

TABLE 6

Liver Enzyme Values in Ad-TWEAK And Ad-GFP Animals

| | Adeno-GFP | | Adeno-sTWEAK | |
|---|---|---|---|---|
| DAY | AST (U/L) | ALT (U/L) | AST (U/L) | ALT (U/L) |
| 3 | 148 | 110 | 1715 | 672 |
| 7 | 2140 | 1545 | 1910 | 1194 |
| 11 | 2540 | 2304 | 795 | 508 |
| 20 | 683 | 420 | 451 | 320 |

Figure 9:
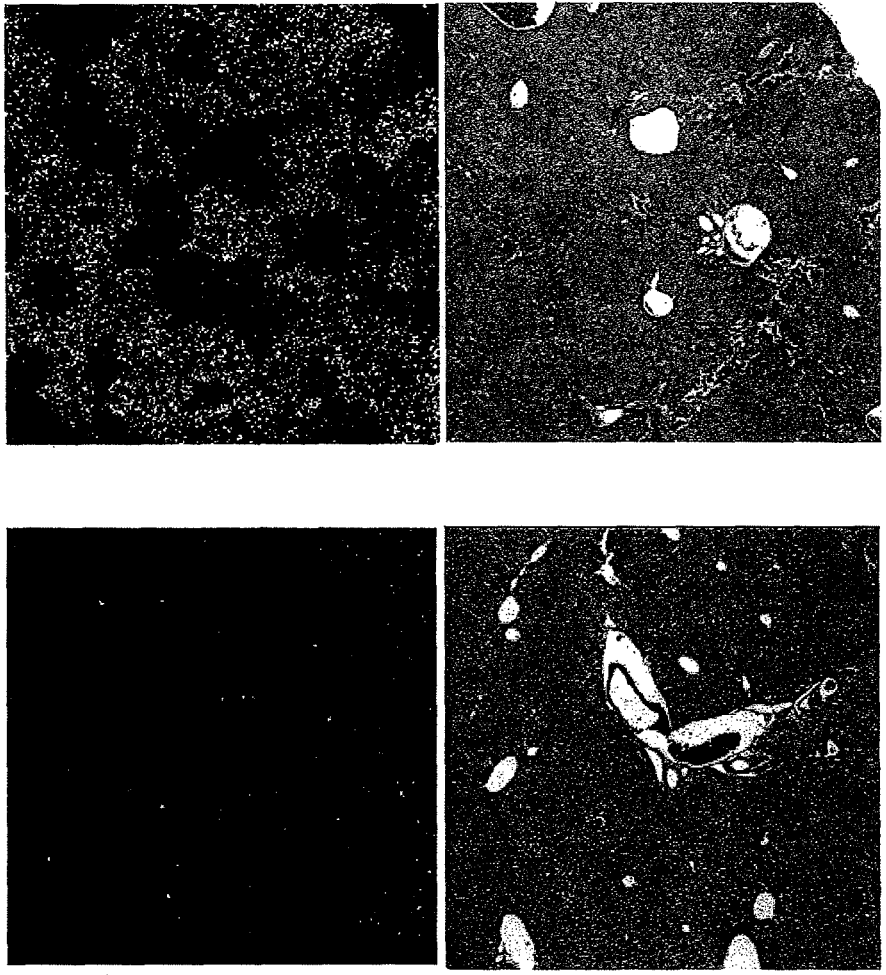
FIG. 9: The TWEAK receptor Fn14 is induced after $CCl_4$ induced liver injury in mice. In situ hybridization for Fn14 mRNA in normal mouse liver and $CCl_4$ induced liver injury shows little if any detectable expression in normal adult liver and marked induction of Fn14 expression after injury. Hemotoxylin and eosin (H&E) stained sections show the corresponding normal healthy liver and $CCl_4$ injured liver tissue.

Fn14, shown to be a cellular TWEAK receptor, was induced after exposure to liver toxins, such as galactosamine (GalN) and carbon tetrachloride ($CCl_4$). FIG. 9 shows that Fn14 is not detectable in normal adult mouse liver as measured by in situ hybridization (ISH) using a radiolabeled probe for Fn14 and dark field microscopy. However, Fn14 is highly induced following $CCl_4$ injury. Similar results were obtained after GalN injury (not shown).

Adeno-TWEAK-infected C57BL/6 mice as described in Example 2 also revealed upregulation of Fn14 in the hepatocytes and some hyperplastic structures, as observed in Adeno-sTWEAK livers compared with Adeno-GFP control livers (data not shown).

The role of Fn14 was further demonstrated in a bilary duct model wherein hepatic injury in 10 week old C57BL/6 mice was induced by ligation of the biliary duct as described by Liu et al., *Hepatology* 28:1260-1268 (1999); Olynyc et al., *Am. J. Pathol.* 152:347-352 (1998). The common bile duct was ligated on day 0 by surgery and five C57BL/6 mice of 10 weeks of age were then euthanized on day 4 and day 8 post surgery. Paraffin sections of liver were then prepared and the expression of TWEAK and Fn14 were determined by in situ hybridization using a radiolabeled murine TWEAK and FN14 anti-sense probe encompassing the complete FN14 gene. As shown in FIG. 10, by day 4, Fn14 was expressed strongly in biliary epithelial cells in bile ducts but not in hepatocytes. By day 8, Fn14 expression in biliary epithelial cells decreased significantly but was still detectable at low levels in some mice (data not shown). However, TWEAK expression did not change and was not detectable in this bile duct ligation model. These results show that Fn14 expression is upregulated in biliary epithelial cells in response to certain liver injuries and, thus, plays an important role in liver fibrosis.

Taken together, these observations show that TWEAK is an important factor in liver epithelial cell hyperplasia, hepatocyte vacuolation, liver injury, heptocellular death, bile duct hyperplasia and liver fibrosis.

Example 5

FL-TWEAK and sTWEAK Cause Kidney Disease

FL-TWEAK transgenic mice from Example 1 showed marked kidney disease, including mild multifocal inflammation, tubular nephropathy, cysts, glomerular nephropathy, tubular basophilia, tubular dilatation, tubular vacuolation and hyaline casts.

Adeno-TWEAK-infected C57BL/6 mice of 10 weeks of age as described in Example 2 revealed glomerular nephropathy and tubular hyperplasia as compared to negative control Adeno-GFP-infected mice. Also, a role for TWEAK in Alports syndrome was shown by increased Fn14 expression in a mouse model of Alports disease. Furthermore, a role for TWEAK in kidney fibrosis was demonstrated in the murine model of unilateral ureteral obstruction-induced kidney fibrosis by treatment with a TWEAK antagonist.

Figure 11:
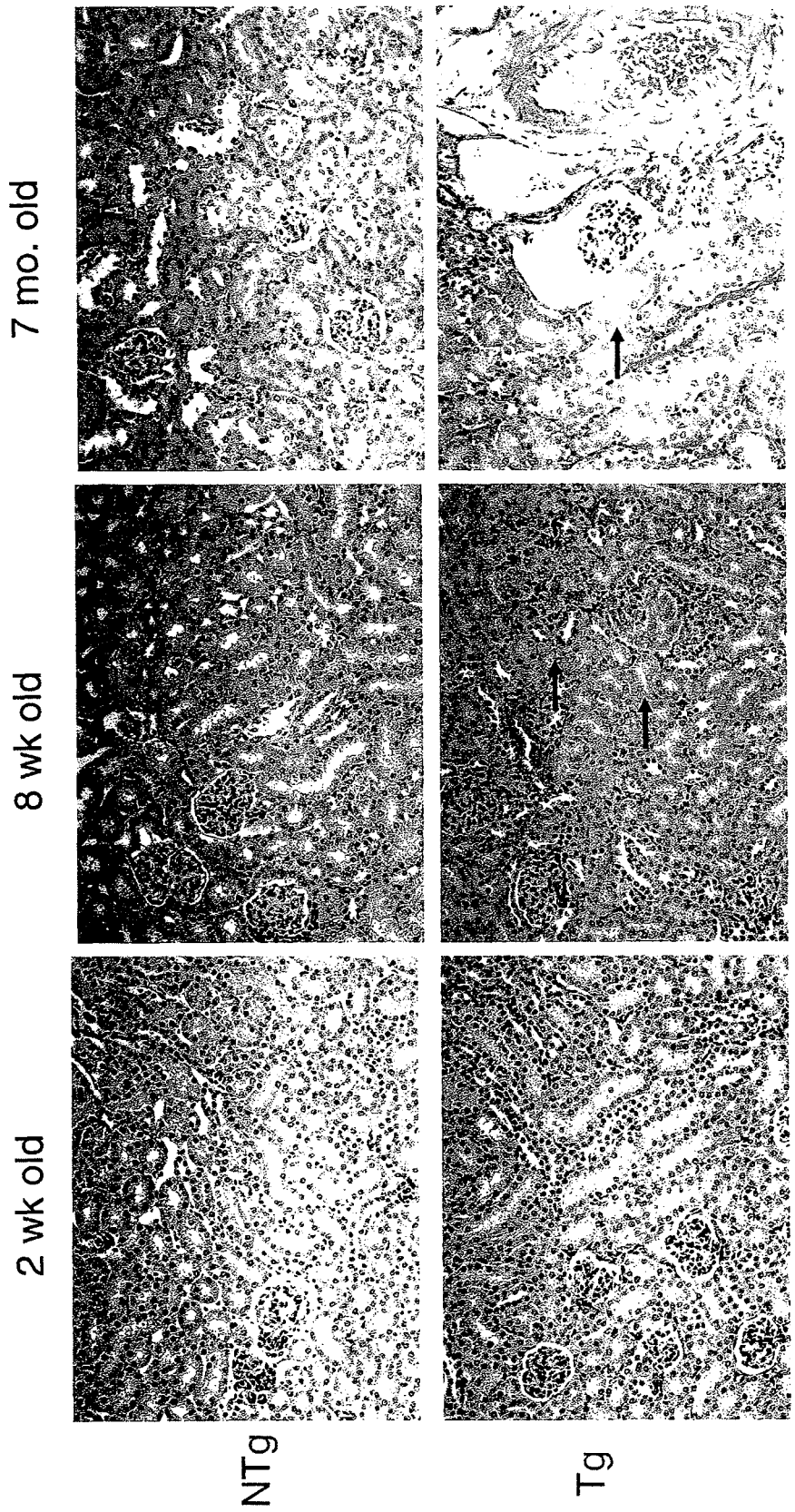
FIG. 11: Cross section of FL-TWEAK transgenic (Tg) mouse kidney as compared to non-transgenic (NTg) mouse kidney at 2 weeks, 8 weeks and 7 months of age. The results show tubular basophilia in the TWEAK Tg kidney at 8 weeks and 7 months of age, and dilatation of the urinary space in glomeruli, i.e., glomerular cysts, with adjacent basophilic tubules at 7 months of age.

Expansion of the cortical interstitium is typically due to edema or infiltration with acute or chronic inflammatory cells and fibrous tissue. FL-TWEAK transgenic mice from Example 1 showed tubular nephropathy and mild, multifocal interstitial inflammation. More specifically, kidney cross-sections comparing a non-transgenic mouse with FL-TWEAK transgenic mice showed pronounced tubular basophilia at 8 weeks of age (FIG. 11, middle panel).

Figure 12:
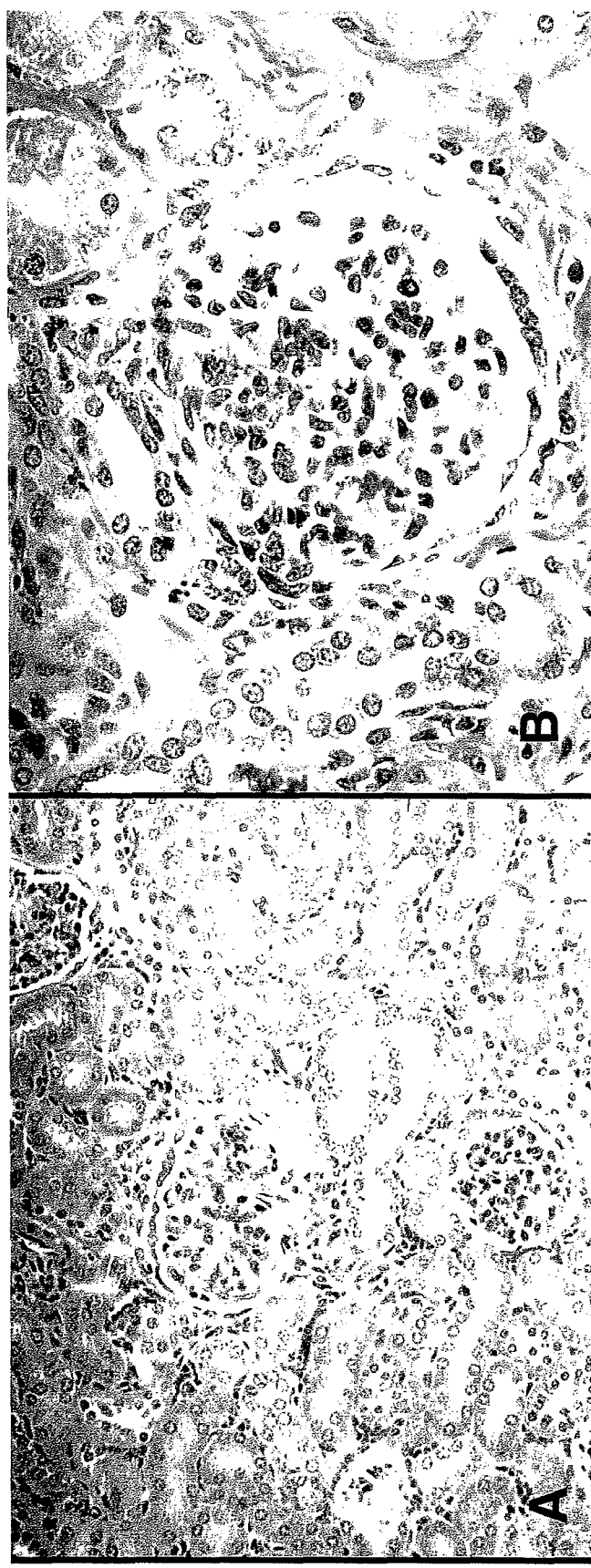
FIG. 12: Cross section of FL-TWEAK transgenic (Tg) mouse kidney with H&E staining. A. Glomerular nephropathy with basophilia of adjacent proximal tubular epithelium is shown. B. Segmental mesangial hypercellularity, hypertrophy of capsular epithelia, and capsular thickening.

Glomerular nephropathy may be characterized by an infiltration of leukocytes, both neutrophils and monocytes, and proliferation of endothelial, epithelial and mesangial cells. FL-TWEAK transgenic mice as described in Example 1 showed marked glomerular nephropathy as evidenced by hypercellularity of the mesangial cells and hypertrophy of capsular epithelia and mild capsular thickening with basophilia of adjacent tubular epithelium (FIG. 12). Also, FL-TWEAK transgenic mice showed dilation of the urinary space leading to formation of glomerular cysts with mild peri-glomerular fibrosis (FIG. 11, lower right panel), as compared to normal murine glomerular morphology (FIG. 11, upper right panel).

Figure 13:
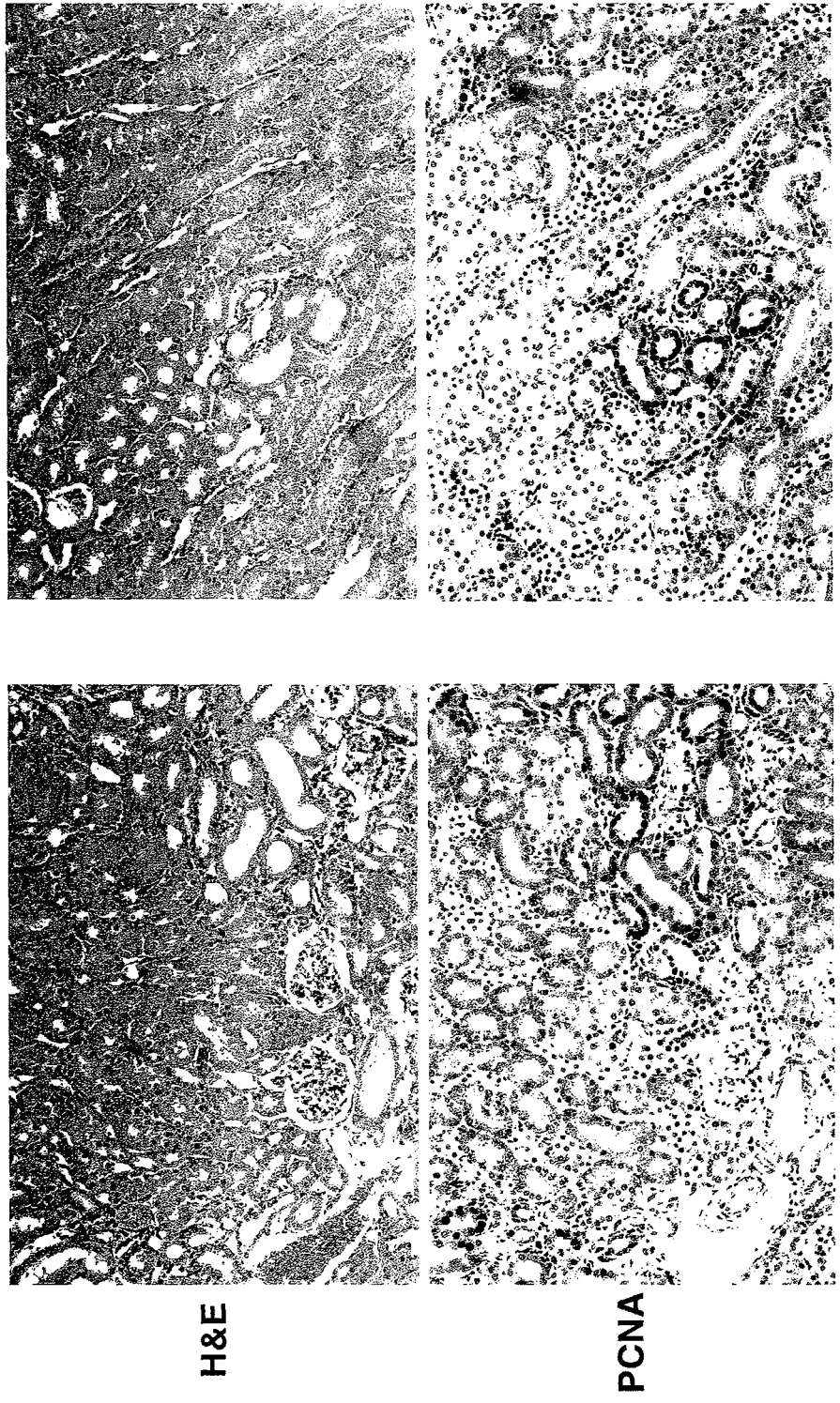
FIG. 13: Serial sections from two FL-TWEAK transgenic (Tg) mouse kidneys stained with H&E (top) and proliferating cell nuclear antigen (PCNA) (bottom). Basophilic tubules correspond to tubules expressing PCNA, i.e. proliferating tubules.
Figure 14:
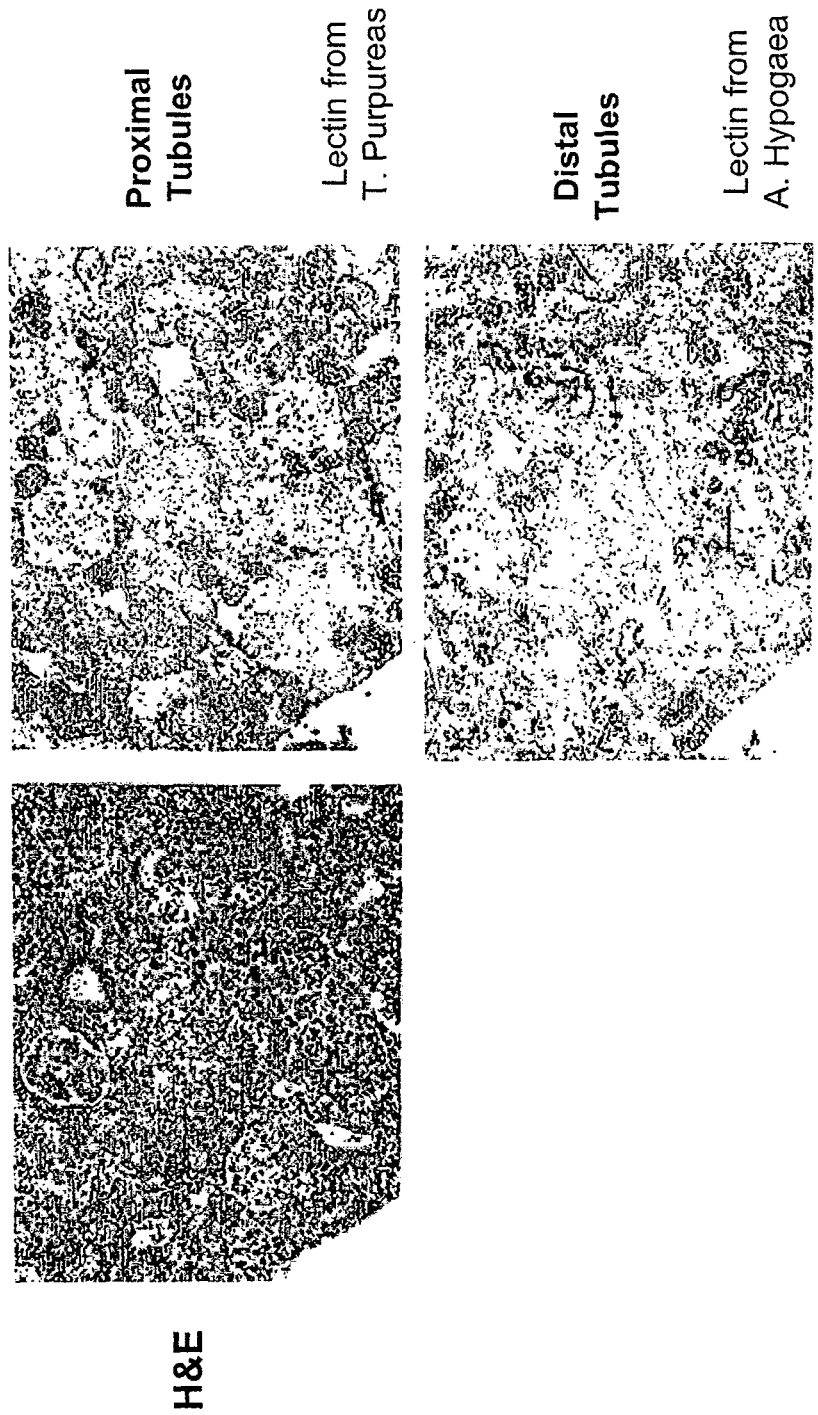
FIG. 14: Serial sections from a FL-TWEAK transgenic (Tg) mouse kidney stained with H&E, a lectin from *T. Purpureas* (a marker for proximal tubules) and a lectin from *A. Hypogaea* (a marker for distal tubules). Results show that the basophilic tubules do not express either epithelial marker.

The tubular basophilia observed in FL-TWEAK Tg mice is indicative of increased RNA in the cytoplasm of these tubular cells, i.e. transcriptional activity, and suggested that these were proliferating cells. Proliferating Cell Nuclear Antigen (PCNA) staining confirmed that there was a subset of tubular cells proliferating in the kidneys of TWEAK-Tg mice as described in Example 1 and that these corresponded to the basophilic tubules (FIG. 13). In order to determine whether the basophilic tubules were proximal or distal tubules, three serial tissue sections from TWEAK Tg mice were stained (1) with hemotoxylin and eosin (H&E) to localize the basophilic tubules, (2) with a lectin specific for proximal tubules (lectin from T. Purpureas) and (3) with a lectin specific for distal tubules. FIG. 14 shows that the basophilic (proliferating) tubules in TWEAK Tg mice as described in Example 1 do not express either the proximal or distal tubular epithelial marker.

The presence of proliferating tubules that lack at least some epithelial markers in the TWEAK Tg mice is consistent with a model for settings of kidney injury where cells derived from the S3 segment of the proximal tubule exhibit the properties of progenitor cells, i.e. they begin to proliferate and express mesenchymal cell markers indicative of dedifferentiation. Subsequent differentiation of these cells may play a role in tissue repair through the regeneration of new tubules (Witzgall et al., *J. Clin. Invest.* 93:2175-2188 (1994)). Alternatively, there may be proliferation and differentiation of a pre-existing progenitor population that resides in the S3 region.

The presence of proliferating cells that lack some epithelial markers in TWEAK Tg mice is also consistent with a model for kidney development, wherein epithelial tubules are formed from mesenchymal progenitors that undergo differentiation, thereby acquiring epithelial markers and properties characteristic of tubules.

Similarly, infection of 10 week old C57BL/6 mice with an Adeno-sTWEAK virus, as described in Example 2, induced glomerular nephropathy and basophilia of the tubular epithelium as well as occasional thickening and hyperplasia of the glomerular capsule by day 11 post infection (FIG. 15). This was in contrast to the normal histology observed in the negative control Adeno-GFP-infected mice. Furthermore, the basophilia, which is indicative of epithelial cell proliferation, was apparent by day 3 but peaked around one week post administration.

Figure 16:
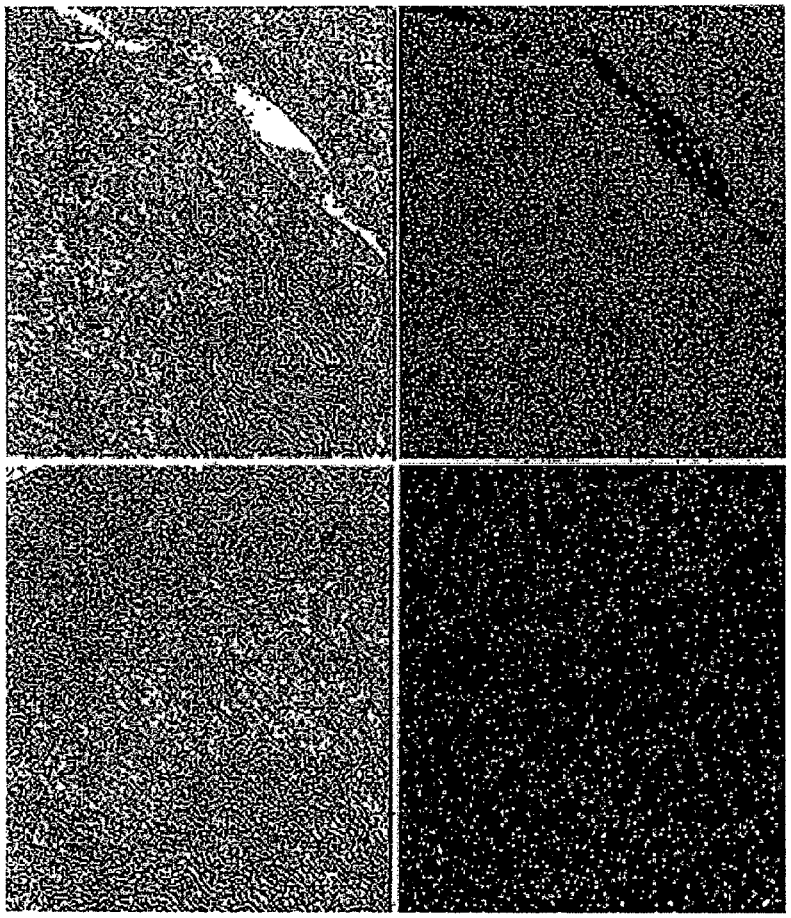
FIG. 16: TWEAK mRNA is widely expressed throughout the kidney in an adult wild-type mouse. A cross section of kidney is viewed at 5× magnification with hematoxylin staining, or under dark field microscopy following in situ hybridization with sense or anti-sense TWEAK probes.
Figure 17:
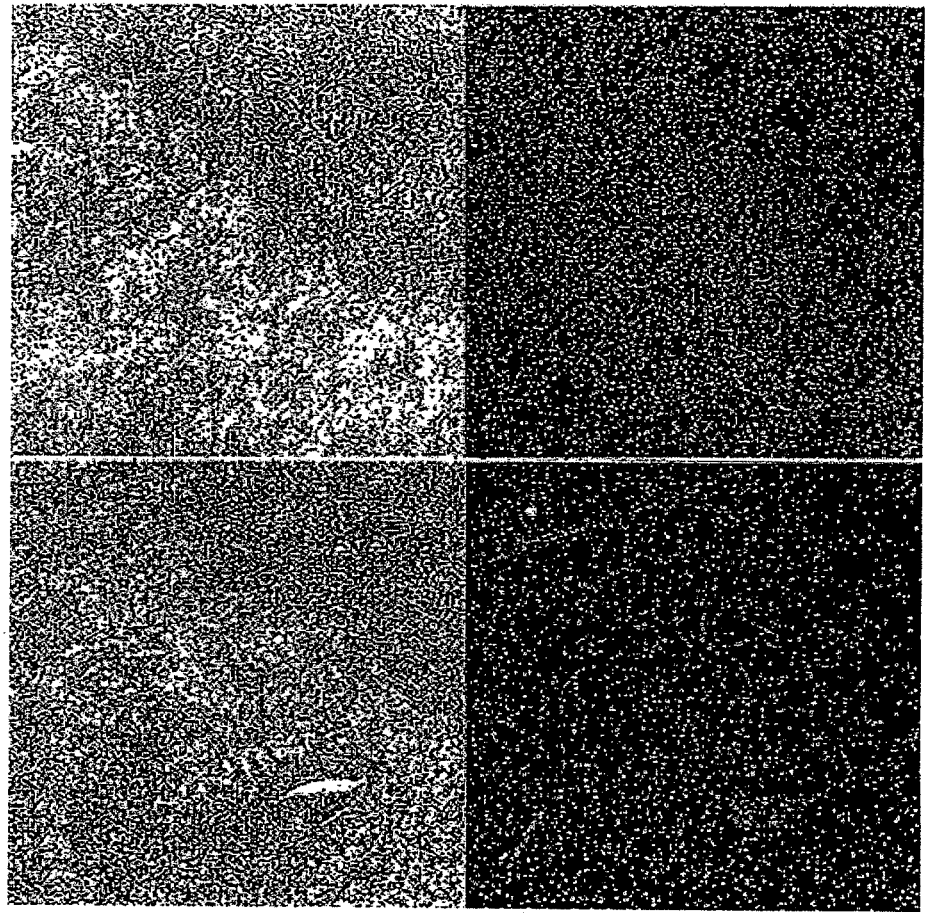
FIG. 17: Fn14 mRNA is expressed in the proximal tubules of outer medulla in adult wild-type mouse kidney. A cross section of kidney is viewed at 5× magnification with hematoxylin staining, or under dark field microscopy following in situ hybridization with sense or anti-sense Fn14 probes.
Figure 18:
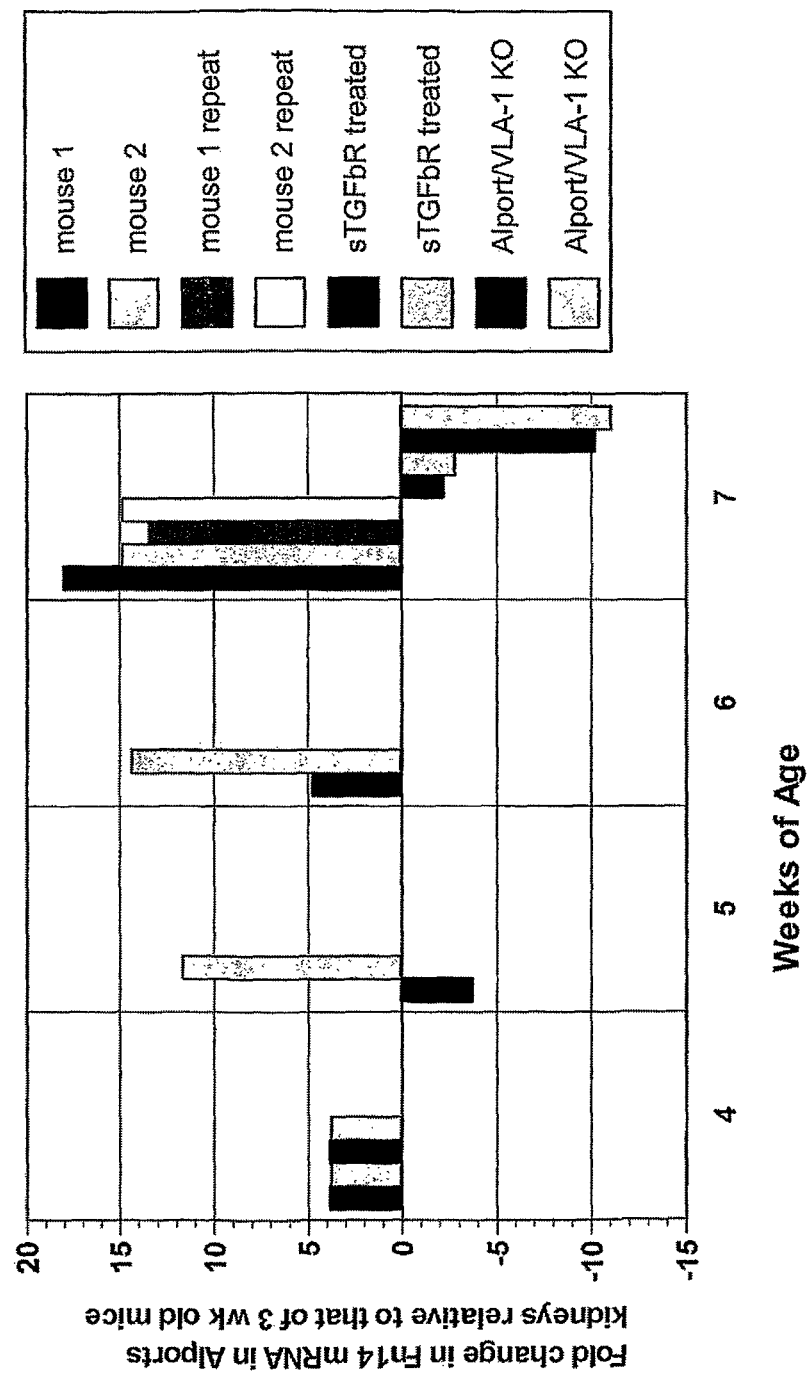
FIG. 18: A role for TWEAK in kidney fibrosis is suggested by the upregulation of Fn14 mRNA in Alports kidneys. The fold increase in Fn14 mRNA levels is shown in two individual mice carrying the mutation leading to Alports disease relative to wildtype animals at 4, 5, 6, and 7 weeks of age. mRNA levels were determined by hybridization to a gene chip containing nucleotide sequence corresponding to a portion of the Fn14 gene. At the 4 and 7 week time points, replicate results for each the two mice are shown (indicated by the mouse 1 repeat and mouse 2 repeat bars respectively). At the 7 week time point, Fn14 mRNA is shown to be reduced in two settings where disease is inhibited, i.e. sTGFβR-Fc treatment and in VLA-1 knockout mice (illustrated in FIG. 18 by either the two independent mice treated with sTGFβR-Fc ("sTGFbR treated") or the two independent Alport/VLA-1 KO mice ("Alport/VLA-1 KO").

Consistent with a role for TWEAK in kidney disease, TWEAK mRNA was shown to be expressed widely in adult C57BL/6 mouse kidney (FIG. 16), and Fn14 mRNA was shown to be expressed in the proximal tubules of the inner cortex/outer medulla (FIG. 17), as shown by in situ hybridization (ISH) using radiolabeled TWEAK and Fn14 antisense probes and revealed by dark field microscopy. Also, Fn14 mRNA was shown to be induced in the kidneys of mouse models for Alport syndrome. This is shown in FIG. 18 as the fold increase in Fn14 mRNA in two individual Alport mice relative to wildtype animals as disease progresses in the Alport mice from 4 to 7 weeks of age.

The role of TWEAK in a murine model of Alport disease was directly tested by treatment with a TWEAK antagonist, a murine Fn14-Fc fusion protein. Two groups of 5 Alport knockout (KO) mice prepared according to Cosgrove et al., Genes Dev. 10(23):2981-2992 (1996), were treated with control IgG2a (muP1.17), or muFN14-Fc fusion protein (prepared by Biogen (Cambridge)). The control IgG2a used is the murine myeloma protein P1.17 produced from a hybridoma and purified by standard mAb purification procedure. The muFN14-Fc is a fusion protein of the extracellular domain of murine Fn14 and the Fc region of murine IgG2a. The fusion protein was produced either in human 293 embryonic kidney cells or in Chinese hamster ovary (CHO) cells and purified by standard mAb purification procedures. The first treatment was at the age of three weeks with a dose of one hundred microgram of protein by an intraperitoneal (IP) route. Treatments continued for the next four weeks with the same dose administered twice a week. Mice were sacrificed at the end of the 7th week (7 week old). Kidneys were collected and embedded in paraffin and frozen. The extent of kidney fibrosis and inflammation was scored by glomerular morphology from H&E staining of paraffin sections, activated myofibroblast with smooth muscle actin staining, and activated monocytes by CD11b staining of frozen sections. Smooth muscle actin and CD11b stained sections were used to quantitate positively stained areas to assess extent of fibrosis and inflammation, respectively, by the MetaMorph computer program. Results of analysis show health of glomeruli in FN14-Fc treated mice was greatly improved (59% glomeruli with pathology in control Ig treated as compared to only 39% with pathology in Fn14-Fc treated, P value=0.03). Glomerular pathology is characterized by presence of crescents and/or glomerular fibrosis. In addition, fibrosis in the cortical area of the kidney in treated mice was significantly reduced as measured by alpha smooth muscle actin staining, p value=0.04. There was also a general trend in reduction of monocyte infiltration in FN14-Fc treated mice. These results clearly indicate that FN14-Fc treatment of Alports mice reduces fibrosis in the cortical area of the kidney and improves the general morphology of glomeruli.

The role of TWEAK was also tested in the murine model of unilateral ureteral obstruction-induced kidney fibrosis by treatment with a TWEAK antagonist, a hamster anti-TWEAK monoclonal antibody. In the mouse model for renal fibrotic progression, a ureter is ligated, resulting in unilateral ureteral obstruction (WO). (Klahr et al., Am J Kidney Dis 18:689-699 (1991); Moriyama et al., Kidney Int 54(1):110-119 (1998). WO causes progressive nephrosclerosis without near-term renal failure in mice because the unobstructed kidney can maintain relatively normal renal function. While the obstructed kidney undergoes rapid global fibrosis, the unobstructed kidney undergoes adaptive hypertrophy.

The impact of TWEAK antagonist treatment on UUO-induced renal fibrosis was quantitated morphometrically. Four groups of eight viral antigen-free C57BL/6 male mice (Jackson Laboratories, Bar Harbor Me.), 8-10 weeks of age were used. The mice were divided into the following groups: PBS alone (VEH), control hamster anti-Keyhole Limpet Hemocyanin (KLH) antibody (HA4/8; purchased from BD Biosciences (San Jose)), hamster anti-mouse TWEAK antibody (AB.G11; prepared by Biogen (Cambridge)), soluble murine TGF-β receptor Ig (TGF-βR, positive control; prepared by Biogen (Cambridge)) and unoperated (UNOP).

To induce kidney fibrosis, the left ureter was aseptically isolated and tied off in the kidney of the operated side on day 0 as described in Hammad et al., Kidney Int 58:242-250 (2000). The following groups: PBS, HA4/8 and AB.G11 (anti-TWEAK mAb) were additionally treated on days 2, 6, and 9 post surgery and the sTGF-βR-Ig group on days 1, 3, 6 and 8. On day 10 post surgery, the left ligated kidney was removed and halved transversely through the center of the renal pelvis and prepared for paraffin sectioning.

Figure 19:
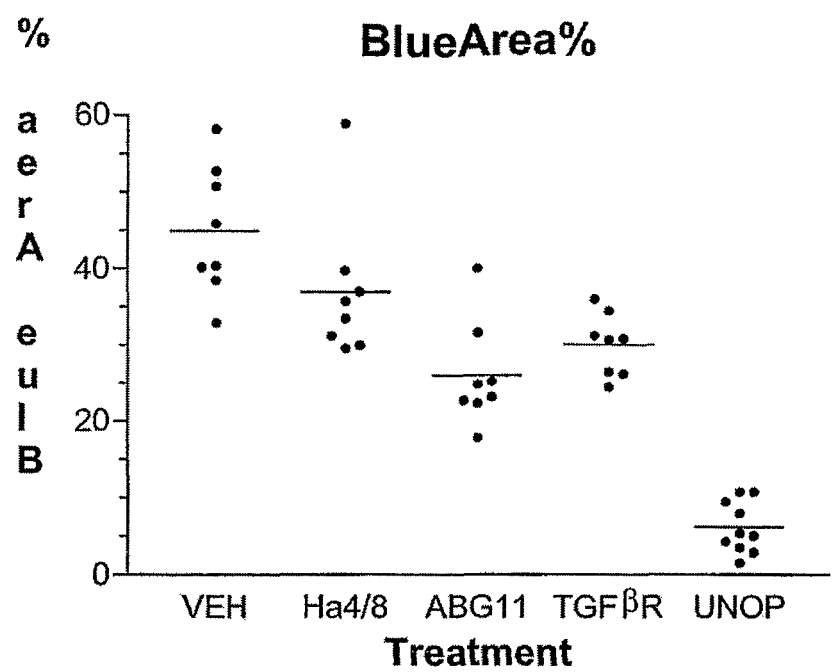
FIG. 19: TWEAK antagonist treatment in Unilateral Ureteral Obstruction (UUO), a murine model of kidney fibrosis, significantly reduced kidney fibrosis. Metamorph quantitation of blue-staining area (fibrotic area) on Trichrome-Masson stained paraffin kidney sections indicates that collagen content was decreased in AB.G11 (anti-TWEAK monoclonal Ab) treated kidney samples to similar levels observed in sTGF-βR-Ig positive control samples. In contrast, the isotype-control hamster antibody (HA4/8)-treated kidneys showed no reduction in kidney fibrosis, similar to vehicle (PBS)-treated kidneys.

Paraffin-treated kidney sections were stained with Trichrome-Masson staining specific for collagen. Using a Metamorph program, blue-staining areas in Trichrome-Masson slides were measured to quantitate collagen content in order to assess the extent of fibrosis in the operated kidneys (FIG. 19).

Surprisingly, kidney sections from anti-TWEAK monoclonal (AB.G11) antibody-treated animals demonstrated a 42% decrease in collagen content compared with PBS-treated animals and a 30% decrease in collagen content compared with control (HA4/8) antibody-treated animals. In contrast, the kidneys from soluble TGF-β receptor Ig-treated (TGF-βR) animals displayed only a 33% decrease in collagen content compared with PBS-treated animals and a 19% decrease in collagen content compared with control (HA4/8) antibody-treated animals. These results clearly show that treatment with a TWEAK antagonist, such as an anti-TWEAK monoclonal antibody, significantly reduced kidney fibrosis to a greater extent than that shown by soluble TGF-β receptor Ig (TGF-βR).

Taken together, the results presented herein show that TWEAK plays an important role in inflammatory kidney conditions, such as multifocal inflammation, and in non-inflammatory kidney conditions, such as tubular nephropathy, cysts, glomerular nephropathy, Alports syndrome, tubular basophilia, tubular dilatation, tubular vacuolation, hyaline casts, tubular hyperplasia and kidney fibrosis.

Example 6

TWEAK Causes Lung Inflammation

Figure 20:
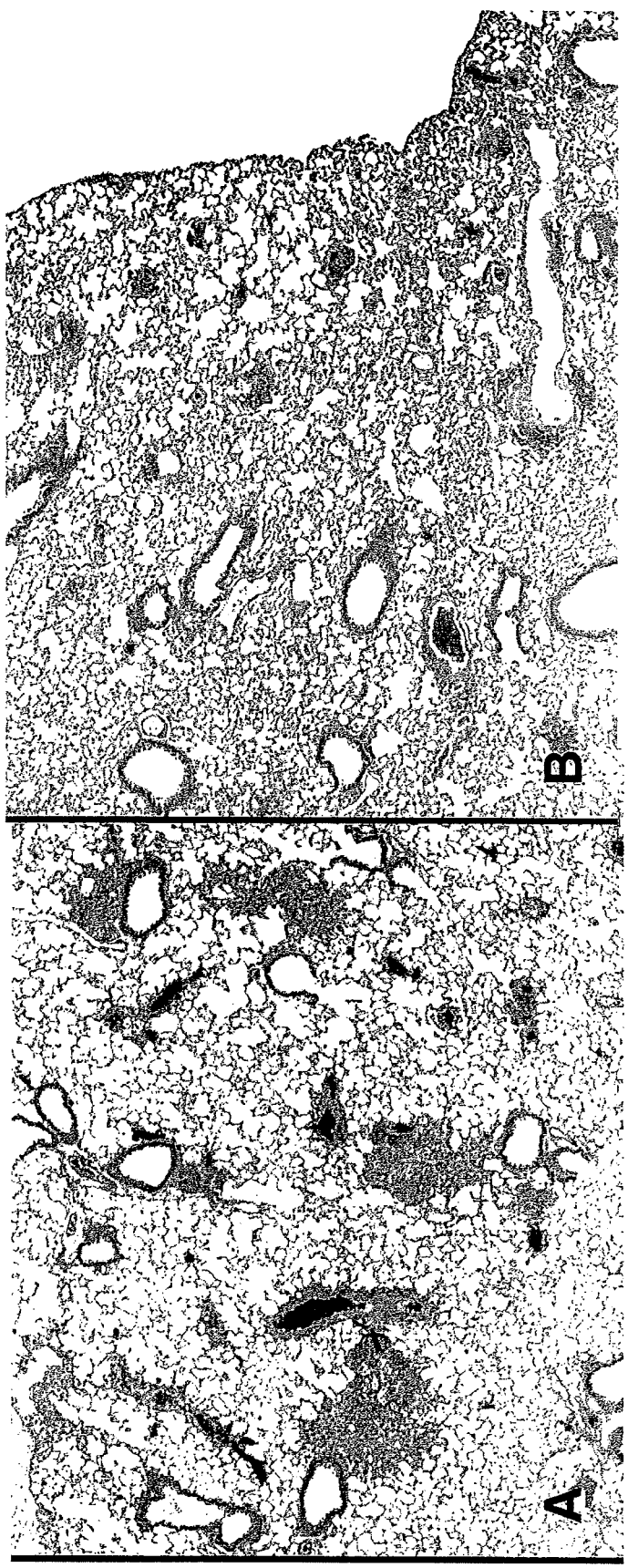
FIG. 20: The TWEAK transgene causes granulomatous and lymphohistocytic inflammation in the lung. A. A cross section of a lung from a FL-TWEAK transgenic (Tg) mouse with H&E staining. B. A cross section of a lung from a sTWEAK Tg mouse with H&E staining.
Figure 21:
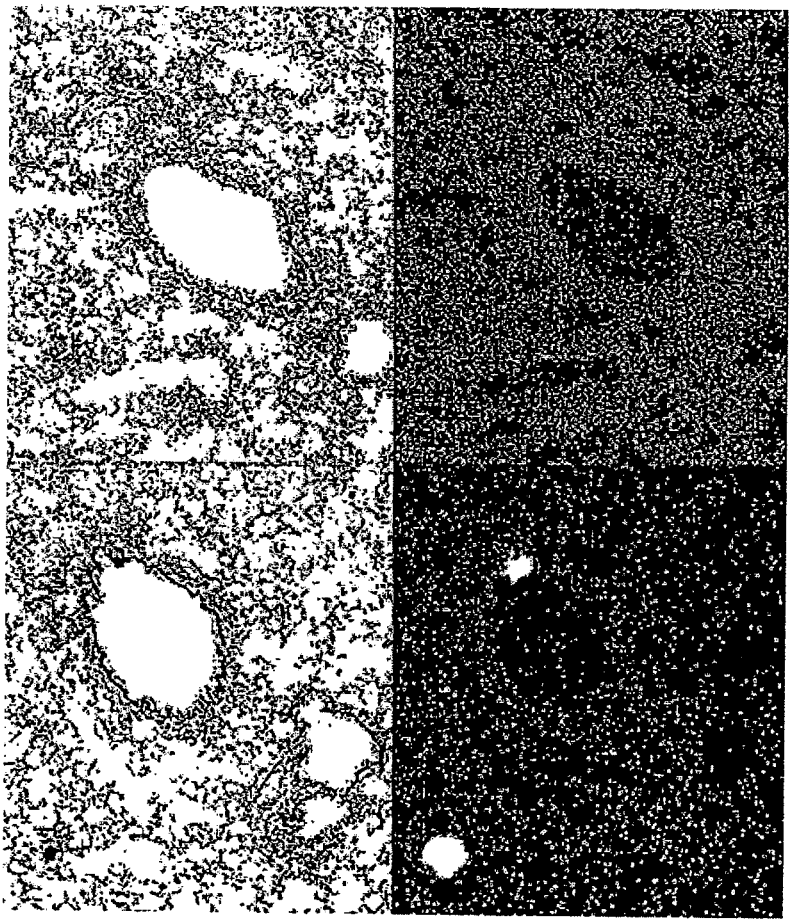
FIG. 21: TWEAK mRNA is expressed in the cells lining the bronchioles and alveoli in adult wild-type mouse lung. A cross section of lung is viewed at 10× magnification with hematoxylin staining, or under dark field microscopy following in situ hybridization with sense or anti-sense TWEAK probes.

In cross sections of lungs from FL-TWEAK transgenic and control mice as described in Example 1, marked granulomatous and lymphohistiocytic inflammation was shown in both FL-TWEAK and sTWEAK Tg mice (FIG. 20). Also, endogenous TWEAK expression was revealed in lung cells lining the bronchioles and alveoli of normal mice, as shown by in situ hybridization (ISH) using radio-labeled TWEAK antisense probes and revealed by dark field (ISH) microscopy (FIG. 21).

Figure 22:
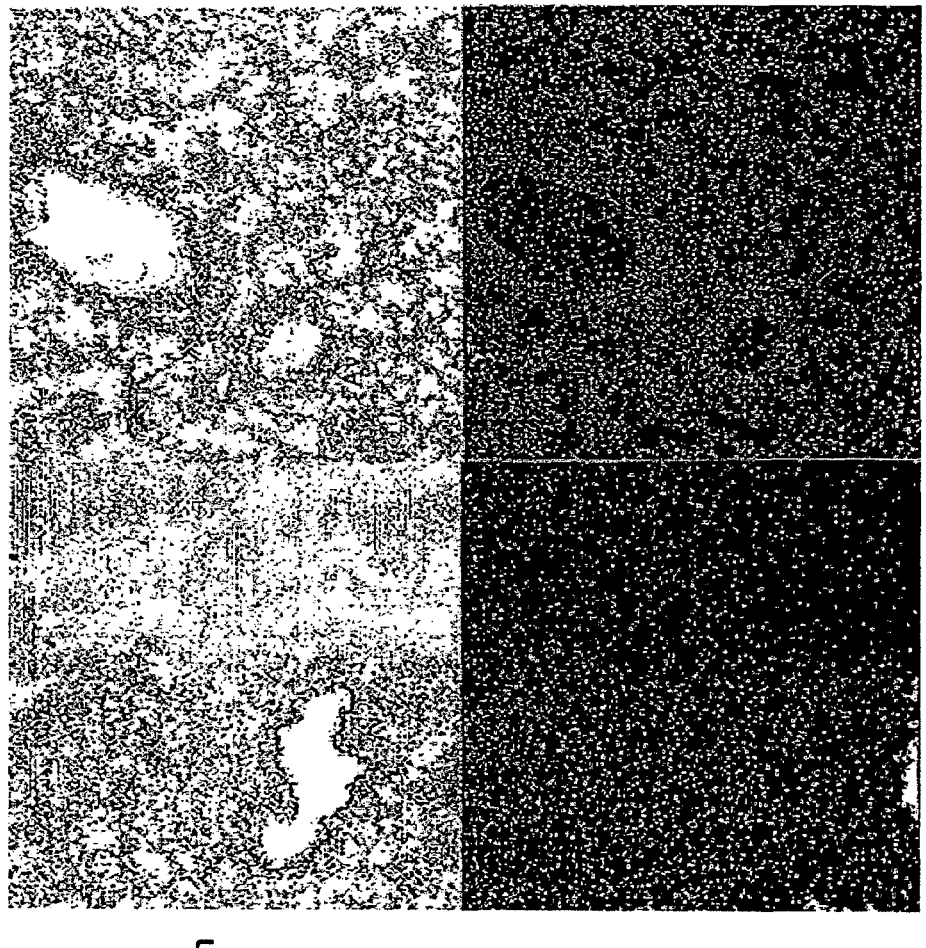
FIG. 22: Fn14 mRNA is expressed in the bronchioles and alveoli of adult wild-type mouse lung. A cross section of lung is viewed at 10× magnification with hematoxylin staining, or under dark field microscopy following in situ hybridization with sense or anti-sense Fn14 probes.

Consistent with a role for TWEAK in lung disease, Fn14 mRNA was shown to be expressed widely in adult C57BL/6 mouse lung (FIG. 22) by ISH using radio-labeled Fn14 antisense probes and revealed by dark field microscopy.

Taken together, these data show that TWEAK is an important factor in mediating inflammatory lung conditions, including granulomatous and lymphohistiocytic inflammation.

Example 7

TWEAK Inhibits Both Adipogenesis and Myogenesis

The effect of TWEAK on cellular differentiation was investigated using two in vitro models of adipogenesis and myogenesis well-known in the art. (Green and Meuth, *Cell* 3:127-133 (1974); Yaffe and Saxel, *Nature* 270: 725-727 (1977)).

For adipogenesis, 3T3-L1 cells were first grown to confluency in a Dulbecco's Modified Eagles Media (DMEM)-based growth media and then induced to undergo adipogenesis according to methods known in the art. Green and Kehinde, *Cell* 5:19-27 (1976). Briefly, cells were stimulated on day 0 with the DMEM-based MDI media that contained dexamethasone, insulin and IBMX for two days followed by insulin-only DMEM media for another two days. On day 5, cells were cultured in the regular DMEM-based growth media and adipogenesis was assessed on day 7 by Oil-Red staining.

For myogenesis, C2C12 cells were grown to near confluency in a DMEM-based growth media and on day 0, switched to a low-serum differentiation media that contained 2% horse serum to trigger differentiation (Yaffe and Saxel, *Nature* 270: 725-727 (1977)). Myotube formation was examined using a phase-contrast microscope and pictures were taken on day 6 of differentiation.

Figure 24:
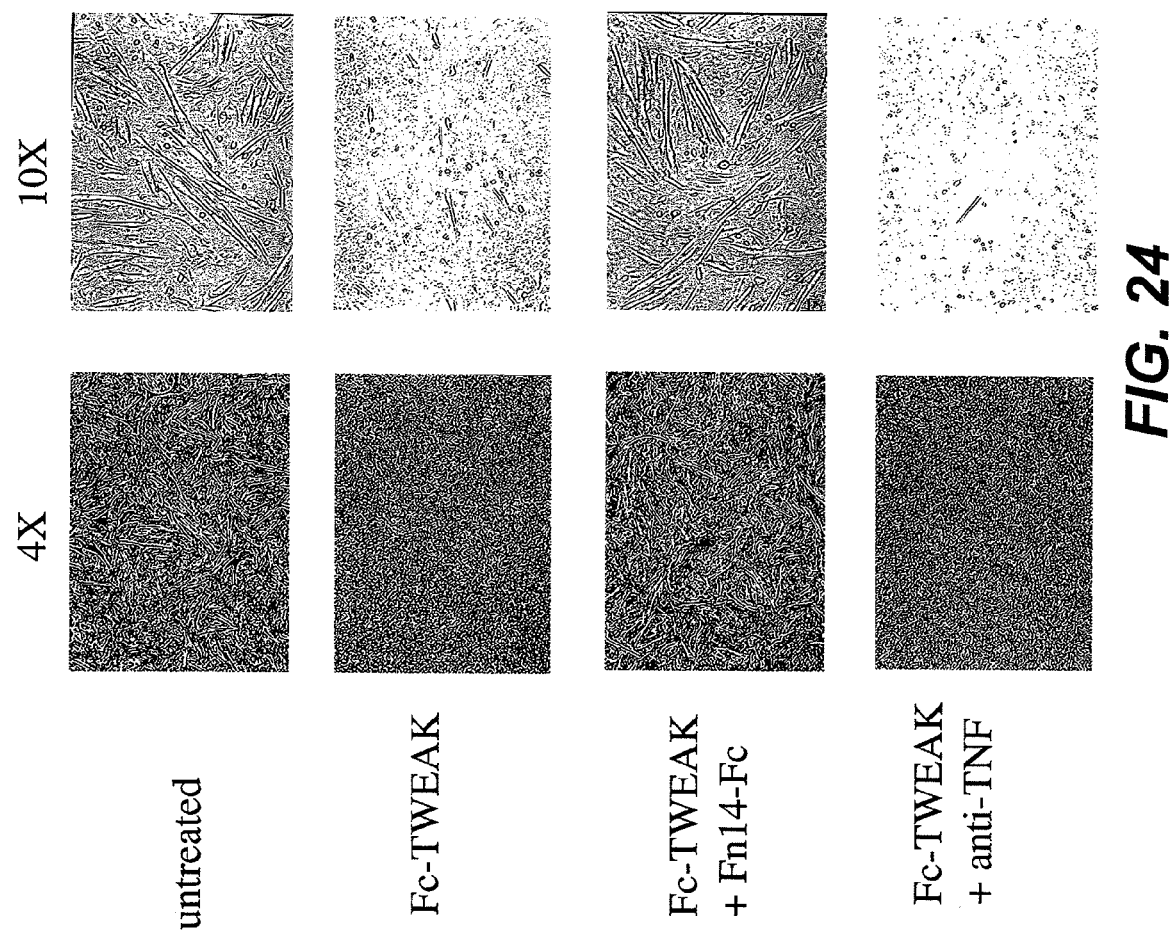
FIG. 24: Inhibitory effect of TWEAK on myogenesis in vitro. C2C12 myoblasts were grown to near confluency in a DMEM-based growth media and on day 0, switched to a low-serum differentiation media that contained 2% horse serum to trigger differentiation. Cells were untreated or treated on day 0 with Fc-hTWEAK (100 ng/ml). Myotube formation was examined using a phase-contrast microscope and pictures were taken on day 6 of differentiation. In other experimental groups, Fn14-Fc or a neutralizing anti-TNF antibody were added at the same time as Fc-hTWEAK, thereby demonstrating that the inhibitory effect of Fc-hTWEAK was TWEAK-specific and not mediated through TNF.

To examine the effect of TWEAK on these two differentiation pathways, various versions of recombinant human TWEAK (TWEAK-FLAG, TWEAK or Fc-TWEAK) were added on day 0 at a final concentration of 100 ng/ml and replenished daily. TWEAK inhibited both adipogenesis and myogenesis in both systems (FIGS. 23 and 24). The specificity of TWEAK'S inhibitory effect was confirmed using either the hamster anti-TWEAK monoclonal antibody AB.G11 or hFn14-Fc as the neutralizing reagent.

These results show that TWEAK plays an important role in cellular differentiation. The present invention therefore provides methods for affecting cellular differentiation of the progenitor cells disclosed herein using the TWEAK polypeptides, peptides, agonists, or antagonists disclosed herein.

Example 8

TWEAK Binds to Human Mesenchymal Stem Cells

Human mesenchymal stem cells (hMSCs) (Cambrex Corp., East Rutherford, N.J.) were cultured in MSCGM media (Cambrex) and harvested by incubating them with PBS containing 5 mM EDTA, and prepared for fluorescence activated cell sorting (FACS) analysis.

Figure 25:
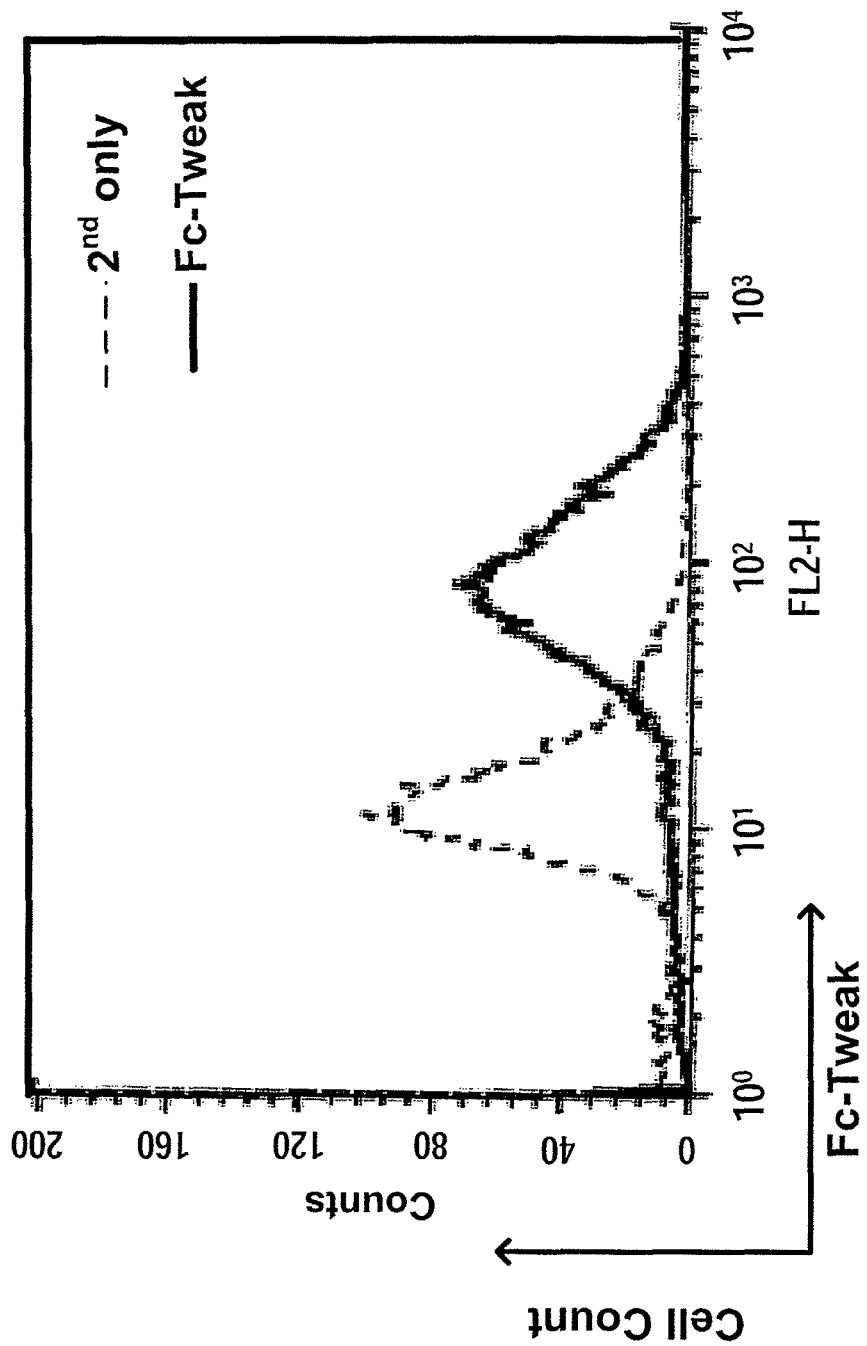
FIG. 25: TWEAK can bind to human mesenchymal stem cells. Human mesenchymal stem cells (hMSCs) were incubated with recombinant Fc-TWEAK protein followed by PE-conjugated goat anti-human Fc or goat anti-mouse Fc secondary antibodies. The ability of Fc-TWEAK to bind to hMSCs was determined using fluorescence activated cell sorter (FACS) analysis. The background staining is provided by the secondary antibody staining (2nd only) alone.

The cells were incubated in FACS buffer containing PBS and 1% FBS along with 100 ng/mL of Fc-TWEAK for 1 hour on ice. After washing twice with FACS buffer, the cells were then incubated with phycoerythrin-conjugated goat anti-human Fc or goat anti-mouse Fc secondary antibodies at a dilution of 1:200 (Jackson ImmunoResearch, West Grove, Pa.) (FIG. 25). The background staining was measured by secondary antibody staining alone, as shown by the broken line.

As shown in FIG. 25, TWEAK binds to human mesenchymal cells, as demonstrated by the shift in the staining profile of Fc-TWEAK compared with secondary antibody alone. Thus, the ability of TWEAK to bind to mesenchymal cells (a progenitor cell type capable of differentiating into muscle cells as well as cartilage, bone, connective tissue cell types such as stromal cells, fibroblasts, adipocytes and dermal cells) shows that TWEAK plays an important role in the differentiation of these cell types both in normal and disease models.

Example 9

Fn14 is Expressed on Neural Stem Cells

The expression of Fn14 was examined in the brains from embryonic day 13.5 mice on a mixture of both C57BL/6 and 129/Sve background. The brains were subjected to in situ hybridization with the Fn14 anti-sense probe. A positive signal was detectable in the subventricular zone of the embryonic ventricles, correlating with the position of neural stem cells (data not shown). These results show that Fn14 plays an important role in neural cellular differentiation.

Example 10

Methods for Identifying Therapeutic Agents for Treating TWEAK-Related Conditions In order to identify TWEAK antagonist compounds that act as therapeutic agents for the treatment of TWEAK-related conditions according to the present invention, a test animal, such as a mouse, is obtained that expresses an exogenous DNA encoding a TWEAK polypeptide, or a fragment, analog, mutein, or mimetic thereof. The animal is then exposed to a candidate compound that may function as a therapeutic agent for a TWEAK-related condition. Fibrotic, cardiac, kidney, liver, lung, skin, skeletal muscle, lipid, gastrointestinal tract, pancreas, reproductive organs, neural, cartilage, bone or connective tissue from the test animal is then compared to the same tissue from a reference animal that expresses the exogenous DNA but has not been exposed to the compound; and it is determined whether the compound has affected any TWEAK-related condition of the fibrotic, cardiac, kidney, liver, lung, skin, skeletal muscle, lipid, gastrointestinal tract, pancreas, reproductive organs, neural, cartilage, bone or connective tissues.

In order to identify TWEAK agonist compounds that act as therapeutic agents for the treatment of TWEAK-related conditions according to the present invention, a test animal that either does or does not express an exogenous DNA encoding a TWEAK polypeptide, or a fragment, analog, mutein, or mimetic thereof may be exposed to a candidate compound that may function as a therapeutic agent for a TWEAK-related condition. Fibrotic, cardiac, kidney, liver, or lung tissue from the test animal is then compared to the same tissue from a reference animal that has not been exposed to the compound; and it is determined whether the compound has induced any biological change in said tissues as described herein due to TWEAK signaling in vivo.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein, including the appended claims.

The invention claimed is:

1. A method for treating pulmonary, liver, or cardiac fibrosis in a human subject in need thereof, comprising administering to the subject a therapeutically effective amount of a TWEAK antagonist, wherein the TWEAK antagonist is an antibody, or an antigen-binding fragment thereof, that binds human TWEAK.

2. The method of claim 1, wherein the fibrosis is liver fibrosis.

3. The method of claim 1, wherein the fibrosis is cardiac fibrosis.

4. The method of claim 1, wherein the fibrosis is pulmonary fibrosis.

5. The method of claim 2, wherein the antibody or antigen-binding fragment thereof is human or humanized.

6. The method of claim 2, wherein the antibody or antigen-binding fragment thereof is monoclonal or chimeric.

7. The method of claim 2, wherein a full length antibody is administered.

8. The method of claim 2, wherein an antigen-binding fragment of the antibody is administered.

9. The method of claim 2, wherein the TWEAK antagonist is administered to the subject via a route selected from the group consisting of: injection, transmucosal, oral, inhalation, ocular, rectal, stent implantation, topical, parenteral, long acting implantation, sustained release, and aural routes.

10. The method of claim 2, wherein the TWEAK antagonist is in a delivery formulation selected from the group consisting of: tablets, pills, liposomes, granules, spheres, dragees, capsules, liquids, gels, syrups, slurries, suspensions, stent coatings, and sustained-release formulations.

11. The method of claim 3, wherein the antibody or antigen-binding fragment thereof is human or humanized.

12. The method of claim 3, wherein the antibody or antigen-binding fragment thereof is monoclonal or chimeric.

13. The method of claim 3, wherein a full length antibody is administered.

14. The method of claim 3, wherein an antigen-binding fragment of the antibody is administered.

15. The method of claim 3, wherein the TWEAK antagonist is administered to the subject via a route selected from the group consisting of: injection, transmucosal, oral, inhalation, ocular, rectal, stent implantation, topical, parenteral, long acting implantation, sustained release, and aural routes.

16. The method of claim 3, wherein the TWEAK antagonist is in a delivery formulation selected from the group consisting of: tablets, pills, liposomes, granules, spheres, dragees, capsules, liquids, gels, syrups, slurries, suspensions, stent coatings, and sustained-release formulations.

17. The method of claim 4, wherein the antibody or antigen-binding fragment thereof is human or humanized.

18. The method of claim 4, wherein the antibody or antigen-binding fragment thereof is monoclonal or chimeric.

19. The method of claim 4, wherein a full length antibody is administered.

20. The method of claim 4, wherein an antigen-binding fragment of the antibody is administered.

21. The method of claim 4, wherein the TWEAK antagonist is administered to the subject via a route selected from the group consisting of: injection, transmucosal, oral, inhalation, ocular, rectal, stent implantation, topical, parenteral, long acting implantation, sustained release, and aural routes.

22. The method of claim 4, wherein the TWEAK antagonist is in a delivery formulation selected from the group consisting of: tablets, pills, liposomes, granules, spheres, dragees, capsules, liquids, gels, syrups, slurries, suspensions, stent coatings, and sustained-release formulations.

* * * * *

SEQUENCE LISTING

<160> NUMBER OF SEQ ID NOS: 5

<210> SEQ ID NO 1
<211> LENGTH: 249
<212> TYPE: PRT
<213> ORGANISM: Mus musculus

<400> SEQUENCE: 1

```
Met Ala Ala Arg Arg Ser Gln Arg Arg Gly Arg Gly Glu Pro
1               5                   10                  15
Gly Thr Ala Leu Leu Ala Pro Leu Val Leu Ser Leu Gly Leu Ala Leu
                20                  25                  30
Ala Cys Leu Gly Leu Leu Leu Val Val Ser Leu Gly Ser Trp Ala
            35                  40                  45
Thr Leu Ser Ala Gln Glu Pro Ser Gln Glu Glu Leu Thr Ala Glu Asp
    50                  55                  60
Arg Arg Glu Pro Pro Glu Leu Asn Pro Gln Thr Glu Glu Ser Gln Asp
65                  70                  75                  80
Val Val Pro Phe Leu Glu Gln Leu Val Arg Pro Arg Arg Ser Ala Pro
                85                  90                  95
Lys Gly Arg Lys Ala Arg Pro Arg Arg Ala Ile Ala Ala His Tyr Glu
            100                 105                 110
Val His Pro Arg Pro Gly Gln Asp Gly Ala Gln Ala Gly Val Asp Gly
        115                 120                 125
Thr Val Ser Gly Trp Glu Glu Thr Lys Ile Asn Ser Ser Ser Pro Leu
    130                 135                 140
Arg Tyr Asp Arg Gln Ile Gly Glu Phe Thr Val Ile Arg Ala Gly Leu
145                 150                 155                 160
Tyr Tyr Leu Tyr Cys Gln Val His Phe Asp Glu Gly Lys Ala Val Tyr
                165                 170                 175
Leu Lys Leu Asp Leu Leu Val Asn Gly Val Leu Ala Leu Arg Cys Leu
            180                 185                 190
Glu Glu Phe Ser Ala Thr Ala Ala Ser Ser Pro Gly Pro Gln Leu Arg
        195                 200                 205
Leu Cys Gln Val Ser Gly Leu Leu Pro Leu Arg Pro Gly Ser Ser Leu
    210                 215                 220
Arg Ile Arg Thr Leu Pro Trp Ala His Leu Lys Ala Ala Pro Phe Leu
225                 230                 235                 240
Thr Tyr Phe Gly Leu Phe Gln Val His
                245
```

<210> SEQ ID NO 2
<211> LENGTH: 1239
<212> TYPE: DNA
<213> ORGANISM: Mus musculus

<400> SEQUENCE: 2

```
atggccgccc gtcggagcca gaggcggagg gggcgccggg gggagccggg caccgccctg      60
ctggccccgc tggtgctgag cctgggcctg gcgctggcct gccttggcct cctgctggtc     120
gtggtcagcc tggggagctg ggcaacgctg tctgcccagg agccttctca ggaggagctg     180
acagcagagg accgccggga gcccccctgaa ctgaatcccc agacagagga aagccaggat     240
gtggtacctt tcttggaaca actagtccgg cctcgaagaa gtgctcctaa aggccggaag     300
gcgcggcctc gccgagctat tgcagcccat tatgaggttc atcctcggcc aggacaggat     360
ggagcacaag caggtgtgga tgggacagtg agtggctggg aagagaccaa aatcaacagc     420
```

```
tccagccctc tgcgctacga ccgccagatt ggggaattta cagtcatcag ggctgggctc    480
tactacctgt actgtcaggt gcactttgat gagggaaagg ctgtctacct gaagctggac    540
ttgctggtga acggtgtgct ggccctgcgc tgcctggaag aattctcagc cacagcagca    600
agctctcctg gccccagct ccgtttgtgc caggtgtctg ggctgttgcc gctgcggcca    660
gggtcttccc ttcggatccg caccctcccc tgggctcatc ttaaggctgc cccttccta    720 acctactttg gactctttca agttcactga ggggccttgc tctcccagat tcctaaaact    780
ttccctggct ccaggagcat caccacacct ccctacccca ccccactcc tccacccccct   840 cgctgctcct tggtccagtc ctgtctctcc tcaaaggcag ccagagcttg ttcacatgtt    900
tccattccac agacgtatcc ttgctcttct aacatccca tcccaccaca actatccacc    960
tcactagctc ccaaagcccc tacttatccc tgactccccc acccactcac ccgaccacgt   1020
gtttattgac tttgtgcacc aggcactgag atgggctgga cctggtggca ggaagccaga   1080
gaacctggga ctaggccaga agttcccaac tgtgagggggg aagagctggg gacaagctcc   1140
tccctggatc cctgtggatt ttgaaaagat actatttta ttattattgt gacaaaatgt    1200
taaatggata ttaaagagaa taaatcatga tttctcttc                          1239
```

<210> SEQ ID NO 3
<211> LENGTH: 249
<212> TYPE: PRT
<213> ORGANISM: Homo sapiens
<400> SEQUENCE: 3

```
Met Ala Ala Arg Arg Ser Gln Arg Arg Gly Arg Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220
```

```
Arg Ile Arg Thr Leu Pro Trp Ala His Leu Lys Ala Ala Pro Phe Leu
225                 230                 235                 240

Thr Tyr Phe Gly Leu Phe Gln Val His
                245
```

<210> SEQ ID NO 4
<211> LENGTH: 129
<212> TYPE: PRT
<213> ORGANISM: Homo sapiens

<400> SEQUENCE: 4

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln
```

<210> SEQ ID NO 5
<211> LENGTH: 309
<212> TYPE: PRT
<213> ORGANISM: Artificial Sequence
<220> FEATURE:
<223> OTHER INFORMATION: human TWEAK receptor fusion protein construct

<400> SEQUENCE: 5

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Arg
65                  70                  75                  80

Ser Cys Asp Lys Thr His Thr Cys Pro Pro Cys Pro Ala Pro Glu Ala
                85                  90                  95

Glu Gly Ala Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
130                 135                 140

Glu Val His Asn Ala Lys Thr Lys Pro Arg Glu Glu Gln Tyr Asn Ser
145                 150                 155                 160
```

-continued

```
Thr Tyr Arg Val Val Ser Val Leu Thr Val Leu His Gln Asp Trp Leu
                165                 170                 175
Asn Gly Lys Glu Tyr Lys Cys Lys Val Ser Asn Lys Ala Leu Pro Ala
            180                 185                 190
Pro Ile Glu Lys Thr Ile Ser Lys Ala Lys Gly Gln Pro Arg Glu Pro
        195                 200                 205
Gln Val Tyr Thr Leu Pro Pro Ser Arg Glu Glu Met Thr Lys Asn Gln
    210                 215                 220
Val Ser Leu Thr Cys Leu Val Lys Gly Phe Tyr Pro Ser Asp Ile Ala
225                 230                 235                 240
Val Glu Trp Glu Ser Asn Gly Gln Pro Glu Asn Asn Tyr Lys Thr Thr
                245                 250                 255
Pro Pro Val Leu Asp Ser Asp Gly Ser Phe Phe Leu Tyr Ser Lys Leu
            260                 265                 270
Thr Val Asp Lys Ser Arg Trp Gln Gln Gly Asn Val Phe Ser Cys Ser
        275                 280                 285
Val Met His Glu Ala Leu His Asn His Tyr Thr Gln Lys Ser Leu Ser
    290                 295                 300
Leu Ser Pro Gly Lys
305
```